United States Patent
Fung et al.

(10) Patent No.: US 8,698,639 B2
(45) Date of Patent: Apr. 15, 2014

(54) SYSTEM AND METHOD FOR RESPONDING TO DRIVER BEHAVIOR

(75) Inventors: Kin Fung, Dublin, OH (US); Timothy J. Dick, Dublin, OH (US)

(73) Assignee: Honda Motor Co., Ltd., Tokyo (JP)

( * ) Notice: Subject to any disclaimer, the term of this patent is extended or adjusted under 35 U.S.C. 154(b) by 400 days.

(21) Appl. No.: 13/030,637

(22) Filed: Feb. 18, 2011

(65) Prior Publication Data
US 2012/0212353 A1  Aug. 23, 2012

(51) Int. Cl.
*G08B 23/00* (2006.01)

(52) U.S. Cl.
USPC .............................. 340/576; 701/51; 701/70

(58) Field of Classification Search
USPC ............... 340/426.1, 426.11, 426.19, 426.25, 340/426.32, 575, 576, 439, 435, 457.1; 701/1, 36, 51, 70
See application file for complete search history.

(56) References Cited

U.S. PATENT DOCUMENTS

| | | | |
|---|---|---|---|
| 5,057,834 A | 10/1991 | Nordstrom | |
| 5,485,892 A | 1/1996 | Fujita | |
| 5,913,375 A | 6/1999 | Nishikawa | |
| 5,942,979 A | 8/1999 | Luppino | |
| 6,009,377 A | 12/1999 | Hiwatashi | |
| 6,104,296 A | 8/2000 | Yasushi et al. | |
| 6,185,487 B1 | 2/2001 | Kondo et al. | |
| 6,337,629 B1 | 1/2002 | Bader | |
| 6,393,348 B1 | 5/2002 | Ziegler et al. | |
| 6,435,626 B1 | 8/2002 | Kostadina | |
| 6,485,415 B1 | 11/2002 | Uchiyama et al. | |
| 6,485,418 B2 | 11/2002 | Yasushi et al. | |
| 6,542,081 B2 * | 4/2003 | Torch | 340/575 |
| 6,697,723 B2 | 2/2004 | Olsen et al. | |
| 6,734,799 B2 | 5/2004 | Munch | |
| 6,791,462 B2 | 9/2004 | Choi | |
| 6,809,643 B1 | 10/2004 | Elrod et al. | |
| 6,822,573 B2 | 11/2004 | Basir et al. | |
| 6,909,947 B2 | 6/2005 | Douros et al. | |

(Continued)

FOREIGN PATENT DOCUMENTS

| | | |
|---|---|---|
| DE | 102009051260 | 6/2010 |
| DE | 202012001096 U1 | 5/2012 |

(Continued)

OTHER PUBLICATIONS

Wiegand et al., Development and Evaluation of a Naturalistic Observer Rating of Drowsiness Protocol; Feb. 2, 2009 retrieved from the internet, retrieved on [May 14, 2012]; http://scholar.lib.vt.edu/VTTI/reports/ORD_Final_Report_022509.pdf, entire document.

(Continued)

*Primary Examiner* — Thomas Mullen
(74) *Attorney, Agent, or Firm* — Rankin, Hill & Clark LLP

(57) ABSTRACT

Methods of assessing driver behavior include monitoring vehicle systems and driver monitoring systems to accommodate for a driver's slow reaction time, attention lapse and/or alertness. When it is determined that a driver is drowsy, for example, the response system may modify the operation of one or more vehicle systems. The systems that may be modified include: visual devices, audio devices, tactile devices, antilock brake systems, automatic brake prefill systems, brake assist systems, auto cruise control systems, electronic stability control systems, collision warning systems, lane keep assist systems, blind spot indicator systems, electronic pretensioning systems and climate control systems.

69 Claims, 54 Drawing Sheets

(56) References Cited

U.S. PATENT DOCUMENTS

| | | | |
|---|---|---|---|
| 6,950,027 | B2 | 9/2005 | Banas |
| 6,974,414 | B2 | 12/2005 | Victor |
| 7,032,705 | B2 | 4/2006 | Zheng et al. |
| 7,046,128 | B2 | 5/2006 | Roberts |
| 7,092,849 | B2 | 8/2006 | Lafitte et al. |
| 7,102,495 | B2 | 9/2006 | Mattes et al. |
| 7,138,938 | B1 | 11/2006 | Prakah-Asante et al. |
| 7,183,930 | B2 | 2/2007 | Basir et al. |
| 7,183,932 | B2 | 2/2007 | Bauer |
| 7,196,629 | B2 | 3/2007 | Ruoss et al. |
| 7,248,997 | B2 | 7/2007 | Nagai et al. |
| 7,254,439 | B2 | 8/2007 | Misczynski et al. |
| 7,266,430 | B2 | 9/2007 | Basson et al. |
| 7,283,056 | B2 | 10/2007 | Bukman et al. |
| 7,304,580 | B2 | 12/2007 | Sullivan et al. |
| 7,349,792 | B2 | 3/2008 | Durand |
| 7,350,608 | B2 | 4/2008 | Fernandez |
| 7,401,233 | B2 | 7/2008 | Duri et al. |
| 7,424,357 | B2 | 9/2008 | Ozaki et al. |
| 7,465,272 | B2 | 12/2008 | Kriger |
| 7,502,152 | B2 | 3/2009 | Lich et al. |
| 7,507,207 | B2 | 3/2009 | Sakai et al. |
| 7,511,833 | B2 | 3/2009 | Breed |
| 7,517,099 | B2 | 4/2009 | Hannah |
| 7,532,964 | B2 | 5/2009 | Fujita et al. |
| 7,576,642 | B2 | 8/2009 | Rodemer |
| 7,618,091 | B2 | 11/2009 | Akaike et al. |
| 7,620,521 | B2 | 11/2009 | Breed et al. |
| 7,639,148 | B2 | 12/2009 | Victor |
| 7,649,445 | B2 | 1/2010 | Kuramori et al. |
| 7,650,217 | B2 | 1/2010 | Ueyama |
| 7,663,495 | B2 | 2/2010 | Haque et al. |
| 7,672,764 | B2 | 3/2010 | Yoshioka et al. |
| 7,719,431 | B2 | 5/2010 | Bolourchi |
| RE41,376 | E | 6/2010 | Torch |
| 7,803,111 | B2 | 9/2010 | Kriger |
| 7,805,224 | B2 | 9/2010 | Basson et al. |
| 7,809,954 | B2 | 10/2010 | Miller et al. |
| 7,864,039 | B2 | 1/2011 | Georgeson |
| 7,866,703 | B2 | 1/2011 | Spahn et al. |
| 7,948,387 | B2 | 5/2011 | Ishida et al. |
| 8,140,241 | B2 | 3/2012 | Takeda et al. |
| 8,157,730 | B2 | 4/2012 | LeBoeuf et al. |
| 2005/0022606 | A1 | 2/2005 | Partin et al. |
| 2005/0080533 | A1 | 4/2005 | Basir et al. |
| 2005/0246134 | A1 | 11/2005 | Nagai et al. |
| 2006/0082437 | A1 | 4/2006 | Yuhara |
| 2006/0161322 | A1 | 7/2006 | Njoku |
| 2006/0212195 | A1 | 9/2006 | Veith et al. |
| 2006/0283652 | A1 | 12/2006 | Yanai et al. |
| 2007/0190970 | A1 | 8/2007 | Watson |
| 2007/0243854 | A1 | 10/2007 | Taki et al. |
| 2007/0265540 | A1 | 11/2007 | Fuwamoto et al. |
| 2007/0299910 | A1 | 12/2007 | Fontenot et al. |
| 2008/0015422 | A1 | 1/2008 | Wessel |
| 2008/0033518 | A1 | 2/2008 | Rousso et al. |
| 2008/0167757 | A1 | 7/2008 | Kanevsky et al. |
| 2008/0183388 | A1 | 7/2008 | Goodrich |
| 2008/0195261 | A1 | 8/2008 | Breed |
| 2008/0228046 | A1 | 9/2008 | Futatsuyama et al. |
| 2008/0294015 | A1 | 11/2008 | Tsuji |
| 2008/0312796 | A1 | 12/2008 | Matsuura et al. |
| 2009/0040054 | A1 | 2/2009 | Wang et al. |
| 2009/0091435 | A1* | 4/2009 | Bolourchi ............... 340/435 |
| 2009/0156988 | A1 | 6/2009 | Ferren et al. |
| 2009/0209829 | A1 | 8/2009 | Yanagidaira et al. |
| 2009/0234552 | A1 | 9/2009 | Takeda et al. |
| 2009/0268022 | A1 | 10/2009 | Omi |
| 2009/0318777 | A1 | 12/2009 | Kameyama |
| 2009/0326399 | A1 | 12/2009 | Barrero Batalloso et al. |
| 2010/0049068 | A1 | 2/2010 | Fuwamoto et al. |
| 2010/0106365 | A1 | 4/2010 | Visconti et al. |
| 2010/0148923 | A1 | 6/2010 | Takizawa |
| 2010/0185101 | A1 | 7/2010 | Sakai et al. |
| 2010/0222687 | A1 | 9/2010 | Thijs et al. |
| 2010/0234692 | A1 | 9/2010 | Kuo et al. |
| 2010/0295707 | A1 | 11/2010 | Bennie et al. |
| 2011/0028857 | A1 | 2/2011 | Rodriguez Ibanez et al. |
| 2011/0046970 | A1 | 2/2011 | Fontenot |
| 2011/0213511 | A1 | 9/2011 | Visconti et al. |
| 2012/0010514 | A1 | 1/2012 | Vrazic |
| 2012/0054054 | A1 | 3/2012 | Kameyama |
| 2012/0083668 | A1 | 4/2012 | Pradeep et al. |

FOREIGN PATENT DOCUMENTS

| | | |
|---|---|---|
| FR | 2880166 | 6/2006 |
| JP | 11-151231 | 6/1999 |
| JP | 11-328593 | 11/1999 |
| JP | 2000-57479 | 2/2000 |
| JP | 2004-246708 | 9/2004 |
| JP | 2005-168908 | 6/2005 |
| JP | 3687356 B2 | 8/2005 |
| JP | 2006-302206 | 11/2006 |
| JP | 3862192 B2 | 12/2006 |
| JP | 2007-229116 | 9/2007 |
| JP | 2009-080718 | 4/2009 |
| JP | 2009-172205 | 8/2009 |
| WO | 02/096694 | 12/2002 |
| WO | 2007090896 | 8/2007 |
| WO | 2009098731 | 8/2009 |

OTHER PUBLICATIONS

International Search Report and Written Opinion mailed May 23, 2012 in PCT Application No. PCT/US2012/023362.

Serbedzija, et al. "Vehicle as a Co-Driver", 1st International Symposium on Vehicular Computing Systems, Published May 16, 2010, 7 pages.

http://media.ford.com/article_display_cfm?article_id=36728 "Ford Research Developing Intelligent System to Help Drivers Manage Stressful Situations on the Road", Dearborn, Michigan, Jun. 27, 2012, 2 pages.

http://reflect.pst.ifi.lmu.de/ "The Reflect Project" article (1 page) and Video Link to "The Reflect Project" : http://vimeo.com/25081038, filmed in Maranello, Italy, Mar. 2011, 7 minutes, 53 seconds.

Anneke Heitmann, Rainer Guttkuhn, Acacia Aguirre, Udo Trutschel, Martin Moore-Ede, "Technologies for the monitoring and prevention of driver fatigue," Proceedings of the First International Driving Symposium on Human Factors in Driver Assessment, Training and Vehicle Design, 2001, pp. 81-86.

Greg Kable, "Ferrari plans mind reading tech," Autocar.co.uk, Jan. 7, 2011 (last visited May 13, 2011).

Martin M. Ofalt, Jr., "Ford, MIT Partnering to Increase Driver Wellness and Safety," The College Driver.com, Jan. 24, 2010 (last visited May 9, 2011).

Press Release, "Ford and MIT research study shows technological advancements reduce stress on driver," http://web.mit.edu/press/2010/ford-mit-release.html, Nov. 4, 2010 (last visited May 9, 2011).

Bryan Reimer, Bruce Mehler & Joseph F. Coughlin, "An Evaluation of Driver Reactions to New Vehicle Parking Assist Technologies Developed to Reduce Driver Stress," MIT AgeLab White Paper, Nov. 4, 2010, pp. 1-26.

P. Boyraz, M. Acar, D. Kerr, "Multi-sensor driver drowsiness monitoring," Proceedings of the I MECH E Part D Journal of Automobile Engineering, vol. 222, No. 11, Jul. 23, 2008, pp. 1857-1878.

\* cited by examiner

| NO. | VEHICLE SYSTEMS | RESPONSE SYSTEM IMPACT | DRIVER'S BENEFIT | TYPE OF IMPACT |
|---|---|---|---|---|
| 1 | ELECTRONIC STABILITY CONTROL | ENHANCE STABILITY | COMPENSATE FOR DRIVER'S SLOWER REACTION TIME | CONTROL |
| 2 | ANTI-LOCK BRAKE | DECREASE STOPPING DISTANCE | COMPENSATE FOR DRIVER'S SLOWER REACTION TIME | CONTROL |
| 3 | BRAKE ASSIST | APPLY BRAKE FORCE QUICKER | COMPENSATE FOR DRIVER'S SLOWER REACTION TIME | CONTROL |
| 4 | BRAKE PREFILL SYSTEM | PREPARE BRAKE FOR QUICKER RESPONSE | COMPENSATE FOR DRIVER'S SLOWER REACTION TIME | CONTROL |
| 5 | LOW SPEED FOLLOW | DISABLE FUNCTION | PROTECT FOR DRIVER'S ATTENTION LAPSE | CONTROL |
| 6 | CRUISE CONTROL | DISABLE FUNCTION | PROTECT FOR DRIVER'S ATTENTION LAPSE | CONTROL |
| 7 | COLLISION WARNING | WARN SOONER | PROTECT FOR DRIVER'S ATTENTION LAPSE | WARNING |
| 8 | COLLISION MITIGATION BRAKING SYSTEM | WARN SOONER | PROTECT FOR DRIVER'S ATTENTION LAPSE | WARNING |
| 9 | AUTO CRUISE CONTROL | INCREASE VEHICLE GAP | PROTECT FOR DRIVER'S ATTENTION LAPSE | WARNING |
| 10 | LANE DEPARTURE WARNING | WARN SOONER | PROTECT FOR DRIVER'S ATTENTION LAPSE | WARNING |
| 11 | BLIND SPOT INDICATOR | WARN SOONER | PROTECT FOR DRIVER'S ATTENTION LAPSE | WARNING |
| 12 | LANE KEEP ASSIST | DISABLE FUNCTION | PROTECT FOR DRIVER'S ATTENTION LAPSE | WARNING |
| 13 | NAVIGATION SYSTEM | DISABLE FUNCTION | PROTECT FOR DRIVER'S ATTENTION LAPSE | WARNING |
| 14 | ELECTRONIC POWER STEERING | DECREASE ASSISTANCE | SUPPLEMENT DRIVER'S ALERTNESS | CONTROL |
| 15 | VISUAL DEVICES | PROVIDE VISUAL ALERT | SUPPLEMENT DRIVER'S ALERTNESS | WARNING |
| 16 | CLIMATE CONTROL | MODIFY CABIN TEMPERATURE | SUPPLEMENT DRIVER'S ALERTNESS | WARNING |
| 17 | AUDIO DEVICES | PROVIDE AUDIBLE ALERT | SUPPLEMENT DRIVER'S ALERTNESS | WARNING |
| 18 | ELECTRONIC PRETENSIONING SYSTEM | PROVIDE TACTILE FEEDBACK | SUPPLEMENT DRIVER'S ALERTNESS | WARNING |
| 19 | TACTILE DEVICES | PROVIDE TACTILE FEEDBACK | SUPPLEMENT DRIVER'S ALERTNESS | WARNING |

FIG. 5

SYSTEM AND METHOD FOR RESPONDING TO DRIVER BEHAVIOR

BACKGROUND

The current embodiment relates to motor vehicles and in particular to a system and method for responding to driver behavior.

Motor vehicles are operated by drivers in various conditions. Lack of sleep, monotonous road conditions, use of items, or health-related conditions can increase the likelihood that a driver may become drowsy or inattentive while driving. When drowsy or inattentive drivers may have delayed reaction times. A drowsy driver also has an increased likelihood of falling asleep at the wheel, which can cause potential harm to the driver, other vehicle occupants and occupants in nearby vehicles or pedestrians.

SUMMARY

In one aspect, a method of controlling one or more vehicle systems in a motor vehicle includes receiving monitoring information, determining if a driver is drowsy and modifying the control of one or more vehicle systems when the driver is drowsy.

In another aspect, a method of controlling a vehicle system in a motor vehicle includes receiving monitoring information, determining a level of drowsiness and modifying the control of the vehicle system when the driver is drowsy according to the level of drowsiness.

In another aspect, a method of controlling a vehicle system in a motor vehicle includes receiving information from a sensor, where the sensor is capable of detecting information about the autonomic nervous system of a driver. The method also includes determining if the driver is drowsy and modifying the control of the vehicle system when the driver is drowsy.

In another aspect, a method of controlling a vehicle system in a motor vehicle includes receiving monitoring information and determining a body state index for a driver, where the body state index characterizes drowsiness. The method also includes determining a control parameter using the body state index and operating a vehicle system using the control parameter.

Other systems, methods, features and advantages will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and detailed description. The components in the figures are not necessarily to scale, emphasis instead being placed upon illustrating the principles of the embodiments. Moreover, in the figures, like reference numerals designate corresponding parts throughout the different views.

FIG. 5 is a table showing the impact of a response system on various vehicle systems;

DETAILED DESCRIPTION

Figure 1:
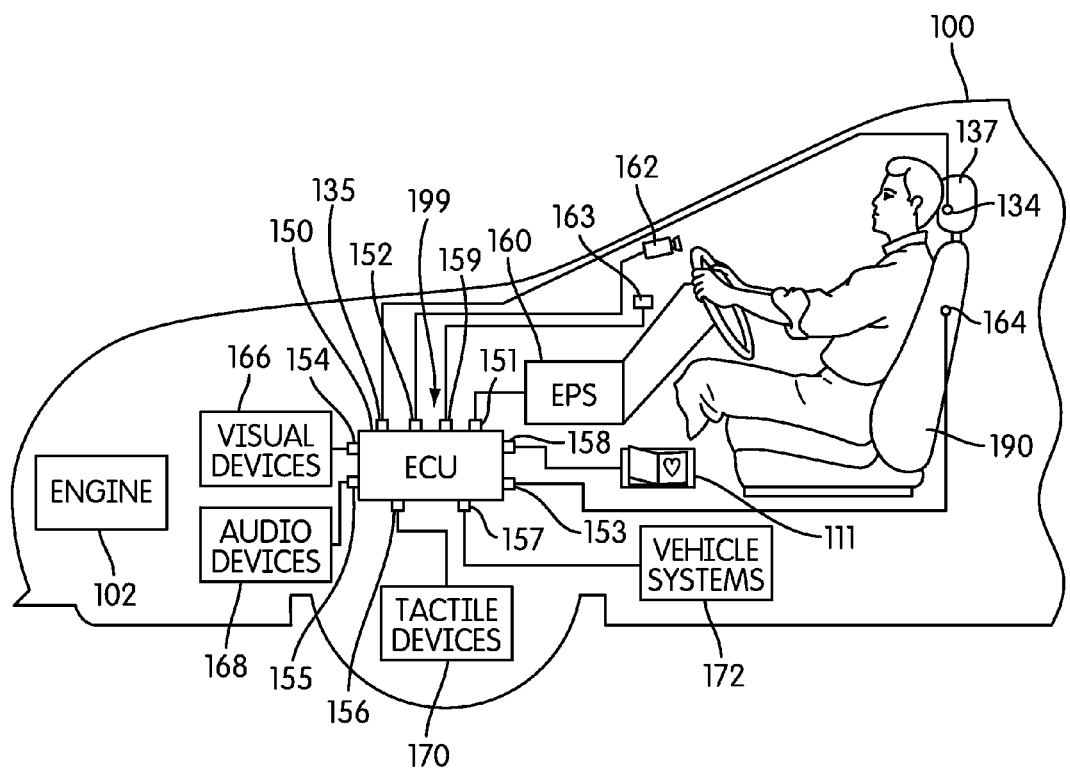
FIG. 1 is a schematic view of an embodiment of various components and systems for a motor vehicle.

FIG. 1 is a schematic view of an embodiment of various components for a motor vehicle 100. The term "motor vehicle" as used throughout this detailed description and in the claims refers to any moving vehicle that is capable of carrying one or more human occupants and is powered by any form of energy. The term "motor vehicle" includes, but is not limited to: cars, trucks, vans, minivans, SUVs, motorcycles, scooters, boats, personal watercraft, and aircraft.

In some cases, a motor vehicle includes one or more engines. The term "engine" as used throughout the specification and claims refers to any device or machine that is capable of converting energy. In some cases, potential energy is converted to kinetic energy. For example, energy conversion can include a situation where the chemical potential energy of a fuel or fuel cell is converted into rotational kinetic energy or where electrical potential energy is converted into rotational kinetic energy. Engines can also include provisions for converting kinetic energy into potential energy. For example, some engines include regenerative braking systems where kinetic energy from a drive train is converted into potential energy. Engines can also include devices that convert solar or nuclear energy into another form of energy. Some examples of engines include, but are not limited to: internal combustion engines, electric motors, solar energy converters, turbines, nuclear power plants, and hybrid systems that combine two or more different types of energy conversion processes.

For purposes of clarity, only some components of motor vehicle 100 are shown in the current embodiment. Furthermore, it will be understood that in other embodiments some of the components may be optional. Additionally, it will be understood that in other embodiments, any other arrangements of the components illustrated here can be used for powering motor vehicle 100.

Generally, motor vehicle 100 may be propelled by any power source. In some embodiments, motor vehicle 100 may be configured as a hybrid vehicle that uses two or more power sources. In other embodiments, motor vehicle 100 may use a single power source, such as an engine.

In one embodiment, motor vehicle 100 can include engine 102. Generally, the number of cylinders in engine 102 could vary. In some cases, engine 102 could include six cylinders. In some cases, engine 102 could be a three cylinder, four cylinder or eight cylinder engine. In still other cases, engine 102 could have any other number of cylinders.

In some embodiments, motor vehicle 100 may include provisions for communicating, and in some cases controlling, the various components associated with engine 102 and/or other systems of motor vehicle 100. In some embodiments, motor vehicle 100 may include a computer or similar device. In the current embodiment, motor vehicle 100 may include electronic control unit 150, hereby referred to as ECU 150. In one embodiment, ECU 150 may be configured to communicate with, and/or control, various components of motor vehicle 100.

ECU 150 may include a microprocessor, RAM, ROM, and software all serving to monitor and supervise various parameters of the engine, as well as other components or systems of motor vehicle 100. For example, ECU 150 is capable of receiving signals from numerous sensors, devices, and systems located in the engine. The output of various devices is sent to ECU 150 where the device signals may be stored in an electronic storage, such as RAM. Both current and electronically stored signals may be processed by a central processing unit (CPU) in accordance with software stored in an electronic memory, such as ROM.

ECU 150 may include a number of ports that facilitate the input and output of information and power. The term "port" as used throughout this detailed description and in the claims refers to any interface or shared boundary between two conductors. In some cases, ports can facilitate the insertion and removal of conductors. Examples of these types of ports include mechanical connectors. In other cases, ports are interfaces that generally do not provide easy insertion or removal. Examples of these types of ports include soldering or electric traces on circuit boards.

All of the following ports and provisions associated with ECU 150 are optional. Some embodiments may include a given port or provision, while others may exclude it. The following description discloses many of the possible ports and provisions that can be used, however, it should be kept in mind that not every port or provision must be used or included in a given embodiment.

In some embodiments, ECU 150 can include provisions for communicating and/or controlling various systems associated with engine 102. In one embodiment, ECU 150 can include port 151 for receiving various kinds of steering information. In some cases, ECU 150 may communicate with electronic power steering system 160, also referred to as EPS 160, through port 151. EPS 160 may comprise various components and devices utilized for providing steering assistance. In some cases, for example, EPS 160 may include an assist motor as well as other provisions for providing steering assistance to a driver. In addition, EPS 160 could be associated with various sensors including torque sensors, steering angle sensors as well as other kinds of sensors. Examples of electronic power steering systems are disclosed in Kobayashi, U.S. Pat. No. 7,497,471, filed Feb. 27, 2006 as well as Kobayashi, U.S. Pat. No. 7,497,299, filed Feb. 27, 2006, the entirety of both being hereby incorporated by reference.

In some embodiments, ECU 150 can include provisions for receiving various kinds of optical information. In one embodiment, ECU 150 can include port 152 for receiving information from one or more optical sensing devices, such as optical sensing device 162. Optical sensing device 162 could be any kind of optical device including a digital camera, video camera, infrared sensor, laser sensor, as well as any other device capable of detecting optical information. In one embodiment, optical sensing device 162 could be a video camera. In addition, in some cases, ECU 150 could include port 159 for communicating with thermal sensing device 163. Thermal sensing device 163 may be configured to detect thermal information. In some cases, thermal sensing device 163 and optical sensing device 162 could be combined into a single sensor.

Generally, one or more optical sensing devices and/or thermal sensing devices could be associated with any portion of a motor vehicle. In some cases, an optical sensing device could be mounted to the roof of a vehicle cabin. In other cases, an optical sensing device could be mounted in a vehicle dashboard. Moreover, in some cases, multiple optical sensing devices could be installed inside a motor vehicle to provide viewpoints of a driver or occupant from multiple different angles. In one embodiment, optical sensing device 162 may be installed in a portion of motor vehicle 100 so that optical sensing device 162 can capture images of the face and/or head of a driver or occupant. Similarly, thermal sensing device 163 could be located in any portion of motor vehicle 100 including a dashboard, roof or in any other portion. Thermal sensing device 163 may also be located so as to provide a view of the face and/or head of a driver.

In some embodiments, ECU 150 can include provisions for receiving information about the location of a driver's head. In one embodiment, ECU 150 can include port 135 for receiving information related to the distance between a driver's head and headrest 137. In some cases, this information can be received from proximity sensor 134. Proximity sensor 134 could be any type of sensor configured to detect the distance between the driver's head and headrest 137. In some cases, proximity sensor 134 could be a capacitor. In other cases, proximity sensor 134 could be a laser sensing device. In still other cases, any other types of proximity sensors known in the art could be used for proximity sensor 134. Moreover, in other embodiments, proximity sensor 134 could be used to detect the distance between any part of the driver and any portion of motor vehicle 100 including, but not limited to: a headrest, a seat, a steering wheel, a roof or ceiling, a driver side door, a dashboard, a central console as well as any other portion of motor vehicle 100.

In some embodiments, ECU 150 can include provisions for receiving information about the biological state of a driver. For example, ECU 150 could receive information related to the autonomic nervous system (or visceral nervous system) of a driver. In one embodiment, ECU 150 may include port 153 for receiving information about the state of a driver from bio-monitoring sensor 164. Examples of different information about a driver that could be received from bio-monitoring sensor 164 include, but are not limited to: heart information, such as, heart rate, blood pressure, oxygen content, etc., brain information, such as, electroencephalogram (EEG) measurements, functional near infrared spectroscopy (fNIRS), functional magnetic resonance imaging (fMRI), etc, digestion information, respiration rate information, salivation information, perspiration information, pupil dilation information, as well as other kinds of information related to the autonomic nervous system or other biological systems of the driver.

Generally, a bio-monitoring sensor could be disposed in any portion of a motor vehicle. In some cases, a bio-monitoring sensor could be disposed in a location proximate to a driver. For example, in one embodiment, bio-monitoring sensor 164 could be located within or on the surface of driver seat 190. In other embodiments, however, bio-monitoring sensor 164 could be located in any other portion of motor vehicle 100, including, but not limited to: a steering wheel, a headrest, an armrest, dashboard, rear-view mirror as well as any other location. Moreover, in some cases, bio-monitoring sensor 164 may be a portable sensor that is worn by a driver, associated with a portable device located in proximity to the driver, such as a smart phone or similar device or associated with an article of clothing worn by the driver.

In some embodiments, ECU 150 can include provisions for communicating with and/or controlling various visual devices. Visual devices include any devices that are capable of displaying information in a visual manner. These devices can include lights (such as dashboard lights, cabin lights, etc.), visual indicators, video screens (such as a navigation screen or touch screen), as well as any other visual devices. In one embodiment, ECU 150 includes port 154 for communicating with visual devices 166.

In some embodiments, ECU 150 can include provisions for communicating with and/or controlling various audio devices. Audio devices include any devices that are capable of providing information in an audible manner. These devices can include speakers as well as any of the systems associated with speakers such as radios, DVD players, CD players, cassette players, MP3 players, navigation systems as well as any other systems that provide audio information. In one embodiment, ECU 150 can include port 155 for communicating with audio devices 168. Moreover, audio devices 168 could be speakers in some cases, while in other cases audio devices 168 could include any systems that are capable of providing audio information to speakers that can be heard by a driver.

In some embodiments, ECU 150 can include provisions for communicating with and/or controlling various tactile devices. The term "tactile device" as used throughout this detailed description and in the claims refers to any device that is capable of delivering tactile stimulation to a driver or occupant. For example, a tactile device can include any device that vibrates or otherwise moves in a manner that can be sensed by a driver. Tactile devices could be disposed in any portion of a vehicle. In some cases, a tactile device could be located in a steering wheel to provide tactile feedback to a driver. In other cases, a tactile device could be located in a vehicle seat, to provide tactile feedback or to help relax a driver. In one embodiment, ECU 150 can include port 156 for communicating and/or controlling tactile devices 170.

In some embodiments, ECU 150 may include provisions for receiving input from a user. For example, in some embodiments, ECU 150 can include port 158 for receiving information from user input device 111. In some cases, user input device 111 could comprise one or more buttons, switches, a touch screen, touch pad, dial, pointer or any other type of input device. For example, in one embodiment, input device 111 could be a keyboard or keypad. In another embodiment, input device 111 could be a touch screen. In one embodiment, input device 111 could be an ON/OFF switch. In some cases, input device 111 could be used to turn on or off any body state monitoring devices associated with the vehicle or driver. For example, in an embodiment where an optical sensor is used to detect body state information, input device 111 could be used to switch this type of monitoring on or off. In embodiments using multiple monitoring devices, input device 111 could be used to simultaneously turn on or off all the different types of monitoring associated with these monitoring devices. In other embodiments, input device 111 could be used to selectively turn on or off some monitoring devices but not others.

In some embodiments, ECU 150 may include ports for communicating with and/or controlling various different engine components or systems. Examples of different engine components or systems include, but are not limited to: fuel injectors, spark plugs, electronically controlled valves, a throttle, as well as other systems or components utilized for the operation of engine 102.

It will be understood that only some components of motor vehicle 100 are shown in the current embodiment. In other embodiments, additional components could be included, while some of the components shown here could be optional. Moreover, ECU 150 could include additional ports for communicating with various other systems, sensors or components of motor vehicle 100. As an example, in some cases, ECU 150 could be in electrical communication with various sensors for detecting various operating parameters of motor vehicle 100, including but not limited to: vehicle speed, vehicle location, yaw rate, lateral g forces, fuel level, fuel composition, various diagnostic parameters as well as any other vehicle operating parameters and/or environmental parameters (such as ambient temperature, pressure, elevation, etc.).

In some embodiments, ECU 150 can include provisions for communicating with and/or controlling various different vehicle systems. Vehicle systems include any automatic or manual systems that may be used to enhance the driving experience and/or enhance safety. In one embodiment, ECU 150 can include port 157 for communicating with and/or controlling vehicle systems 172. For purposes of illustration, a single port is shown in the current embodiment for communicating with vehicle systems 172. However, it will be understood that in some embodiments, more than one port can be used. For example, in some cases, a separate port may be used for communicating with each separate vehicle system of vehicle systems 172. Moreover, in embodiments where ECU 150 comprises part of the vehicle system, ECU 150 can include additional ports for communicating with and/or controlling various different components or devices of a vehicle system.

Figure 2:
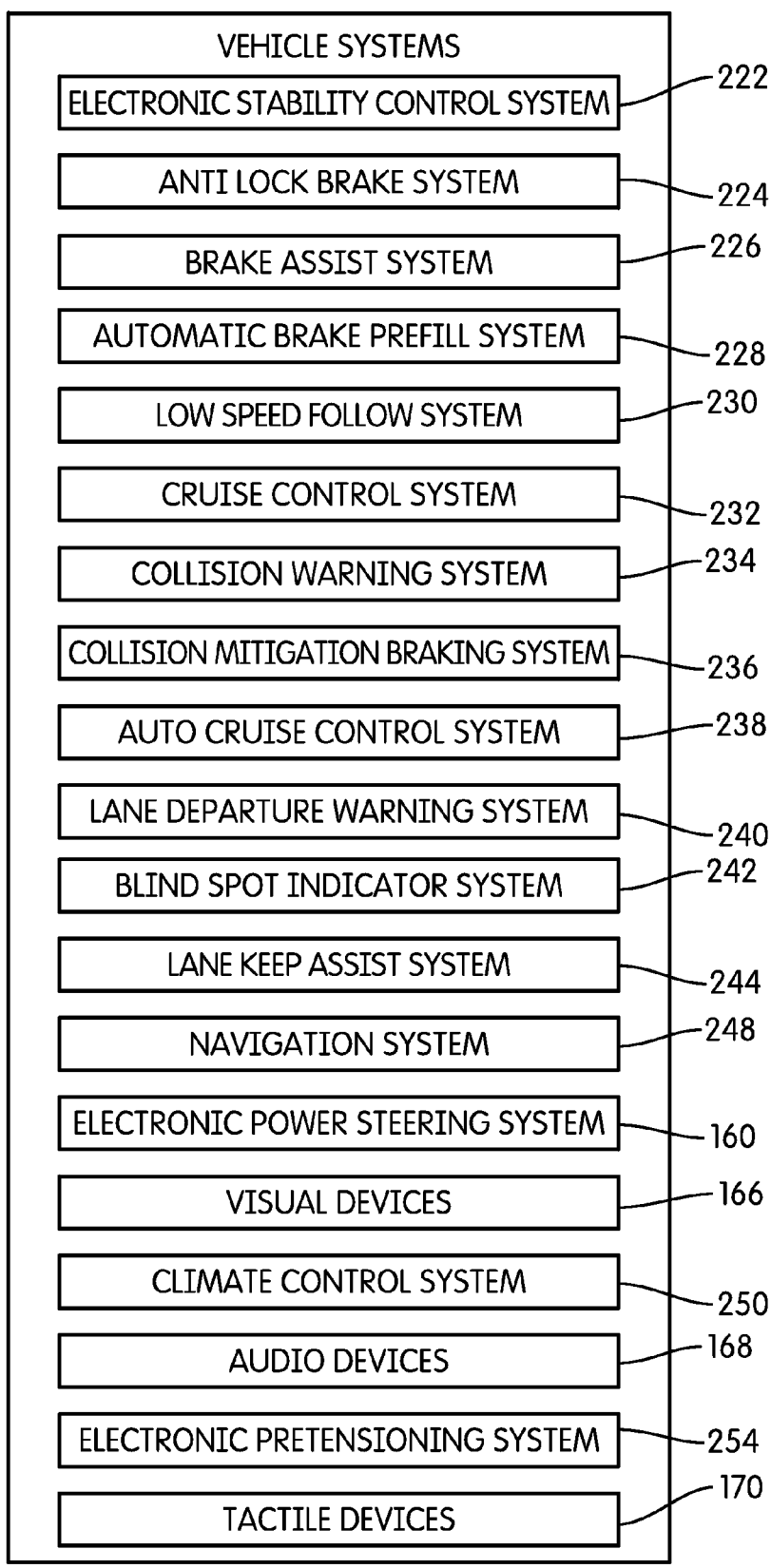
FIG. 2 is a schematic view of an embodiment of various different vehicle systems.

Examples of different vehicle systems 172 are illustrated in FIG. 2. It should be understood that the systems shown in FIG. 2 are only intended to be exemplary and in some cases some other additional systems may be included. In other cases, some of the systems may be optional and not included in all embodiments.

Motor vehicle 100 can include electronic stability control system 222 (also referred to as ESC system 222). ESC system 222 can include provisions for maintaining the stability of motor vehicle 100. In some cases, ESC system 222 may monitor the yaw rate and/or lateral g acceleration of motor vehicle 100 to help improve traction and stability. ESC system 222 may actuate one or more brakes automatically to help improve traction. An example of an electronic stability control system is disclosed in Ellis et al., U.S. Publication No. 2011/0231052, the entirety of which is hereby incorporated by reference. In one embodiment, the electronic stability control system may be a vehicle stability system.

In some embodiments, motor vehicle 100 can include antilock brake system 224 (also referred to as ABS system 224). ABS system 224 can include various different components such as a speed sensor, a pump for applying pressure to the brake lines, valves for removing pressure from the brake lines, and a controller. In some cases, a dedicated ABS controller may be used. In other cases, ECU 150 can function as an ABS controller. Examples of antilock braking systems are known in the art. One example is disclosed in Ingaki, et al., U.S. Pat. No. 6,908,161, filed Nov. 18, 2003, the entirety of which is hereby incorporated by reference. Using ABS system 224 may help improve traction in motor vehicle 100 by preventing the wheels from locking up during braking.

Motor vehicle 100 can include brake assist system 226. Brake assist system 226 may be any system that helps to reduce the force required by a driver to depress a brake pedal. In some cases, brake assist system 226 may be activated for older drivers or any other drivers who may need assistance with braking. An example of a brake assist system can be found in Wakabayashi et al., U.S. Pat. No. 6,309,029, filed Nov. 17, 1999, the entirety of which is hereby incorporated by reference.

In some embodiments, motor vehicle 100 can include automatic brake prefill system 228 (also referred to as ABP system 228). ABP system 228 includes provisions for prefilling one or more brake lines with brake fluid prior to a collision. This may help increase the reaction time of the braking system as the driver depresses the brake pedal. Examples of automatic brake prefill systems are known in the art. One example is disclosed in Bitz, U.S. Pat. No. 7,806,486, the entirety of which is hereby incorporated by reference.

In some embodiments, motor vehicle 100 can include low speed follow system 230 (also referred to as LSF system 230). LSF system 230 includes provisions for automatically following a preceding vehicle at a set distance or range of distances. This may reduce the need for the driver to constantly press and depress the acceleration pedal in slow traffic situations. LSF system 230 may include components for monitoring the relative position of a preceding vehicle (for example, using remote sensing devices such as lidar or radar). In some cases, LSF system 230 may include provisions for communicating with any preceding vehicles for determining the GPS positions and/or speeds of the vehicles. Examples of low speed follow systems are known in the art. One example is disclosed in Arai, U.S. Pat. No. 7,337,056, filed Mar. 23, 2005, the entirety of which is hereby incorporated by reference. Another example is disclosed in Higashimata et al., U.S. Pat. No. 6,292,737, filed May 19, 2000, the entirety of which is hereby disclosed by reference.

Motor vehicle 100 can include cruise control system 232. Cruise control systems are well known in the art and allow a user to set a cruising speed that is automatically maintained by a vehicle control system. For example, while traveling on a highway, a driver may set the cruising speed to 55 mph. Cruise control system 232 may maintain the vehicle speed at approximately 55 mph automatically, until the driver depresses the brake pedal or otherwise deactivates the cruising function.

Motor vehicle 100 can include collision warning system 234. In some cases, collision warning system 234 may include provisions for warning a driver of any potential collision threats with one or more vehicles. For example, a collision warning system can warn a driver when another vehicle is passing through an intersection as motor vehicle 100 approaches the same intersection. Examples of collision warning systems are disclosed in Mochizuki, U.S. Publication No. 2012/0068859, filed Sep. 20, 2010, and Mochizuki et al., U.S. Publication No. 2012/0025965, the entirety of both being hereby incorporated by reference. In one embodiment, collision warning system 234 could be a forward collision warning system.

Motor vehicle 100 can include collision mitigation braking system 236 (also referred to as CMBS 236). CMBS 236 may include provisions for monitoring vehicle operating conditions (including target vehicles and objects in the environment of the vehicle) and automatically applying various stages of warning and/or control to mitigate collisions. For example, in some cases, CMBS 236 may monitor forward vehicles using a radar or other type of remote sensing device. If motor vehicle 100 gets too close to a forward vehicle, CMBS 236 could enter a first warning stage. During the first warning stage, a visual and/or audible warning may be provided to warn the driver. If motor vehicle 100 continues to get closer to the forward vehicle, CMBS 236 could enter a second warning stage. During the second warning stage, CMBS 236 could apply automatic seatbelt pretensioning. In some cases, visual and/or audible warnings could continue throughout the second warning stage. Moreover, in some cases, during the second stage automatic braking could also be activated to help reduce the vehicle speed. In some cases, a third stage of operation for CMBS 236 may involve braking the vehicle and tightening a seatbelt automatically in situations where a collision is very likely. An example of such a system is disclosed in Bond, et al., U.S. Pat. No. 6,607,255, and filed Jan. 17, 2002, the entirety of which is hereby incorporated by reference. The term collision mitigation braking system as used throughout this detailed description and in the claims refers to any system that is capable of sensing potential collision threats and providing various types of warning responses as well as automated braking in response to potential collisions.

Motor vehicle 100 can include auto cruise control system 238 (also referred to as ACC system 238). In some cases, ACC system 238 may include provisions for automatically controlling the vehicle to maintain a predetermined following distance behind a preceding vehicle or to prevent a vehicle from getting closer than a predetermined distance to a preceding vehicle. ACC system 238 may include components for monitoring the relative position of a preceding vehicle (for example, using remote sensing devices such as lidar or radar). In some cases, ACC system 238 may include provisions for communicating with any preceding vehicles for determining the GPS positions and/or speeds of the vehicles. An example of an auto cruise control system is disclosed in Arai et al., U.S. Pat. No. 7,280,903, filed Aug. 31, 2005, the entirety of which is hereby incorporated by reference.

Motor vehicle 100 can include lane departure warning system 240 (also referred to as LDW system 240). LDW system 240 may determine when a driver is deviating from a lane and provide a warning signal to alert the driver. Examples of lane departure warning systems can be found in Tanida et al., U.S. Pat. No. 8,063,754, the entirety of which is hereby incorporated by reference.

Motor vehicle 100 can include blind spot indicator system 242. Blind spot indicator system 242 can include provisions for helping to monitor the blind spot of a driver. In some cases, blind spot indicator system 242 can include provisions to warn a driver if a vehicle is located within a blind spot. Any known systems for detecting objects traveling around a vehicle can be used.

In some embodiments, motor vehicle 100 can include lane keep assist system 244. Lane keep assist system 244 can include provisions for helping a driver to stay in the current lane. In some cases, lane keep assist system 244 can warn a driver if motor vehicle 100 is unintentionally drifting into another lane. Also, in some cases, lane keep assist system 244 may provide assisting control to maintain a vehicle in a predetermined lane. An example of a lane keep assist system is disclosed in Nishikawa et al., U.S. Pat. No. 6,092,619, filed May 7, 1997, the entirety of which is hereby incorporated by reference.

In some embodiments, motor vehicle 100 could include navigation system 248. Navigation system 248 could be any system capable of receiving, sending and/or processing navigation information. The term "navigation information" refers to any information that can be used to assist in determining a location or providing directions to a location. Some examples of navigation information include street addresses, street names, street or address numbers, apartment or suite numbers, intersection information, points of interest, parks, any political or geographical subdivision including town, township, province, prefecture, city, state, district, ZIP or postal code, and country. Navigation information can also include commercial information including business and restaurant names, commercial districts, shopping centers, and parking facilities. In some cases, the navigation system could be integrated into the motor vehicle. In other cases, the navigation system could be a portable or stand-alone navigation system.

Motor vehicle 100 can include climate control system 250. Climate control system 250 may be any type of system used for controlling the temperature or other ambient conditions in motor vehicle 100. In some cases, climate control system 250 may comprise a heating, ventilation and air conditioning system as well as an electronic controller for operating the HVAC system. In some embodiments, climate control system 250 can include a separate dedicated controller. In other embodiments, ECU 150 may function as a controller for climate control system 250. Any kind of climate control system known in the art may be used.

Motor vehicle 100 can include electronic pretensioning system 254 (also referred to as EPT system 254). EPT system 254 may be used with a seatbelt for a vehicle. EPT system 254 can include provisions for automatically tightening, or tensioning, the seatbelt. In some cases, EPT system 254 may automatically pretension the seatbelt prior to a collision. An example of an electronic pretensioning system is disclosed in Masuda et al., U.S. Pat. No. 6,164,700, filed Apr. 20, 1999, the entirety of which is hereby incorporated by reference.

Additionally, vehicle systems 172 could incorporate electronic power steering system 160, visual devices 166, audio devices 168 and tactile devices 170, as well as any other kinds of devices, components or systems used with vehicles.

It will be understood that each of these vehicle systems may be standalone systems or may be integrated with ECU 150. For example, in some cases, ECU 150 may operate as a controller for various components of one or more vehicle systems. In other cases, some systems may comprise separate dedicated controllers that communicate with ECU 150 through one or more ports.

Figure 3:
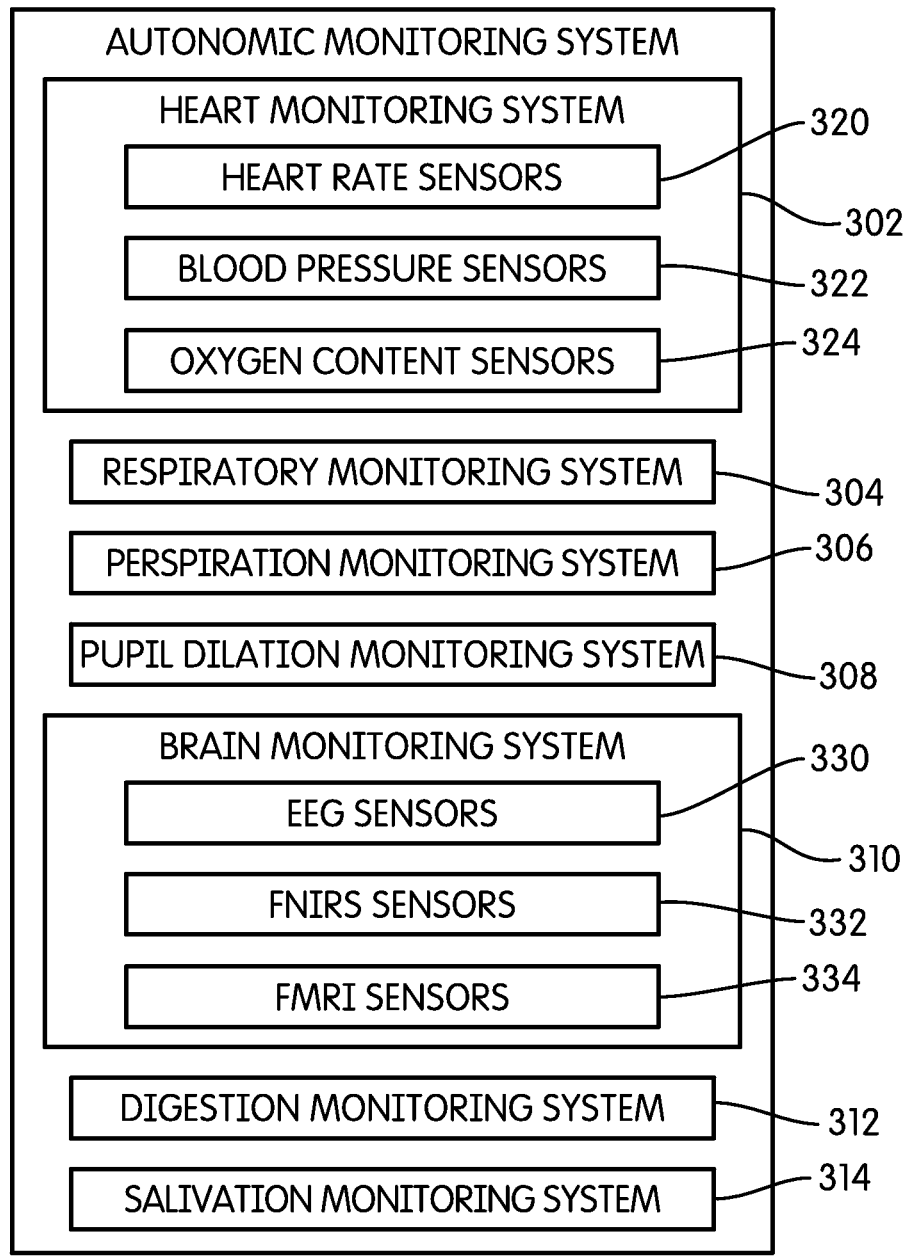
FIG. 3 is a schematic view of an embodiment of various different autonomic monitoring systems.

FIG. 3 illustrates an embodiment of various autonomic monitoring systems that could be associated with motor vehicle 100. These autonomic monitoring systems could include one or more bio-monitoring sensors 164. For example, in some embodiments, motor vehicle 100 could include heart monitoring system 302. Heart monitoring system 302 could include any devices or systems for monitoring the heart information of a driver. In some cases, heart monitoring system 302 could include heart rate sensors 320, blood pressure sensors 322 and oxygen content sensors 324 as well as any other kinds of sensors for detecting heart information and/or cardiovascular information. Moreover, sensors for detecting heart information could be disposed in any locations within motor vehicle 100. For example, heart monitoring system 302 could include sensors disposed in a steering wheel, seat, armrest or other component that detect the heart information of a driver. Motor vehicle 100 could also include respiratory monitoring system 304. Respiratory monitoring system 304 could include any devices or systems for monitoring the respiratory function (e.g. breathing) of a driver. For example, respiratory monitoring system 304 could include sensors disposed in a seat for detecting when a driver inhales and exhales. In some embodiments, motor vehicle 100 could include perspiration monitoring system 306. Perspiration monitoring system 306 may include any devices or systems for sensing perspiration or sweat from a driver. In some embodiments, motor vehicle 100 could include pupil dilation monitoring system 308 for sensing the amount of pupil dilation, or pupil size, in a driver. In some cases, pupil dilation monitoring system 308 could include one or more optical sensing devices.

Additionally, in some embodiments, motor vehicle 100 may include brain monitoring system 310 for monitoring various kinds of brain information. In some cases, brain monitoring system 310 could include electroencephalogram (EEG) sensors 330, functional near infrared spectroscopy (fNIRS) sensors 332, functional magnetic resonance imaging (fMRI) sensors 334 as well as other kinds of sensors capable of detecting brain information. Such sensors could be located in any portion of motor vehicle 100. In some cases, sensors associated with brain monitoring system 310 could be disposed in a headrest. In other cases, sensors could be disposed in the roof of motor vehicle 100. In still other cases, sensors could be disposed in any other locations.

In some embodiments, motor vehicle 100 may include digestion monitoring system 312. In other embodiments, motor vehicle 100 may include salivation monitoring system 314. In some cases, monitoring digestion and/or salivation could also help in determining if a driver is drowsy. Sensors for monitoring digestion information and/or salivation information can be disposed in any portion of a vehicle. In some cases, sensors could be disposed on a portable device used or worn by a driver.

It will be understood that each of the monitoring systems discussed above could be associated with one or more sensors or other devices. In some cases, the sensors could be disposed in one or more portions of motor vehicle 100. For example, the sensors could be integrated into a seat, door, dashboard, steering wheel, center console, roof or any other portion of motor vehicle 100. In other cases, however, the sensors could be portable sensors worn by a driver, integrated into a portable device carried by the driver or integrated into an article of clothing worn by the driver.

For purposes of convenience, various components discussed above and shown in FIGS. 1 through 3 may be referred to as driver behavior response system 199, also referred to as simply response system 199. In some cases, response system 199 comprises ECU 150 as well as one or more sensors, components, devices or systems discussed above. In some cases, response system 199 may receive input from various devices related to the behavior of a driver. In some cases, this information may be referred to as "monitoring information". In some cases, monitoring information could be received from a monitoring system, which may include any system configured to provide monitoring information such as optical devices, thermal devices, autonomic monitoring devices as well as any other kinds of devices, sensors or systems. In some cases, monitoring information could be received directly from a vehicle system, rather than from a system or component designed for monitoring driver behavior. In some cases, monitoring information could be received from both a monitoring system and a vehicle system. Response system 199 may use this information to modify the operation of one or more vehicle systems 172. Moreover, it will be understood that in different embodiments, response system 199 could be used to control any other components or systems utilized for operating motor vehicle 100.

Response system 199 can include provisions for determining if a driver is drowsy based on biological information, including information related to the autonomic nervous system of the driver. For example, a response system could detect a drowsy condition for a driver by analyzing heart information, breathing rate information, brain information, perspiration information as well as any other kinds of autonomic information.

A motor vehicle can include provisions for assessing the behavior of a driver and automatically adjusting the operation of one or more vehicle systems in response to the behavior. Throughout this specification, drowsiness will be used as the example behavior being assessed; however, it should be understood that any driver behavior could be assessed, including but not limited to drowsy behavior, distracted behavior, impaired behavior and/or generally inattentive behavior. The assessment and adjustment discussed below may accommodate for the driver's slower reaction time, attention lapse and/or alertness. For example, in situations where a driver may be drowsy, the motor vehicle can include provisions for detecting that the driver is drowsy. Moreover, since drowsiness can increase the likelihood of hazardous driving situations, the motor vehicle can include provisions for modifying one or more vehicle systems automatically in order to mitigate against hazardous driving situations. In one embodiment, a driver behavior response system can receive information about the state of a driver and automatically adjust the operation of one or more vehicle systems.

The following detailed description discusses a variety of different methods for operating vehicle systems in response to driver behavior. In different embodiments, the various different steps of these processes may be accomplished by one or more different systems, devices or components. In some embodiments, some of the steps could be accomplished by a response system 199 of a motor vehicle. In some cases, some of the steps may be accomplished by an ECU 150 of a motor vehicle. In other embodiments, some of the steps could be accomplished by other components of a motor vehicle, including but not limited to, the vehicle systems 172. Moreover, for each process discussed below and illustrated in the Figures it will be understood that in some embodiments one or more of the steps could be optional.

Figure 4:
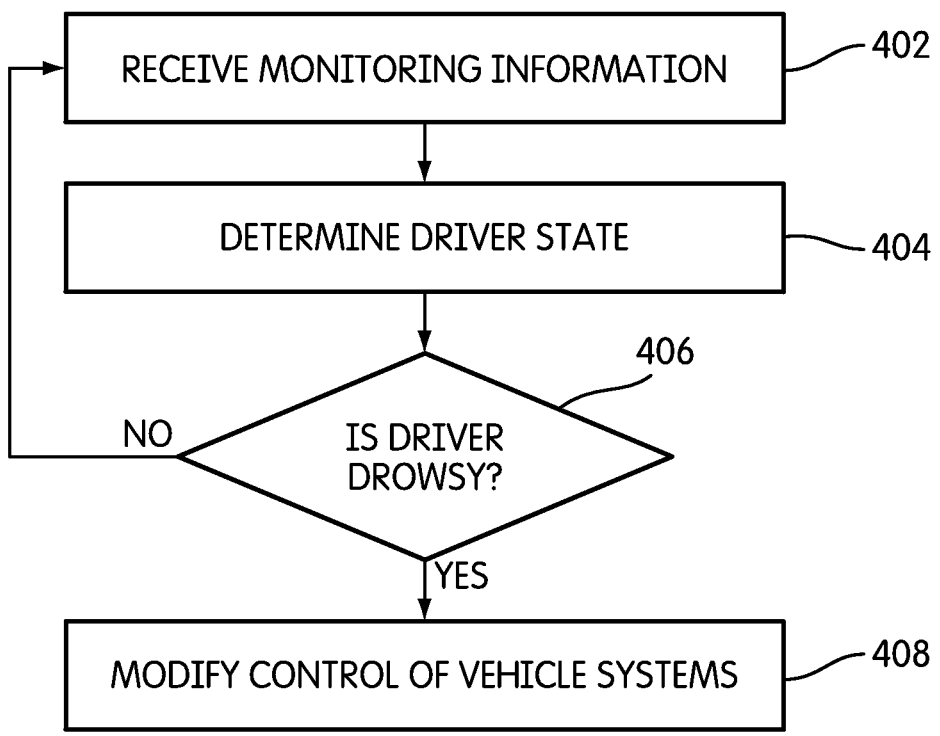
FIG. 4 is an embodiment of a process of controlling vehicle systems according to driver behavior.

FIG. 4 illustrates an embodiment of a process for controlling one or more vehicle systems in a motor vehicle depending on the state of the driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 402, response system 199 may receive monitoring information. In some cases, the monitoring information can be received from one or more sensors. In other cases, the monitoring information can be received from one or more autonomic monitoring systems. In still other cases, the monitoring information can be received from one or more vehicle systems. In still other cases, the monitoring information can be received from any other device of motor vehicle 100. In still other cases, the monitoring information can be received from any combination of sensors, monitoring systems, vehicles systems or other devices.

In step 404, response system 199 may determine the driver state. In some cases, the driver state may be normal or drowsy. In other cases, the driver state may range over three or more states ranging between normal and very drowsy (or even asleep). In this step, response system 199 may use any information received during step 402, including information from any kinds of sensors or systems. For example, in one embodiment, response system 199 may receive information from an optical sensing device that indicates the driver has closed his or her eyes for a substantial period of time. Other examples of determining the state of a driver are discussed in detail below.

In step 406, response system 199 may determine whether or not the driver is drowsy. If the driver is not drowsy, response system 199 may proceed back to step 402 to receive additional monitoring information. If, however, the driver is drowsy, response system 199 may proceed to step 408. In step 408, response system 199 may automatically modify the control of one or more vehicle systems, including any of the vehicle systems discussed above. By automatically modifying the control of one or more vehicle systems, response system 199 may help to avoid various hazardous situations that can be caused by a drowsy driver.

In some embodiments, a user may not want any vehicle systems modified or adjusted. In these cases, the user may switch input device 111, or a similar kind of input device, to the OFF position (see FIG. 1). This could have the effect of turning off all body state monitoring and would further prevent response system 199 from modifying the control of any vehicle systems. Moreover, response system 199 could be reactivated at any time by switching input device 111 to the ON position (see FIG. 1). In other embodiments, additional switches or buttons could be provided to turn on/off individual monitoring systems.

FIG. 5 is a table emphasizing the response system 199 impact on various vehicle systems due to changes in the driver's behavior, as well as the benefits to the driver for each change according to one embodiment. In particular, column 421 lists the various vehicle systems, which include many of the vehicle systems 172 discussed above and shown in FIG. 2. Column 422 describes how response system 199 impacts the operation of each vehicle system when the driver's behavior is such that the driver may be distracted, drowsy, less attentive and/or impaired. Column 423 describes the benefits for the response system impacts described in column 422. Column 424 describes the type of impact performed by response system 199 for each vehicle system. In particular, in column 424 the impact of response system 199 on each vehicle system is described as either "control" type or "warning" type. The control type indicates that the operation of a vehicle system is modified by the control system. The warning type indicates that the vehicle system is used to warn or otherwise alert a driver.

As indicated in FIG. 5, upon detecting that a driver is drowsy or otherwise inattentive, response system 199 may control the electronic stability control system 222, the anti-lock brake system 224, the brake assist system 226 and the brake pre-fill system 228 in a manner that compensates for the potentially slower reaction time of the driver. For example, in some cases, response system 199 may operate the electronic stability system 222 to improve steering precision and enhance stability. In some cases, response system 199 may operate the anti-lock brake system 224 so that the stopping distance is decreased. In some cases, response system 199 may control the brake assist system 226 so that an assisted braking force is applied sooner. In some cases, response system 199 may control the brake pre-fill system 228 so the brake lines are automatically pre-filled with brake fluid when a driver is drowsy. These actions may help to improve the steering precision and brake responsiveness when a driver is drowsy.

Additionally, upon detecting that a driver is drowsy or otherwise inattentive, response system 199 may control the low speed follow system 230, the cruise control system 232, the collision warning system 234, the collision mitigation braking system 236, the auto cruise control system 238, the lane departure warning system 240, the blind spot indicator system 242 and the lane keep assist system 244 to provide protection due to the driver's lapse of attention. For example, the low speed follow system 230, cruise control system 232 and lane keep assist system 244 could be disabled when the driver is drowsy to prevent unintended use of these systems. Likewise, the collision warning system 234, collision mitigation braking system 236, lane departure warning system 240 and blind spot indicator system 242 could warn a driver sooner about possible potential hazards. In some cases, the auto cruise control system 238 could be configured to increase the minimum gap distance between motor vehicle 100 and the preceding vehicle.

In some embodiments, upon detecting that a driver is drowsy or otherwise inattentive, response system 199 may control the electronic power steering system 160, visual devices 166, the climate control system 250 (such as HVAC), audio devices 168, the electronic pretensioning system 254 for a seatbelt and tactile devices 170 to supplement the driver's alertness. For example, the electronic power steering system 160 may be controlled to decrease power steering assistance. This requires the driver to apply more effort and can help improve awareness or alertness. Visual devices 166 and audio devices 168 may be used to provide visual feedback and audible feedback, respectively. Tactile devices 170 and the electronic pretensioning system 254 can be used to provide tactile feedback to a driver. Also, the climate control system 250 may be used to change the cabin or driver temperature to effect the drowsiness of the driver. For example, by changing the cabin temperature the driver may be made more alert.

The various systems listed in FIG. 5 are only intended to be exemplary and other embodiments could include additional vehicle systems that may be controlled by response system 199. Moreover, these systems are not limited to a single impact or function. Also, these systems are not limited to a single benefit. Instead, the impacts and benefits listed for each system are intended as examples. A detailed explanation of the control of many different vehicle systems is discussed in detail below and shown in the Figures.

A response system can include provisions for determining a level of drowsiness for a driver. The term "level of drowsiness" as used throughout this detailed description and in the claims refers to any numerical or other kind of value for distinguishing between two or more states of drowsiness. For example, in some cases, the level of drowsiness may be given as a percentage between 0% and 100%, where 0% refers to a driver that is totally alert and 100% refers to a driver that is fully drowsy or even asleep. In other cases, the level of drowsiness could be a value in the range between 1 and 10. In still other cases, the level of drowsiness may not be a numerical value, but could be associated with a given discrete state, such as "not drowsy", "slightly drowsy", "drowsy", "very drowsy" and "extremely drowsy". Moreover, the level of drowsiness could be a discrete value or a continuous value. In some cases, the level of drowsiness may be associated with a body state index, which is discussed in further detail below.

Figure 6:
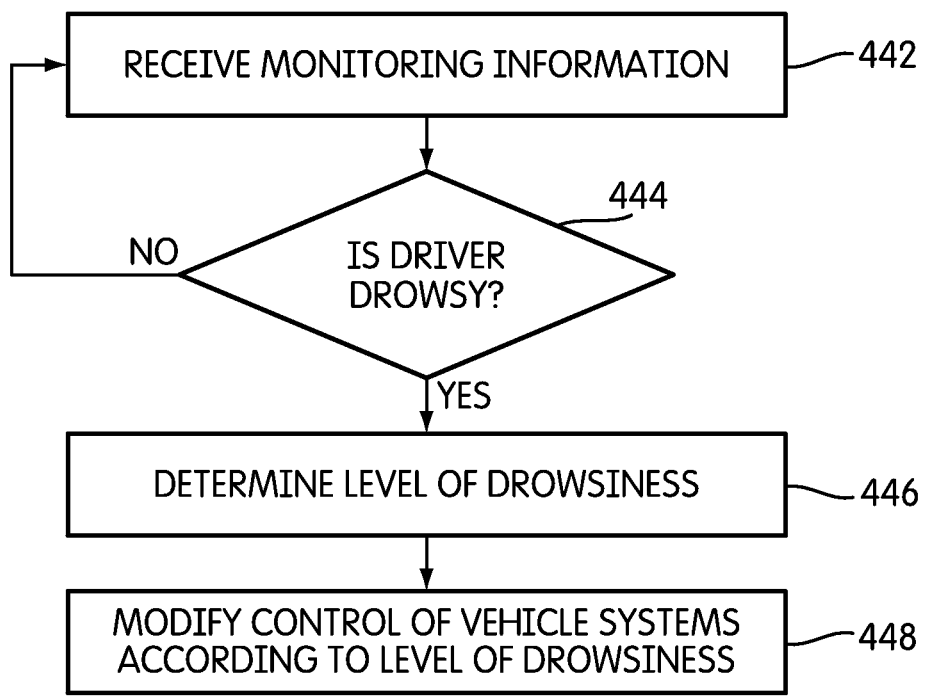
FIG. 6 is an embodiment of a process of determining a level of drowsiness and operating one or more vehicle systems.

FIG. 6 illustrates an embodiment of a process of modifying the operation of a vehicle system according to the level of drowsiness detected. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 442, response system 199 may receive monitoring information. In some cases, the monitoring information can be received from one or more sensors. In other cases, the monitoring information can be received from one or more autonomic monitoring systems. In still other cases, the monitoring information can be received from one or more vehicle systems. In still other cases, the monitoring information can be received from any other device of motor vehicle 100. In still other cases, the monitoring information can be received from any combination of sensors, monitoring systems, vehicles systems or other devices.

In step 444, response system 199 may determine if the driver is drowsy. If the driver is not drowsy, response system 199 may return back to step 442. If the driver is drowsy, response system 199 may proceed to step 446. In step 446, response system 199 may determine the level of drowsiness. As discussed above, the level of drowsiness could be represented by a numerical value or could be a discrete state labeled by a name or variable. In step 448, response system 199 may modify the control of one or more vehicle systems according to the level of drowsiness.

Examples of systems that can be modified according to the level of drowsiness include, but are not limited to: antilock brake system 224, automatic brake prefill system 228, brake assist system 226, auto cruise control system 238, electronic stability control system 222, collision warning system 234, lane keep assist system 244, blind spot indicator system 242, electronic pretensioning system 254 and climate control system 250. In addition, electronic power steering system 160 could be modified according to the level of drowsiness, as could visual devices 166, audio devices 168 and tactile devices 170. In some embodiments, the timing and/or intensity associated with various warning indicators (visual indicators, audible indicators, haptic indicators, etc.) could be modified according to the level of drowsiness. For example, in one embodiment, electronic pretensioning system 254 could increase or decrease the intensity and/or frequency of automatic seatbelt tightening to warn the driver at a level appropriate for the level of drowsiness.

As an example, when a driver is extremely drowsy, the antilock brake system 224 may be modified to achieve a shorter stopping distance than when a driver is somewhat drowsy. As another example, automatic brake prefill system 228 could adjust the amount of brake fluid delivered during a prefill or the timing of the prefill according to the level of drowsiness. Likewise, the level of brake assistance provided by brake assist system 226 could be varied according to the level of drowsiness, with assistance increased with drowsiness. Also, the headway distance for auto cruise control system 238 could be increased with the level of drowsiness. In addition, the error between the yaw rate and the steering yaw rate determined by electronic stability control system 222 could be decreased in proportion to the level of drowsiness. In some cases, collision warning system 234 and lane departure system 240 could provide earlier warnings to a drowsy driver, where the timing of the warnings is modified in proportion to the level of drowsiness. Likewise, the detection area size associated with blind spot indicator system 242 could be varied according to the level of drowsiness. In some cases, the strength of a warning pulse generated by electronic pretensioning system 254 may vary in proportion to the level of drowsiness. Also, climate control system 250 may vary the number of degrees that the temperature is changed according to the level of drowsiness. Moreover, the brightness of the lights activated by visual devices 166 when a driver is drowsy could be varied in proportion to the level of drowsiness. Also, the volume of sound generated by audio devices 168 could be varied in proportion to the level of drowsiness. In addition, the amount of vibration or tactile stimulation delivered by tactile devices 170 could be varied in proportion to the level of drowsiness. In some cases, the maximum speed at which low speed follow system 230 operates could be modified according to the level of drowsiness. Likewise, the on/off setting or the maximum speed at which cruise control system 232 can be set may be modified in proportion to the level of drowsiness. Additionally, the degree of power steering assistance provided by electronic power steering system 160 could be varied in proportion to the level of drowsiness. Also, the distance that the collision mitigation braking system begins to brake can be lengthened or the lane keep assist system could be modified so that the driver must provide more input to the system.

Figure 7:
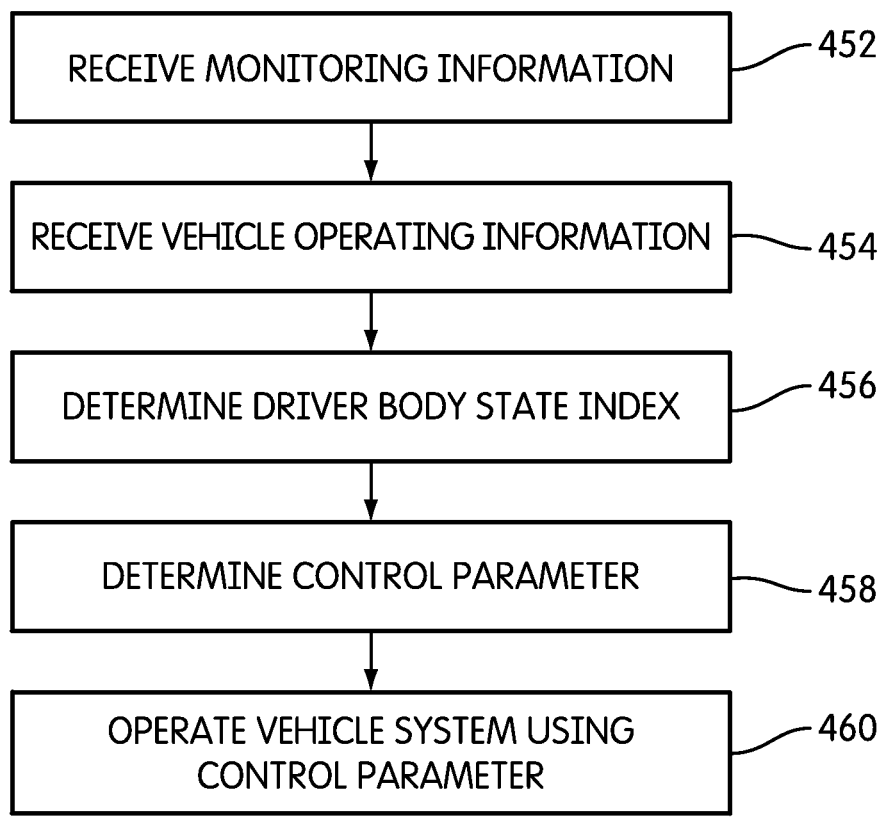
FIG. 7 is an embodiment of a process for operating a vehicle system using a control parameter.

FIG. 7 illustrates an embodiment of a process of modifying the operation of a vehicle system according to the level of drowsiness detected. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 452, response system 199 may receive monitoring information, as discussed above and with respect to step 442 of FIG. 6. In step 454, response system 199 can receive any kind of vehicle operating information from one or more vehicle systems. The type of operating information received during step 454 may vary according to the type of vehicle system involved. For example, if the current process is used for operating a brake assist system, the operating information received may be brake pressure, vehicle speed and other operating parameters related to a brake assist system. As another example, if the current process is used for operating an electronic stability control system, the operation information may include yaw rate, wheel speed information, steering angle, lateral G, longitudinal G, road friction information as well as any other information used for operating an electronic stability control system.

Next, in step 456, response system 199 can determine a body state index of the driver. The term "body state index" refers to a measure of the drowsiness of a driver. In some cases, the body state index could be given as a numerical value. In other cases, the body state index could be given as a non-numerical value. Moreover, the body state index may range from values associated with complete alertness to values associated with extreme drowsiness or even a state in which the driver is asleep. In one embodiment, the body state index could take on the values 1, 2, 3 and 4, where 1 is the least drowsy and 4 is the most drowsy. In another embodiment, the body state index could take on values from 1-10.

Generally, the body state index of the driver can be determined using any of the methods discussed throughout this detailed description for detecting driver behavior as it relates to drowsiness. In particular, the level of drowsiness may be detected by sensing different degrees of driver behavior. For example, as discussed below, drowsiness in a driver may be detected by sensing eyelid movement and/or head movement. In some cases, the degree of eyelid movement (the degree to which the eyes are open or closed) or the degree of head movement (how tilted the head is) could be used to determine the body state index. In other cases, the autonomic monitoring systems could be used to determine the body state index. In still other cases, the vehicle systems could be used to determine the body state index. For example, the degree of unusual steering behavior or the degree of lane departures may indicate a certain body state index.

In step 458, response system 199 may determine a control parameter. The term "control parameter" as used throughout this detailed description and in the claims refers to a parameter used by one or more vehicle systems. In some cases, a control parameter may be an operating parameter that is used to determine if a particular function should be activated for a given vehicle system. For example, in situations where an electronic stability control system is used, the control parameter may be a threshold error in the steering yaw rate that is used to determine if stability control should be activated. As another example, in situations where automatic cruise control is used, the control parameter may be a parameter used to determine if cruise control should be automatically turned off. Further examples of control parameters are discussed in detail below and include, but are not limited to: stability control activation thresholds, brake assist activation thresholds, blind spot monitoring zone thresholds, time to collision thresholds, road crossing thresholds, lane keep assist system status, low speed follow status, electronic power steering status, auto cruise control status as well as other control parameters.

In some cases, a control parameter can be determined using vehicle system information as well as the body state index determined during step 456. In other cases, only the body state index may be used to determine the control parameter. In still other cases, only the vehicle operating information may be used to determine the control parameter. Following step 458, during step 460, response system 199 may operate a vehicle system using the control parameter.

Figure 8:
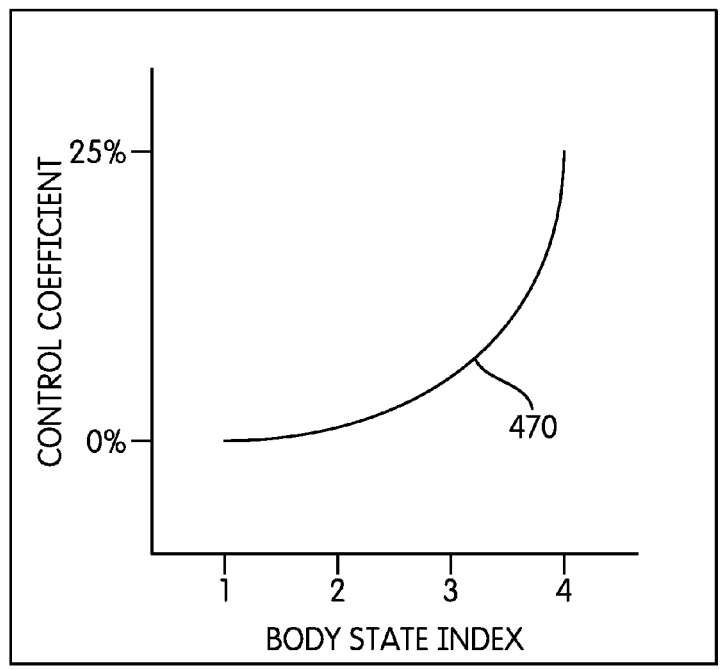
FIG. 8 is an embodiment of a relationship between body state index and a control coefficient.
Figure 9:
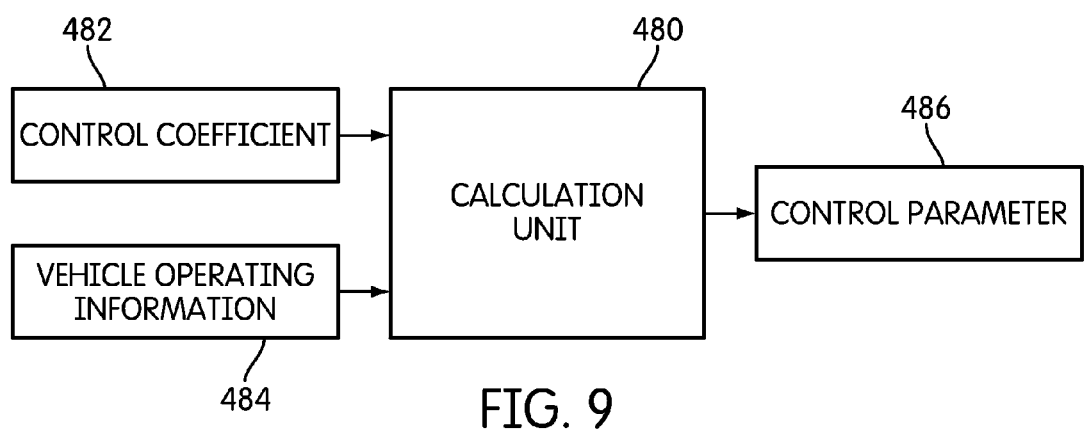
FIG. 9 is an embodiment of a calculation unit for determining a control parameter.

FIGS. 8 and 9 illustrate schematic views of a general method for determining a control parameter using the body state index of the driver as well as vehicle operating information. In particular, FIG. 8 illustrates a schematic view of how the body state index can be used to retrieve a control coefficient. A control coefficient may be any value used in determining a control parameter. In some cases, the control coefficient varies as a function of body state index and is used as an input for calculating the control parameter. Examples of control coefficients include, but are not limited to: electronic stability control system coefficients, brake assist coefficients, blind spot zone warning coefficients, warning intensity coefficients, forward collision warning coefficients, lane departure warning coefficients and lane keep assist coefficients. Some systems may not use a control coefficient to determine the control parameter. For example, in some cases, the control parameter can be determined directly from the body state index.

In one embodiment, the value of the control coefficient 470 increases from 0% to 25% as the body state index increases from 1 to 4. In some cases, the control coefficient may serve as a multiplicative factor for increasing or decreasing the value of a control parameter. For example, in some cases when the body state index is 4, the control coefficient may be used to increase the value of a control parameter by 25%. In other embodiments, the control coefficient could vary in any other manner. In some cases, the control coefficient could vary linearly as a function of body state index. In other cases, the control coefficient could vary in a nonlinear manner as a function of body state index. In still other cases, the control coefficient could vary between two or more discrete values as a function of body state index.

As seen in FIG. 9, calculation unit 480 receives control coefficient 482 and vehicle operating information 484 as inputs. Calculation unit 480 outputs control parameter 486. Vehicle operating information 484 can include any information necessary to calculate a control parameter. For example, in situations where the vehicle system is an electronic stability control system, the system may receive wheel speed information, steering angle information, roadway friction information, as well as other information necessary to calculate a control parameter that is used to determine when stability control should be activated. Moreover, as discussed above, control coefficient 482 may be determined from the body state index using, for example, a look-up table. Calculation unit 480 then considers both the vehicle operating information and the control coefficient in calculating control parameter 486.

It will be understood that calculation unit 480 is intended to be any general algorithm or process used to determine one or more control parameters. In some cases, calculation unit 480 may be associated with response system 199 and/or ECU 150. In other cases, however, calculation unit 480 could be associated with any other system or device of motor vehicle 100, including any of the vehicle systems discussed previously.

Figure 10:
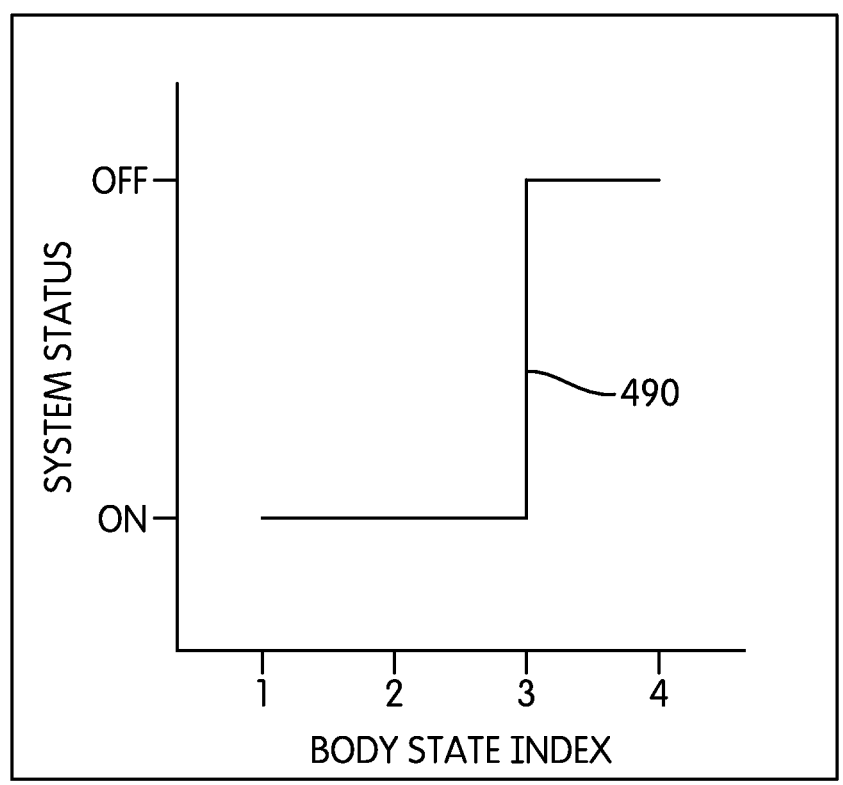
FIG. 10 is an embodiment of a relationship between body state index and a vehicle system status.

In some embodiments, a control parameter may be associated with a status or state of a given vehicle system. FIG. 10 illustrates an embodiment of a general relationship between the body state index of the driver and system status 490. The system shown here is general and could be associated with any vehicle system. For low body state index (1 or 2), the system status is ON. However, if the body state index increases to 3 or 4 the system status is turned OFF. In still other embodiments, a control parameter could be set to multiple different "states" according to the body state index. Using this arrangement, the state of a vehicle system can be modified according the body state index of a driver.

Figure 11:
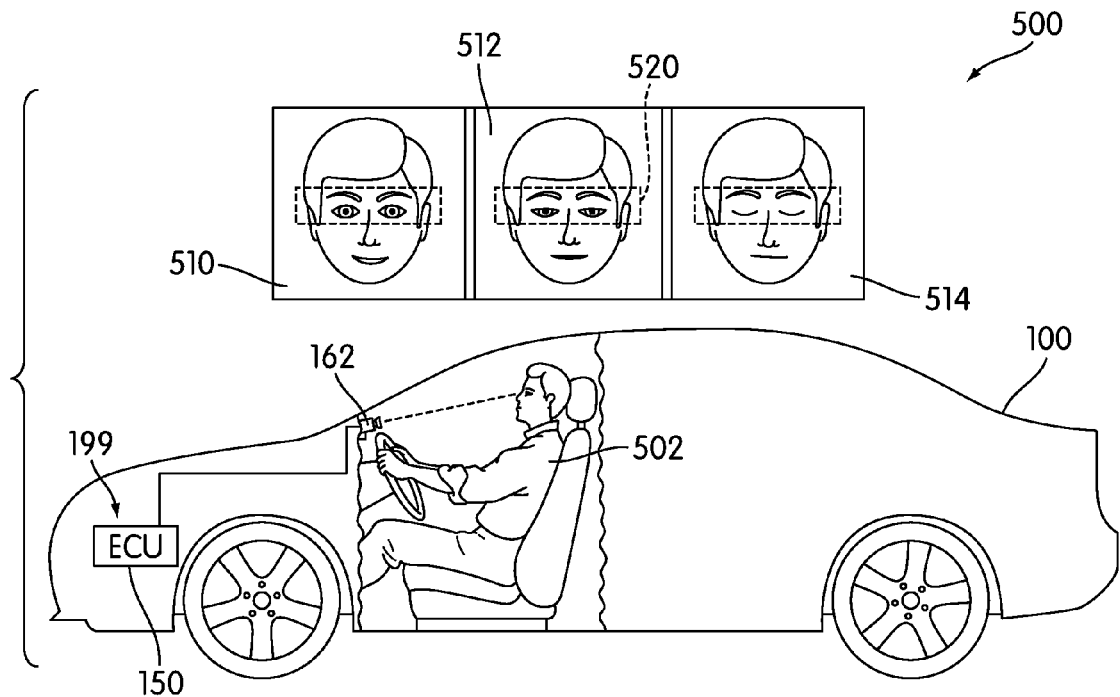
FIG. 11 is a schematic view of an embodiment of a method of monitoring the eye movement of a driver to help determine if a driver is drowsy.

A response system can include provisions for detecting the state of a driver by monitoring the eyes of a driver. FIG. 11 illustrates a schematic view of a scenario in which response system 199 is capable of monitoring the state or behavior of a driver. Referring to FIG. 11, ECU 150 may receive information from optical sensing device 162. In some cases, optical sensing device 162 may be a video camera that is mounted in the dashboard of motor vehicle 100. The information may comprise a sequence of images 500 that can be analyzed to determine the state of driver 502. First image 510 shows driver 502 in a fully awake state, with eyes 520 wide open. However, second image 512 shows driver 502 in a drowsy state, with eyes 520 half open. Finally, third image 514 shows driver 502 in a very drowsy state with eyes 520 fully closed. In some embodiments, response system 199 may be configured to analyze various images of driver 502. More specifically, response system 199 may analyze the movement of eyes 520 to determine if a driver is in a normal state or a drowsy state.

It will be understood that any type of algorithm known in the art for analyzing eye movement from images can be used. In particular, any type of algorithm that can recognize the eyes and determine the position of the eyelids between a closed and open position may be used. Examples of such algorithms may include various pattern recognition algorithms known in the art.

In other embodiments, thermal sensing device 163 can be used to sense eyelid movement. For example, as the eyelids move between opened and closed positions, the amount of thermal radiation received at thermal sensing device 163 may vary. In other words, thermal sensing device 163 can be configured to distinguish between various eyelid positions based on variations in the detected temperature of the eyes.

Figure 12:
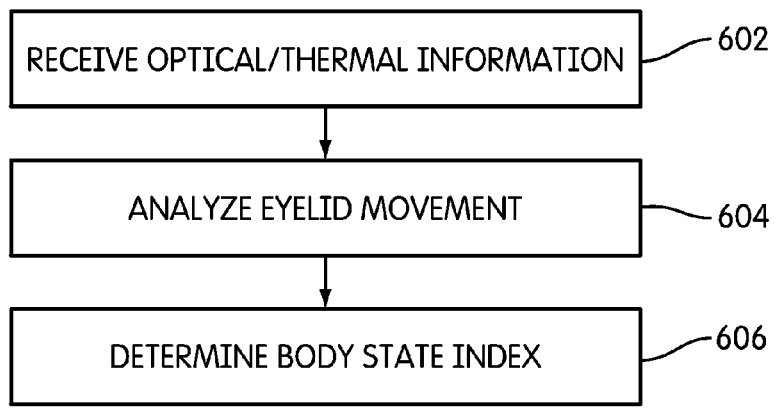
FIG. 12 is an embodiment of a process of monitoring eye movement of a driver to determine if the driver is drowsy.

FIG. 12 illustrates an embodiment of a process for detecting drowsiness by monitoring eye movement in the driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 602, response system 199 may receive optical/thermal information. In some cases, optical information could be received from a camera or other optical sensing device. In other cases, thermal information could be received from a thermal sensing device. In still other cases, both optical and thermal information could be received from a combination of optical and thermal devices.

In step 604, response system 199 may analyze eyelid movement. By detecting eyelid movement, response system 199 can determine if the eyes of a driver are open, closed or in a partially closed position. The eyelid movement can be determined using either optical information or thermal information received during step 602. Moreover, as discussed above, any type of software or algorithm can be used to determine eyelid movement from the optical or thermal information. Although the current embodiment comprises a step of analyzing eyelid movement, in other embodiments the movement of the eyeballs could also be analyzed.

In step 606, response system 199 determines the body state index of the driver according to the eyelid movement. The body state index may have any value. In some cases, the value ranges between 1 and 4, with 1 being the least drowsy and 4 being the drowsiest state. In some cases, to determine the body state index response system 199 determines if the eyes are closed or partially closed for extended periods. In order to distinguish drooping eyelids due to drowsiness from blinking, response system 199 may use a threshold time that the eyelids are closed or partially closed. If the eyes of the driver are closed or partially closed for periods longer than the threshold time, response system 199 may determine that this is due to drowsiness. In such cases, the driver may be assigned a body state index that is greater than 1 to indicate that the driver is drowsy. Moreover, response system 199 may assign different body state index values for different degrees of eyelid movement or eyelid closure.

In some embodiments, response system 199 may determine the body state index based on detecting a single instance of prolonged eyelid closure or partial eyelid closure. Of course, it may also be the case that response system 199 analyzes eye movement over an interval of time and looks at average eye movements.

Figure 13:
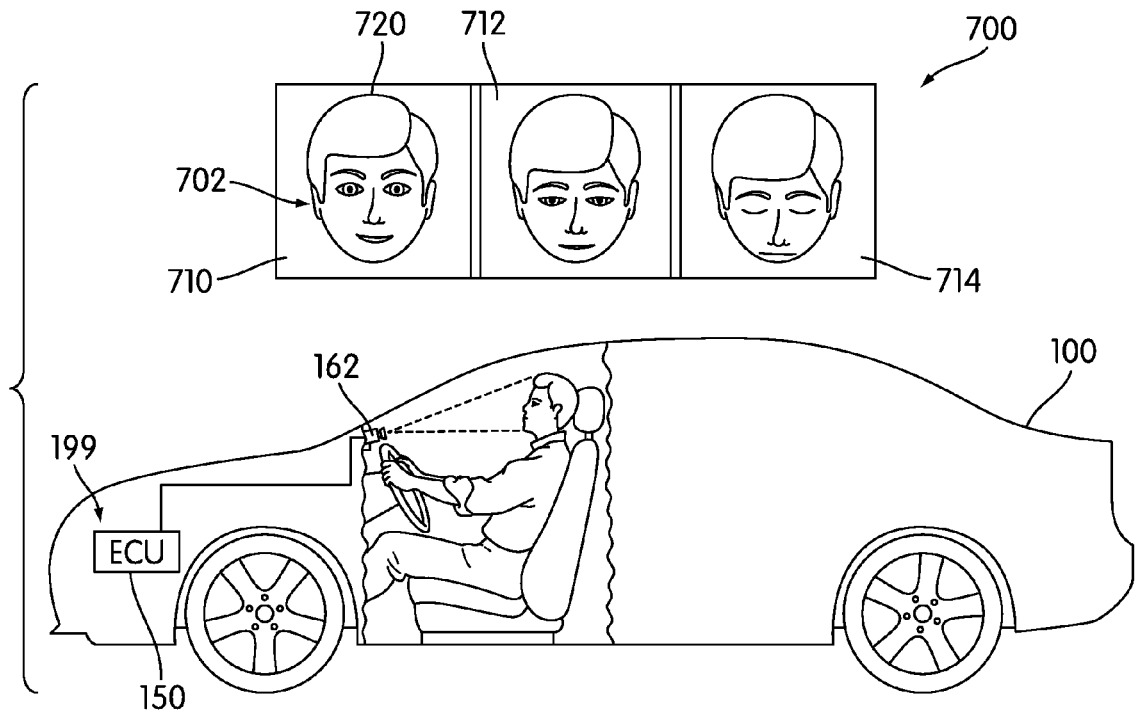
FIG. 13 is a schematic view of an embodiment of a method of monitoring the head movement of a driver to determine if the driver is drowsy.

A response system can include provisions for detecting the state of a driver by monitoring the head of a driver. FIG. 13 illustrates a schematic view of a scenario in which response system 199 is capable of monitoring the state or behavior of a driver. Referring to FIG. 13, ECU 150 may receive information from optical sensing device 162. In some cases, optical sensing device 162 may be a video camera that is mounted in the dashboard of motor vehicle 100. In other cases, a thermal sensing device could be used. The information may comprise a sequence of images 700 that can be analyzed to determine the state of driver 702. First image 710 shows driver 702 in a fully awake state, with head 720 in an upright position. However, second image 712 shows driver 702 in a drowsy state, with head 720 leaning forward. Finally, third image 714 shows driver 702 in a drowsier state with head 720 fully tilted forward. In some embodiments, response system 199 may be configured to analyze various images of driver 702. More specifically, response system 199 may analyze the movement of head 720 to determine if a driver is in a normal state or a drowsy state.

It will be understood that any type of algorithm known in the art for analyzing head movement from images can be used. In particular, any type of algorithm that can recognize the head and determine the position of the head may be used. Examples of such algorithms may include various pattern recognition algorithms known in the art.

Figure 14:
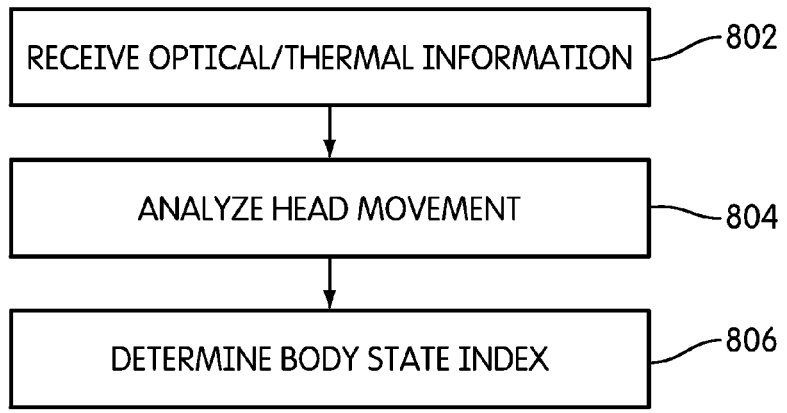
FIG. 14 is an embodiment of a process of monitoring the head movement of a driver to determine if the driver is drowsy.

FIG. 14 illustrates an embodiment of a process for detecting drowsiness by monitoring head movement in the driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 802, response system 199 may receive optical and/or thermal information. In some cases, optical information could be received from a camera or other optical sensing device. In other cases, thermal information could be received from a thermal sensing device. In still other cases, both optical and thermal information could be received from a combination of optical and thermal devices.

In step 804, response system 199 may analyze head movement. By detecting head movement, response system 199 can determine if a driver is leaning forward. The head movement can be determined using either optical information or thermal information received during step 802. Moreover, as discussed above, any type of software or algorithm can be used to determine head movement from the optical or thermal information.

In step 806, response system 199 determines the body state index of the driver in response to the detected head movement. For example, in some cases, to determine the body state index of the driver, response system 199 determines if the head is tilted in any direction for extended periods. In some cases, response system 199 may determine if the head is tilting forward. In some cases, response system 199 may assign a body state index depending on the level of tilt and/or the time interval over which the head remains tilted. For example, if the head is tilted forward for brief periods, the body state index may be assigned a value of 2, to indicate that the driver is slightly drowsy. If the head is titled forward for a significant period of time, the body state index may be assigned a value of 4 to indicate that the driver is extremely drowsy.

In some embodiments, response system 199 may determine the body state index based on detecting a single instance of a driver tilting his or her head forward. Of course, it may also be the case that response system 199 analyzes head movement over an interval of time and looks at average head movements.

Figure 15:
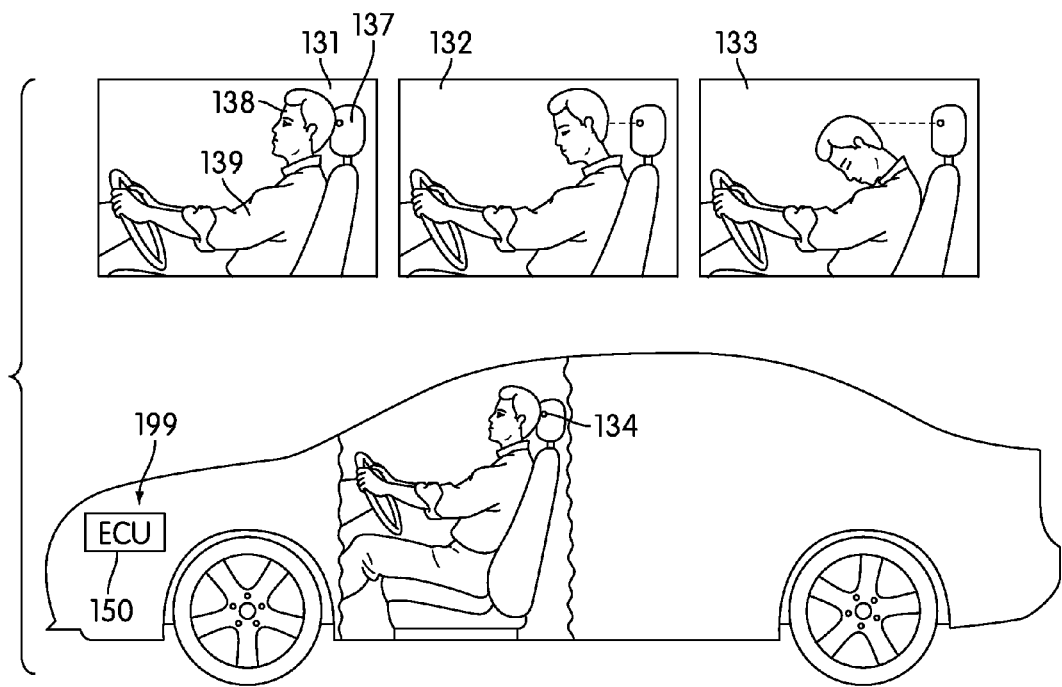
FIG. 15 is a schematic view of an embodiment of a method of monitoring the distance between the driver's head and a headrest to determine if the driver is drowsy.

A response system can include provisions for detecting the state of a driver by monitoring the relative position of the driver's head with respect to a headrest. FIG. 15 illustrates a schematic view of a scenario in which response system 199 is capable of monitoring the state or behavior of a driver. Referring to FIG. 15, ECU 150 may receive information from proximity sensor 134. In some cases, proximity sensor 134 may be a capacitor. In other cases, proximity sensor 134 may be a laser based sensor. In still other cases, any other kind of proximity sensor known in the art could be used. Response system 199 may monitor the distance between the driver's head and headrest 137. In particular, response system 199 may receive information from proximity sensor 134 that can be used to determine the distance between the driver's head and headrest 137. For example, a first configuration 131 shows driver 139 in a fully awake state, with head 138 disposed against headrest 137. However, second configuration 132 shows driver 139 in a somewhat drowsy state. In this case, head 138 has moved further away from headrest 137 as the driver slumps forward slightly. A third configuration 133 shows driver 139 in a fully drowsy state. In this case, head 138 is moved still further away from headrest 137 as the driver is further slumped over. In some embodiments, response system 199 may be configured to analyze information related to the distance between the driver's head 138 and headrest 137. Moreover, response system 199 can analyze head position and/or movement (including tilting, slumping and/or bobbing) to determine if driver 139 is in a normal state or a drowsy state.

It will be understood that any type of algorithm known in the art for analyzing head distance and/or movement from proximity or distance information can be used. In particular, any type of algorithm that can determine the relative distance between a headrest and the driver's head can be used. Also, any algorithms for analyzing changes in distance to determine head motion could also be used. Examples of such algorithms may include various pattern recognition algorithms known in the art.

Figure 16:
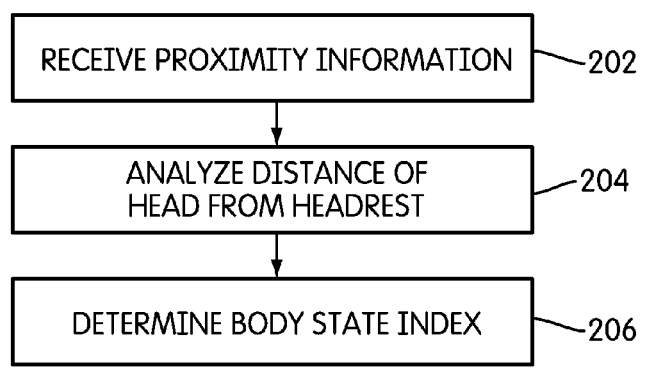
FIG. 16 is an embodiment of a process of monitoring the distance between the driver's head and a headrest to determine if the driver is drowsy.

FIG. 16 illustrates an embodiment of a process for detecting drowsiness by monitoring the distance of the driver's head from a headrest. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 202, response system 199 may receive proximity information. In some cases, proximity information could be received from a capacitor or laser based sensor. In other cases, proximity information could be received from any other sensor. In step 204, response system 199 may analyze the distance of the head from a headrest. By determining the distance between the driver's head and the head rest, response system 199 can determine if a driver is leaning forward. Moreover, by analyzing head distance over time, response system 199 can also detect motion of the head. The distance of the head from the headrest can be determined using any type of proximity information received during step 202. Moreover, as discussed above, any type of software or algorithm can be used to determine the distance of the head and/or head motion information.

In step 206, response system 199 determines the body state index of the driver in response to the detected head distance and/or head motion. For example, in some cases, to determine the body state index of the driver, response system 199 determines if the head is leaning away from the headrest for extended periods. In some cases, response system 199 may determine if the head is tilting forward. In some cases, response system 199 may assign a body state index depending on the distance of the head from the head rest as well as from the time interval over which the head is located away from the headrest. For example, if the head is located away from the headrest for brief periods, the body state index may be assigned a value of 2, to indicate that the driver is slightly drowsy. If the head is located away from the headrest for a significant period of time, the body state index may be assigned a value of 4 to indicate that the driver is extremely drowsy. It will be understood that in some cases, a system could be configured so that the alert state of the driver is associated with a predetermined distance between the head and the headrest. This predetermined distance could be a factory set value or a value determined by monitoring a driver over time. Then, the body state index may be increased when the driver's head moves closer to the headrest or further from the headrest with respect to the predetermined distance. In other words, in some cases the system may recognize that the driver's head may tilt forward and/or backward as he or she gets drowsy.

In some embodiments, response system 199 may determine the body state index based on detecting a single distance measurement between the driver's head and a headrest. Of course, it may also be the case that response system 199 analyzes the distance between the driver's head and the headrest over an interval of time and uses average distances to determine body state index.

In some other embodiments, response system 199 could detect the distance between the driver's head and any other reference location within the vehicle. For example, in some cases a proximity sensor could be located in a ceiling of the vehicle and response system 199 may detect the distance of the driver's head with respect to the location of the proximity sensor. In other cases, a proximity sensor could be located in any other part of the vehicle. Moreover, in other embodiments, any other portions of a driver could be monitored for determining if a driver is drowsy or otherwise alert. For example, in still another embodiment, a proximity sensor could be used in the backrest of a seat to measure the distance between the backrest and the back of the driver.

Figure 17:
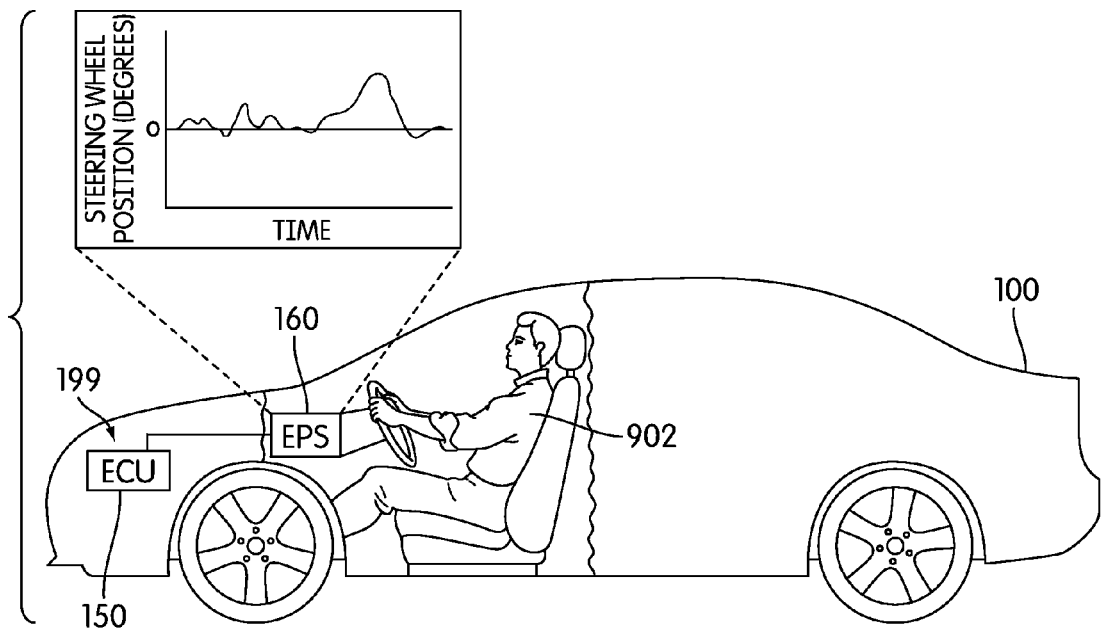
FIG. 17 is a schematic view of an embodiment of a method of monitoring steering information to determine if a driver is drowsy.

A response system can include provisions for detecting abnormal steering by a driver for purposes of determining if a driver is drowsy. FIG. 17 illustrates a schematic view of motor vehicle 100 being operated by driver 902. In this situation, ECU 150 may receive information related to the steering angle or steering position as a function of time. In addition, ECU 150 could also receive information about the torque applied to a steering wheel as a function of time. In some cases, the steering angle information or torque information can be received from EPS system 160, which may include a steering angle sensor as well as a torque sensor. By analyzing the steering position or steering torque over time, response system 199 can determine if the steering is inconsistent, which may indicate that the driver is drowsy.

Figure 18:
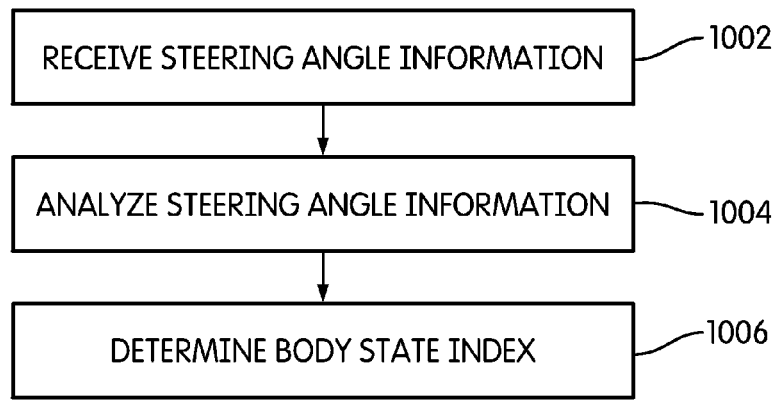
FIG. 18 is an embodiment of a process of monitoring steering information to determine if a driver is drowsy.

FIG. 18 illustrates an embodiment of a process for detecting drowsiness by monitoring the steering behavior of a driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 1002, response system 199 may receive steering angle information. In some cases, the steering angle information may be received from EPS 160 or directly from a steering angle sensor. Next, in step 1004, response system 199 may analyze the steering angle information. In particular, response system 199 may look for patterns in the steering angle as a function of time that suggest inconsistent steering, which could indicate a drowsy driver. Any method of analyzing steering information to determine if the steering is inconsistent can be used. Moreover, in some embodiments, response system 199 may receive information from lane keep assist system 244 to determine if a driver is steering motor vehicle 100 outside of a current lane.

In step 1006, response system 199 may determine the body state index of the driver based on steering wheel movement.

For example, if the steering wheel movement is inconsistent, response system 199 may assign a body state index of 2 or greater to indicate that the driver is drowsy.

Figure 19:
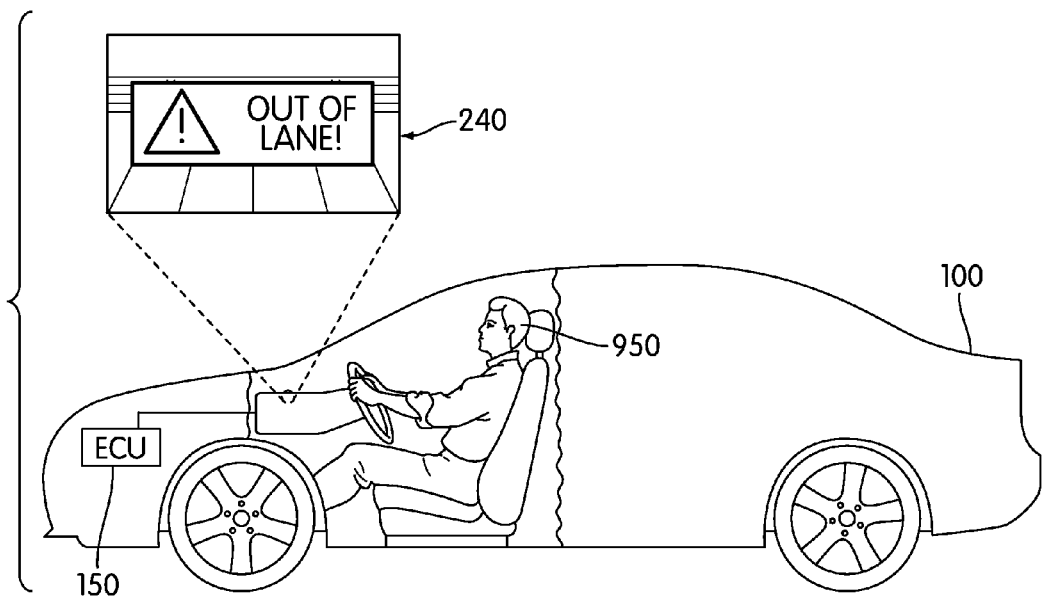
FIG. 19 is a schematic view of an embodiment of a method of monitoring lane departure information to determine if a driver is drowsy.

A response system can include provisions for detecting abnormal driving behavior by monitoring lane departure information. FIG. 19 illustrates a schematic view of an embodiment of motor vehicle 100 being operated by driver 950. In this situation, ECU 150 may receive lane departure information. In some cases, the lane departure information can be received from LDW system 240. Lane departure information could include any kind of information related to the position of a vehicle relative to one or more lanes, steering behavior, trajectory or any other kind of information. In some cases, the lane departure information could be processed information analyzed by LDW system 240 that indicates some kind of lane departure behavior. By analyzing the lane departure information, response system 199 can determine if the driving behavior is inconsistent, which may indicate that the driver is drowsy. In some embodiments, whenever LDW system 240 issues a lane departure warning, response system 199 may determine that the driver is drowsy. Moreover, the level of drowsiness could be determined by the intensity of the warning.

Figure 20:
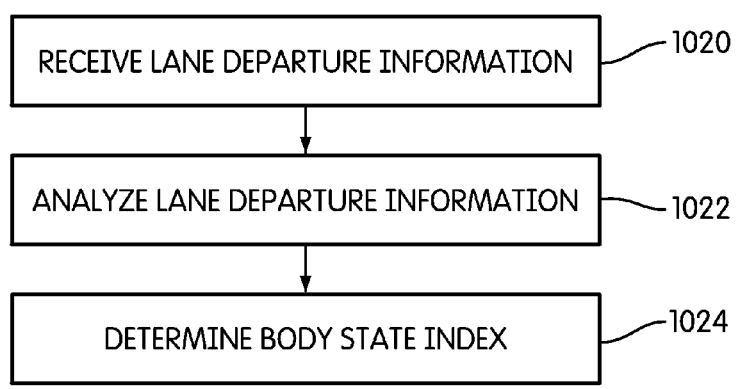
FIG. 20 is an embodiment of a process of monitoring lane departure information to determine if a driver is drowsy.

FIG. 20 illustrates an embodiment of a process for detecting drowsiness by monitoring lane departure information. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 1020, response system 199 may receive lane departure information. In some cases, the lane departure information may be received from LWD system 240 or directly from some kind of sensor (such as a steering angle sensor, or a relative position sensor). Next, in step 1022, response system 199 may analyze the lane departure information. Any method of analyzing lane departure information can be used.

In step 1024, response system 199 may determine the body state index of the driver based on lane departure information. For example, if the vehicle is drifting out of the current lane, response system 199 may assign a body state index of 2 or greater to indicate that the driver is drowsy. Likewise, if the lane departure information is a lane departure warning from LDW system 240, response system 199 may assign a body state index of 2 or greater to indicate that the driver is drowsy. Using this process, response system 199 can use information from one or more vehicle systems 172 to help determine if a driver is drowsy. This is possible since drowsiness (or other types of inattentiveness) not only manifest as driver behaviors, but can also cause changes in the operation of the vehicle, which may be monitored by the various vehicle systems 172.

Figure 21:
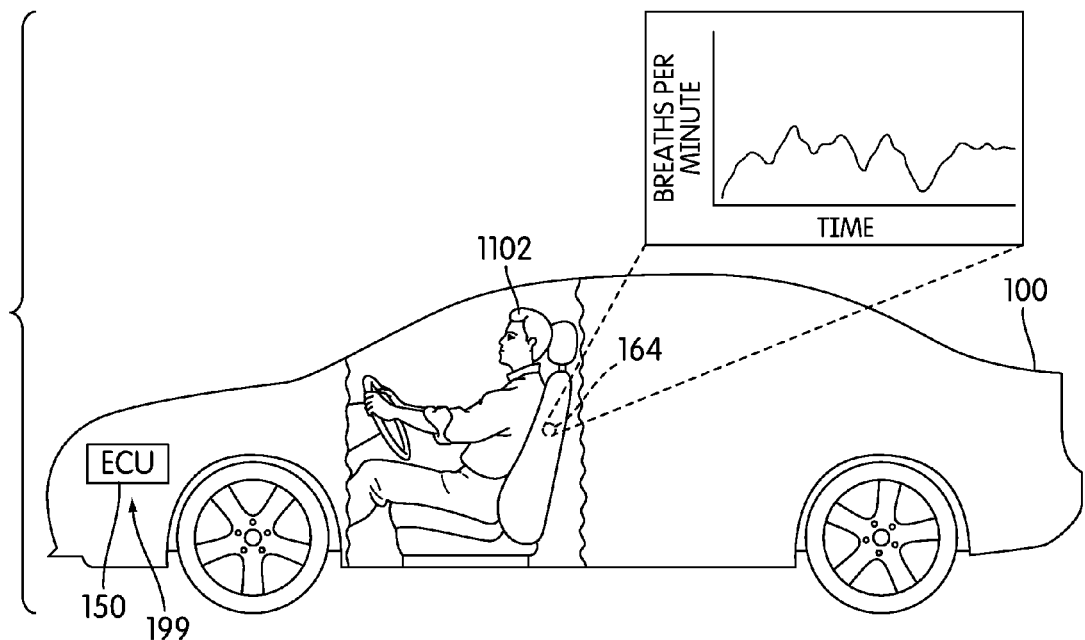
FIG. 21 is a schematic view of an embodiment of a method of monitoring autonomic nervous system information to determine if a driver is drowsy.

FIG. 21 illustrates a schematic view of an embodiment of motor vehicle 100, in which response system 199 is capable of detecting respiratory rate information. In particular, using bio-monitoring sensor 164, ECU 150 may be able to determine the number of breaths per minute taken by driver 1102. This information can be analyzed to determine if the measured breaths per minute coincides with a normal state or a drowsy state. Breaths per minute is given as an example, any other autonomic information could also be monitored and used to determine this state.

Figure 22:
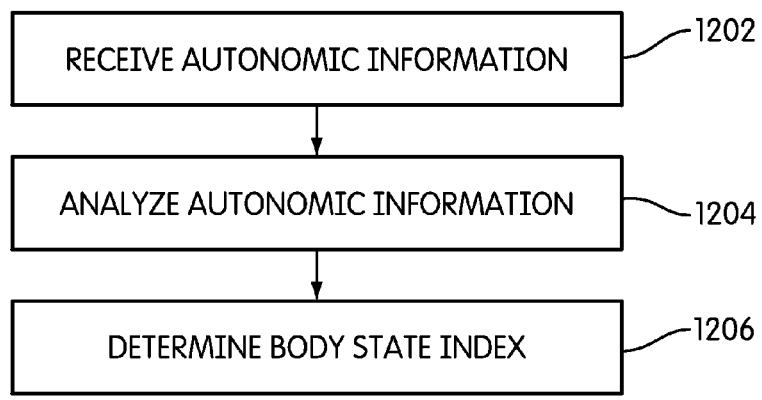
FIG. 22 is an embodiment of a process of monitoring autonomic nervous system information to determine if a driver is drowsy.

FIG. 22 illustrates an embodiment of a process for detecting drowsiness by monitoring the autonomic information of a driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as the vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 1202, response system 199 may receive information related to the autonomic nervous system of the driver. In some cases, the information can be received from a sensor. The sensor could be associated with any portion of motor vehicle 100 including a seat, armrest or any other portion. Moreover, the sensor could be a portable sensor in some cases.

In step 1204, response system 199 may analyze the autonomic information. Generally, any method of analyzing autonomic information to determine if a driver is drowsy could be used. It will be understood that the method of analyzing the autonomic information may vary according to the type of autonomic information being analyzed. In step 1206, response system 199 may determine the body state index of the driver based on the analysis conducted during step 1204.

It will be understood that the methods discussed above for determining the body state index of a driver according to eye movement, head movement, steering wheel movement and/or sensing autonomic information are only intended to be exemplary and in other embodiments any other method of detecting the behavior of a driver, including behaviors associated with drowsiness, could be used. Moreover, it will be understood that in some embodiments multiple methods for detecting driver behavior to determine a body state index could be used simultaneously.

A response system can include provisions for controlling one or more vehicle systems to help wake a drowsy driver. For example, a response system could control various systems to stimulate a driver in some way (visually, orally, or through movement, for example). A response system could also change ambient conditions in a motor vehicle to help wake the driver and thereby increase the driver's alertness.

Figure 23:
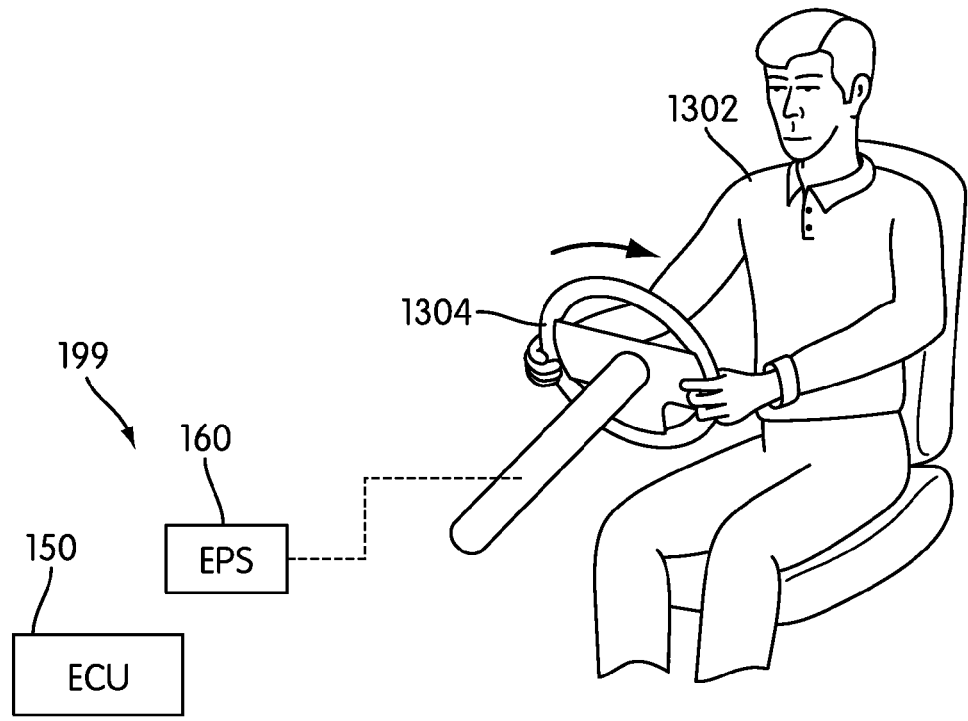
FIG. 23 is a schematic view of an embodiment of a method of modifying the operation of a power steering system when a driver is drowsy.
Figure 24:
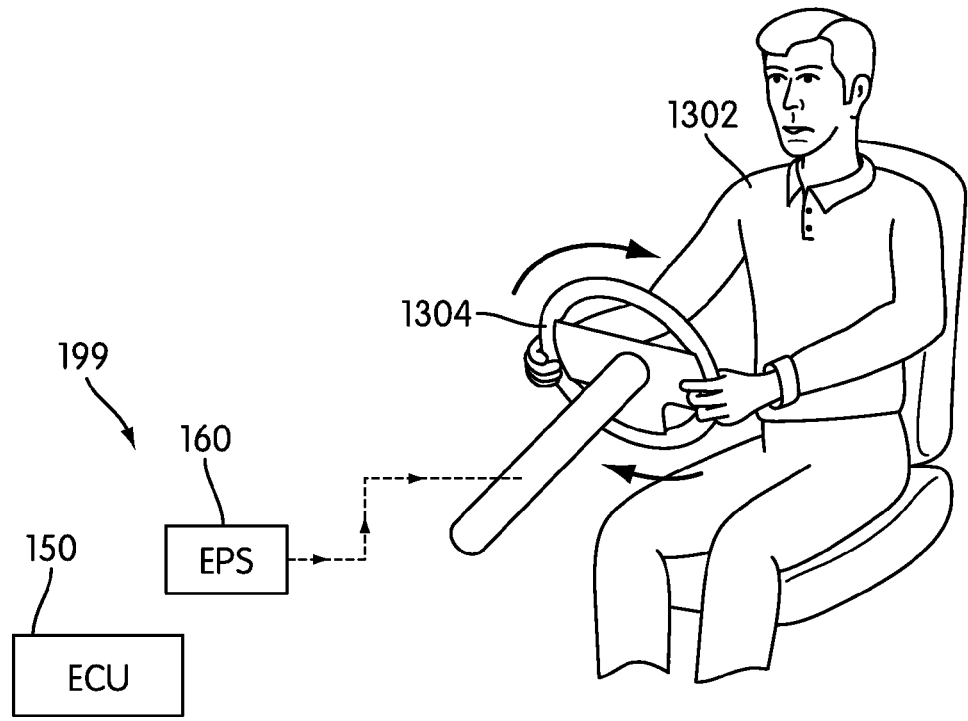
FIG. 24 is a schematic view of an embodiment of a method of modifying the operation of a power steering system when a driver is drowsy.

FIGS. 23 and 24 illustrate a schematic view of a method of waking a driver by modifying the control of an electronic power steering system. Referring to FIG. 23, driver 1302 is drowsy. Response system 199 may detect that driver 1302 is drowsy using any of the detection methods mentioned previously or through any other detection methods. During normal operation, EPS system 160 functions to assist a driver in turning steering wheel 1304. However, in some situations, it may be beneficial to reduce this assistance. For example, as seen in FIG. 24, by decreasing the power steering assistance, driver 1302 must put more effort into turning steering wheel 1304. This may have the effect of waking up driver 1302, since driver 1302 must now apply a greater force to turn steering wheel 1304.

Figure 25:
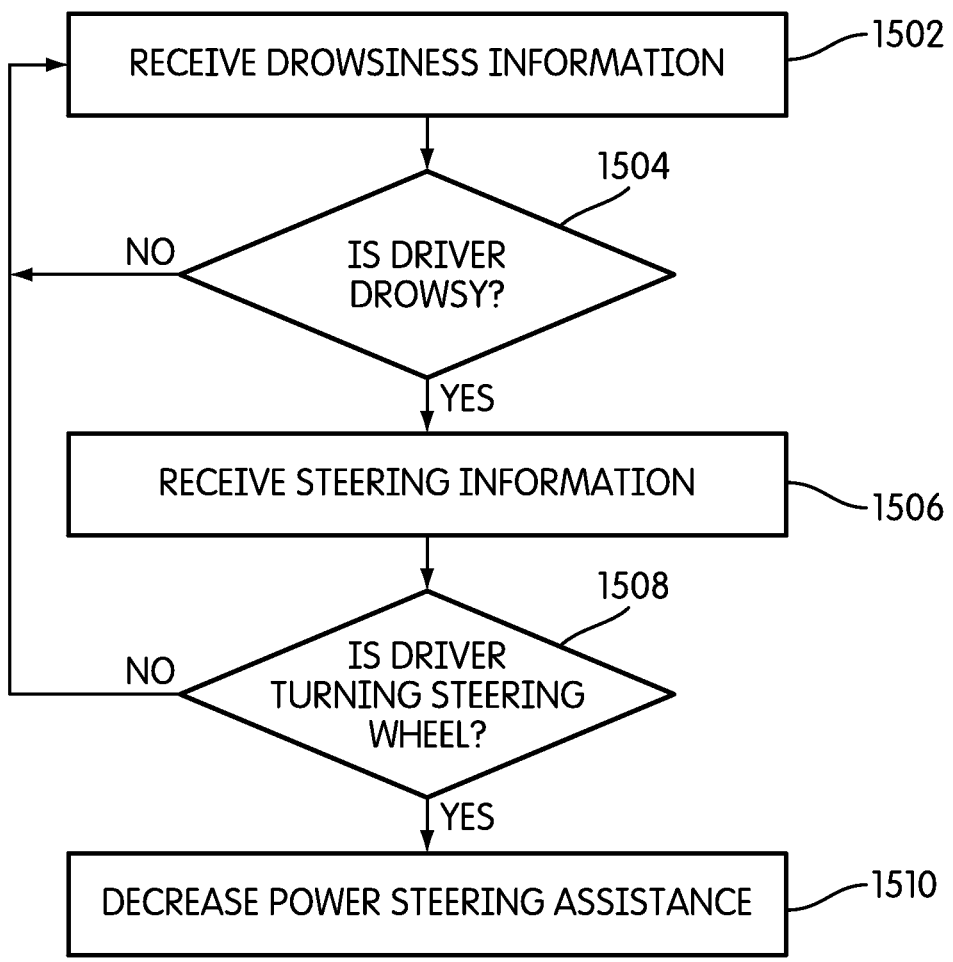
FIG. 25 is an embodiment of a process of controlling a power steering system when a driver is drowsy.

FIG. 25 illustrates an embodiment of a process for controlling power steering assistance according to the detected level of drowsiness for a driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 1502, response system 199 may receive drowsiness information. In some cases, the drowsiness information includes whether a driver is in a normal state or a drowsy state. Moreover, in some cases, the drowsiness information could include a value indicating the level of drowsiness, for example on a scale of 1 to 10, with 1 being the least drowsy and 10 being the drowsiest.

In step 1504, response system 199 determines if the driver is drowsy based on the drowsiness information. If the driver is not drowsy, response system 199 returns back to step 1502. If the driver is drowsy, response system 199 proceeds to step 1506. In step 1506, steering wheel information may be received. In some cases, the steering wheel information can be received from EPS system 160. In other cases, the steering wheel information can be received from a steering angle sensor or a steering torque sensor directly.

In step 1508, response system 199 may determine if the driver is turning the steering wheel. If not, response system 199 returns to step 1502. If the driver is turning the steering wheel, response system 199 proceeds to step 1510 where the power steering assistance is decreased. It will be understood that in some embodiments, response system 199 may not check to see if the wheel is being turned before decreasing power steering assistance.

Figure 26:
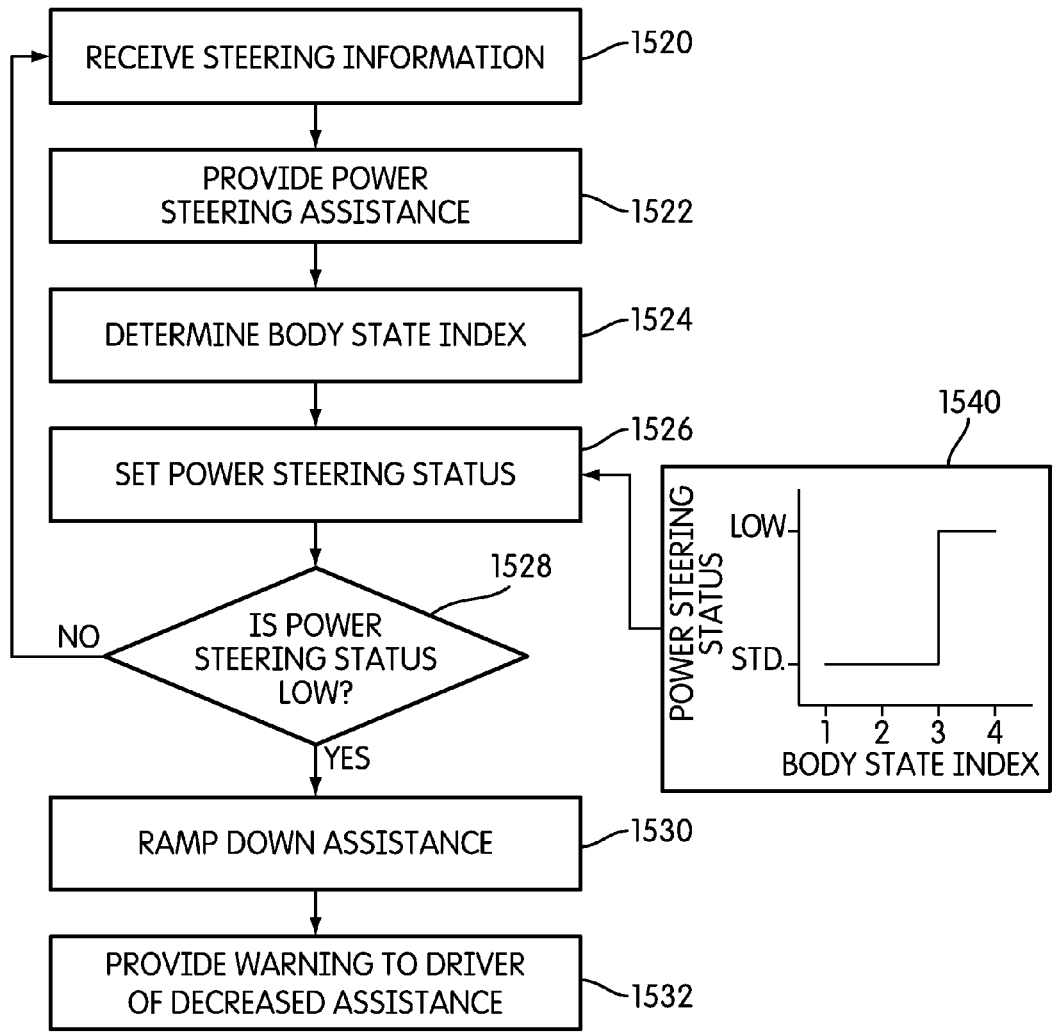
FIG. 26 is an embodiment of a detailed process for controlling power steering assistance in response to driver behavior.

FIG. 26 illustrates an embodiment of a detailed process for controlling power steering assistance to a driver according to a body state index. In step 1520, response system 199 may receive steering information. The steering information can include any type of information including steering angle, steering torque, rotational speed, motor speed as well as any other steering information related to a steering system and/or a power steering assistance system. In step 1522, response system 199 may provide power steering assistance to a driver. In some cases, response system 199 provides power steering assistance in response to a driver request (for example, when a driver turns on a power steering function). In other cases, response system 199 automatically provides power steering assistance according to vehicle conditions or other information.

In step 1524, response system 199 may determine the body state index of a driver using any of the methods discussed above for determining a body state index. Next, in step 1526, response system 199 may set a power steering status corresponding to the amount of steering assistance provided by the electronic power steering system. For example, in some cases, the power steering status is associated with two states, including a "low" state and a "standard" state. In the "standard" state, power steering assistance is applied at a predetermined level corresponding to an amount of power steering assistance that improves drivability and helps increase the driving comfort of the user. In the "low" state, less steering assistance is provided, which requires increased steering effort by a driver. As indicated by look-up table 1540, the power steering status may be selected according to the body state index. For example, if the body state index is 1 or 2 (corresponding to no drowsiness or slight drowsiness), the power steering status is set to the standard state. If, however, the body state index is 3 or 4 (corresponding to a drowsy condition of the driver), the power steering status is set to the low state. It will be understood that look-up table 1540 is only intended to be exemplary and in other embodiments the relationship between body state index and power steering status can vary in any manner.

Once the power steering status is set in step 1526, response system 199 proceeds to step 1528. In step 1528, response system 199 determines if the power steering status is set to low. If not, response system 199 may return to step 1520 and continue operating power steering assistance at the current level. However, if response system 199 determines that the power steering status is set to low, response system 199 may proceed to step 1530. In step 1530, response system 199 may ramp down power steering assistance. For example, if the power steering assistance is supplying a predetermined amount of torque assistance, the power steering assistance may be varied to reduce the assisting torque. This requires the driver to increase steering effort. For a drowsy driver, the increased effort required to turn the steering wheel may help increase his or her alertness and improve vehicle handling.

In some cases, during step 1532, response system 199 may provide a warning to the driver of the decreased power steering assistance. For example, in some cases, a dashboard light reading "power steering off" or "power steering decreased" could be turned on. In other cases, a navigation screen or other display screen associated with the vehicle could display a message indicating the decreased power steering assistance. In still other cases, an audible or haptic indicator could be used to alert the driver. This helps to inform the driver of the change in power steering assistance so the driver does not become concerned of a power steering failure.

Figure 27:
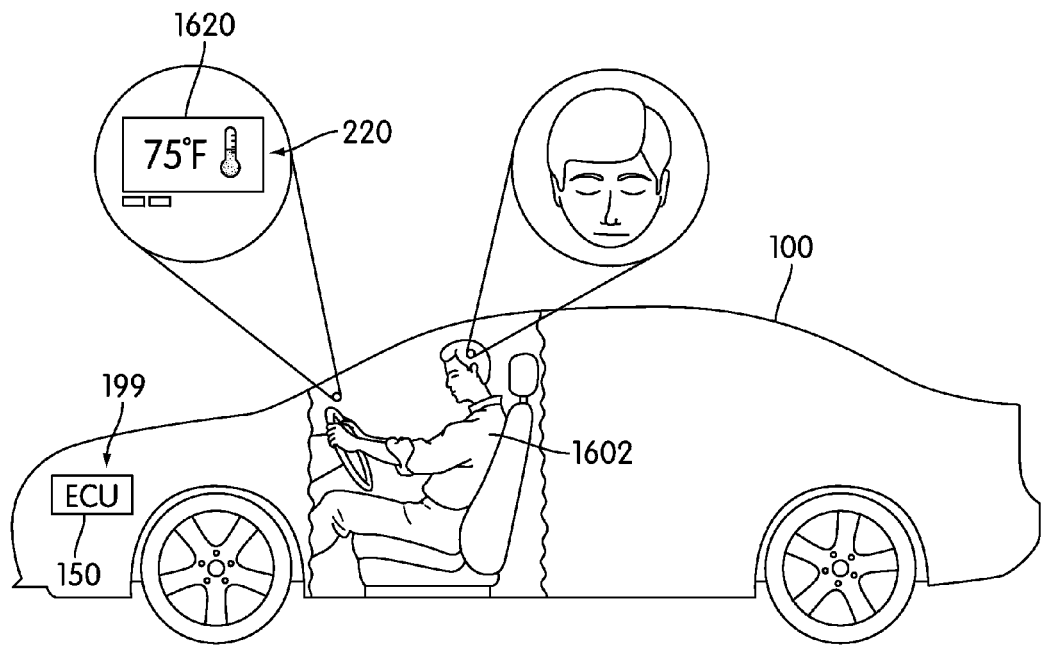
FIG. 27 is a schematic view of an embodiment of a method of modifying the operation of a climate control system when a driver is drowsy.
Figure 28:
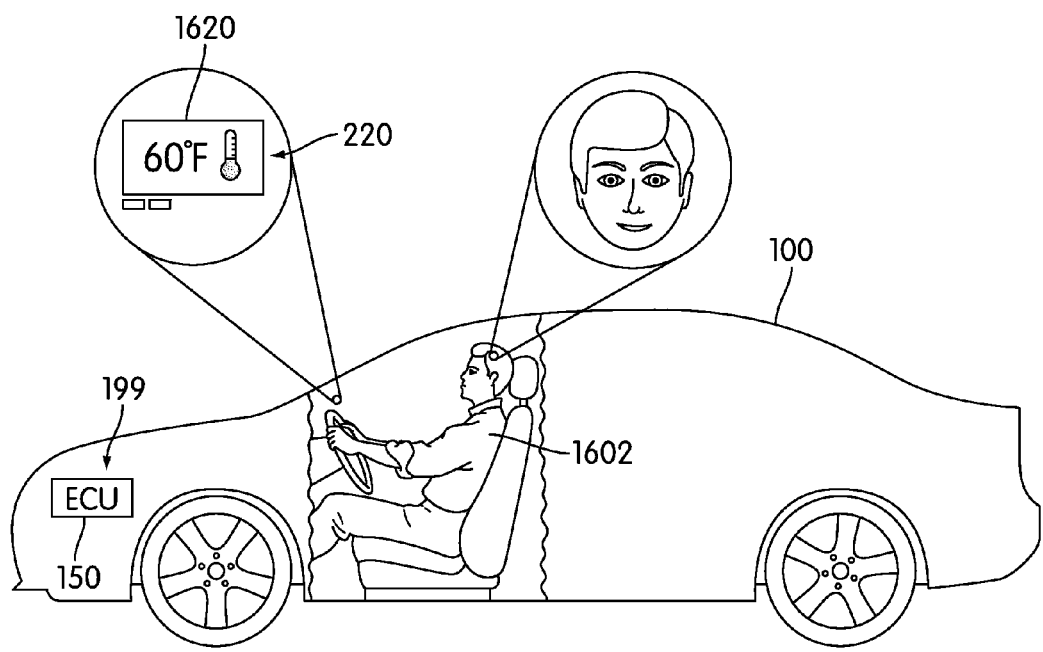
FIG. 28 is a schematic view of an embodiment of a method of modifying the operation of a climate control system when a driver is drowsy.

FIGS. 27 and 28 illustrate schematic views of a method of helping to wake a drowsy driver by automatically modifying the operation of a climate control system. Referring to FIG. 27, climate control system 250 has been set to maintain a temperature of 75 degrees Fahrenheit inside the cabin of motor vehicle 100 by driver 1602. This is indicated on display screen 1620. As response system 199 detects that driver 1602 is becoming drowsy, response system 199 may automatically change the temperature of climate control system 250. As seen in FIG. 28, response system 199 automatically adjusts the temperature to 60 degrees Fahrenheit. As the temperature inside motor vehicle 100 cools down, driver 1602 may become less drowsy, which helps driver 1602 to be more alert while driving. In other embodiments, the temperature may be increased in order to make the driver more alert.

Figure 29:
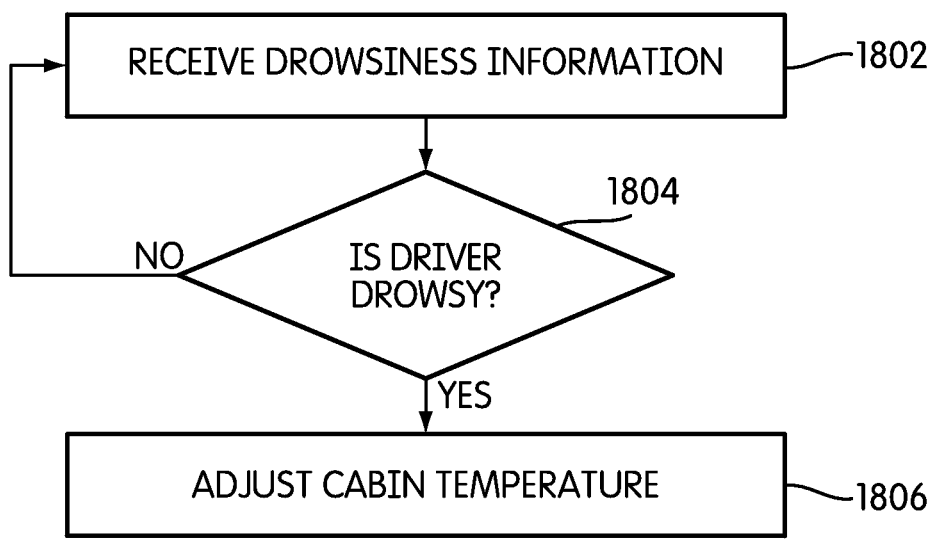
FIG. 29 is a process of controlling a climate control system when a driver is drowsy.

FIG. 29 illustrates an embodiment of a process for helping to wake a driver by controlling the temperature in a vehicle. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 1802, response system 199 may receive drowsiness information. In step 1804, response system 199 determines if the driver is drowsy. If the driver is not drowsy, response system 199 proceeds back to step 1802. If the driver is drowsy, response system 199 proceeds to step 1806. In step 1806, response system 199 automatically adjusts the cabin temperature. In some cases, response system 199 may lower the cabin temperature by engaging a fan or air-conditioner. However, in some other cases, response system 199 could increase the cabin temperature using a fan or heater. Moreover, it will be understood that the embodiments are not limited to changing temperature and in other embodiments other aspects of the in-cabin climate could be changed, including airflow, humidity, pressure or other ambient conditions. For example, in some cases, a response system could automatically increase the airflow into the cabin, which may stimulate the driver and help reduce drowsiness.

Figure 30:
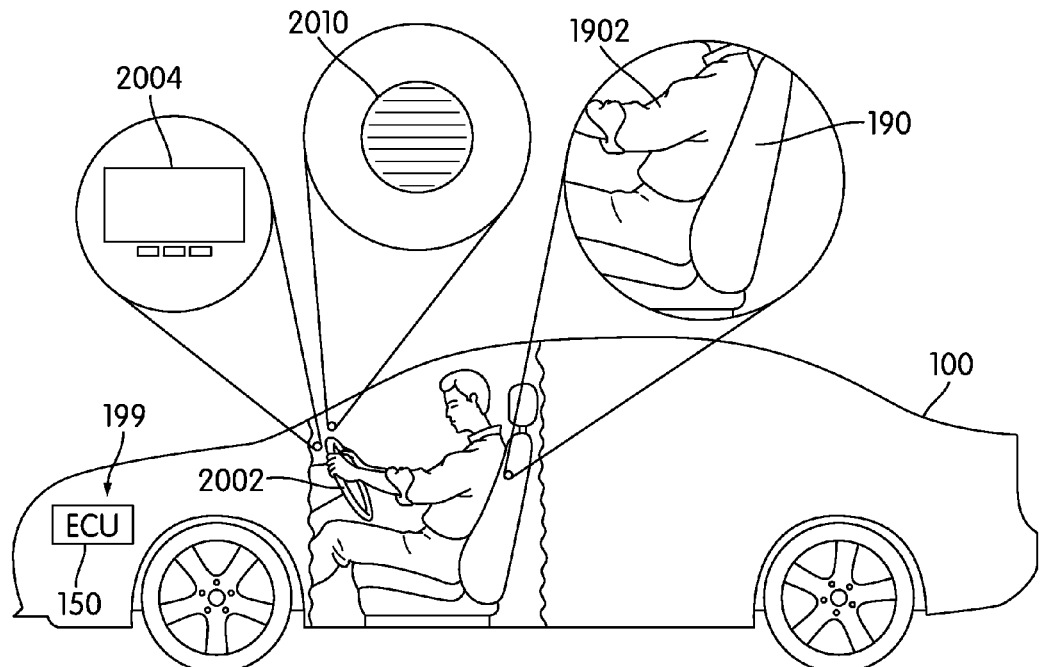
FIG. 30 is a schematic view of an embodiment of various provisions that can be used to wake a drowsy driver.
Figure 31:
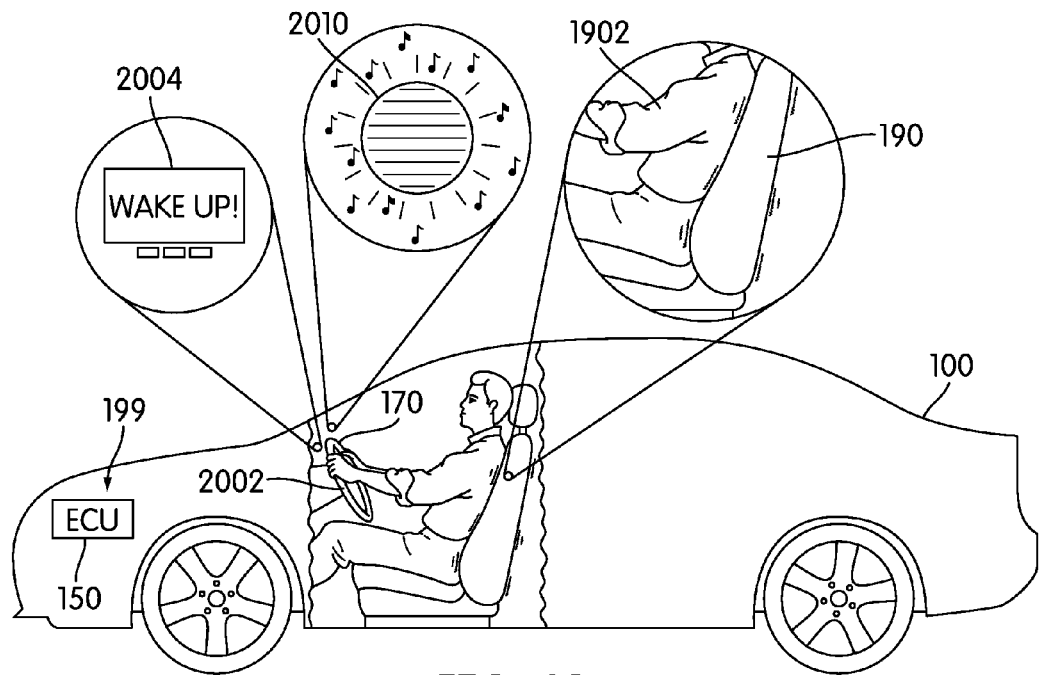
FIG. 31 is a schematic view of an embodiment of a method of waking up a drowsy driver using tactile devices, visual devices and audio devices.

FIGS. 30 and 31 illustrate schematic views of methods of alerting a drowsy driver using visual, audible and tactile feedback for a driver. Referring to FIG. 30, driver 1902 is drowsy as motor vehicle 100 is moving. Once response system 199 detects this drowsy state, response system 199 may activate one or more feedback mechanisms to help wake driver 1902. Referring to FIG. 31, three different methods of waking a driver are shown. In particular, response system 199 may control one or more tactile devices 170. Examples of tactile devices include vibrating devices (such as a vibrating seat or massaging seat) or devices whose surface properties can be modified (for example, by heating or cooling or by adjusting the rigidity of a surface). In one embodiment, response system 199 may operate driver seat 190 to shake or vibrate. This may have the effect of waking driver 1902. In other cases, steering wheel 2002 could be made to vibrate or shake. In addition, in some cases, response system 199 could activate one or more lights or other visual indicators. For example, in one embodiment, a warning may be displayed on display screen 2004. In one example, the warning may be "Wake!" and may include a brightly lit screen to catch the driver's attention. In other cases, overhead lights or other visual indicators could be turned on to help wake the driver. In some embodiments, response system 199 could generate various sounds through speakers 2010. For example, in some cases, response system 199 could activate a radio, CD player, MP3 player or other audio device to play music or other sounds through speakers 2010. In other cases, response system 199 could play various recordings stored in memory, such as voices that tell a driver to wake.

Figure 32:
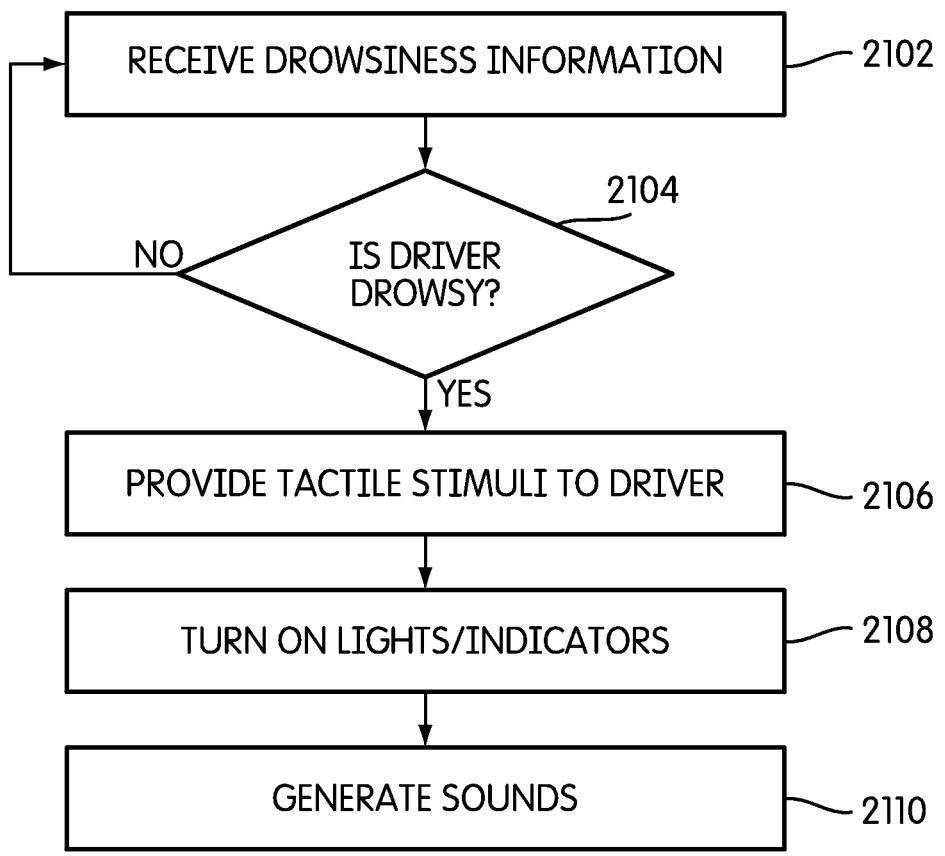
FIG. 32 is an embodiment of a process for waking up a drowsy driver using tactile devices, visual devices and audio devices.

FIG. 32 illustrates an embodiment of a process for waking up a driver using various visual, audible and tactile stimuli. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 2102, response system 199 may receive drowsiness information. In step 2104, response system 199 determines if the driver is drowsy. If the driver is not drowsy, response system 199 returns to step 2102. Otherwise, response system 199 proceeds to step 2106. In step 2106, response system 199 may provide tactile stimuli to the driver. For example, response system 199 could control a seat or other portion of motor vehicle 100 to shake and/or vibrate (for example, a steering wheel). In other cases, response system 199 could vary the rigidity of a seat or other surface in motor vehicle 100.

In step 2108, response system 199 may turn on one or more lights or indicators. The lights could be any lights associated with motor vehicle 100 including dashboard lights, roof lights or any other lights. In some cases, response system 199 may provide a brightly lit message or background on a display screen, such as a navigation system display screen or climate control display screen. In step 2110, response system 199 may generate various sounds using speakers in motor vehicle 100. The sounds could be spoken words, music, alarms or any other kinds of sounds. Moreover, the volume level of the sounds could be chosen to ensure the driver is put in an alert state by the sounds, but not so loud as to cause great discomfort to the driver.

A response system can include provisions for controlling a seatbelt system to help wake a driver. In some cases, a response system can control an electronic pretensioning system for a seatbelt to provide a warning pulse to a driver.

Figure 33:
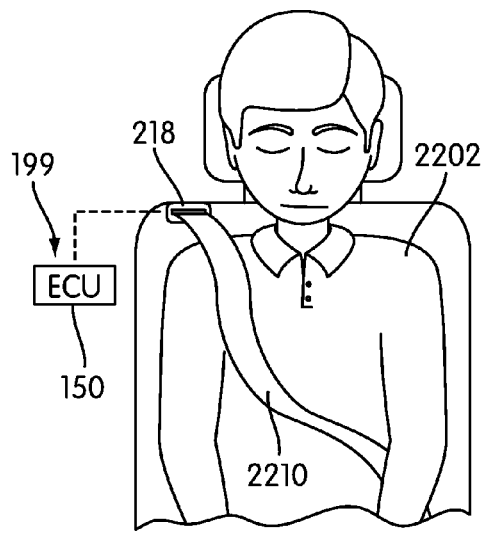
FIG. 33 is a schematic view of an electronic pretensioning system for a motor vehicle.
Figure 34:
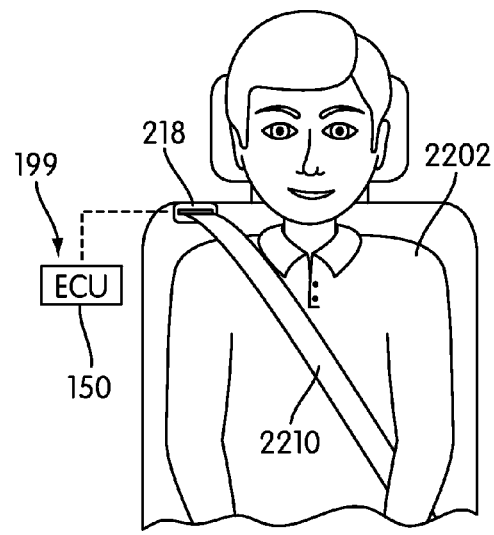
FIG. 34 is a schematic view of a method of waking up a driver using the electronic pretensioning system of FIG. 33.

FIGS. 33 and 34 illustrate schematic views of an embodiment of a response system controlling an electronic pretensioning system for a seatbelt. Referring to FIGS. 33 and 34, as driver 2202 begins to feel drowsy, response system 199 may automatically control EPT system 254 to provide a warning pulse to driver 2202. In particular, seatbelt 2210 may be initially loose as seen in FIG. 33, but as driver 2202 gets drowsy, seatbelt 2210 is pulled taut against driver 2202 for a moment as seen in FIG. 34. This momentary tightening serves as a warning pulse that helps to wake driver 2202.

Figure 35:
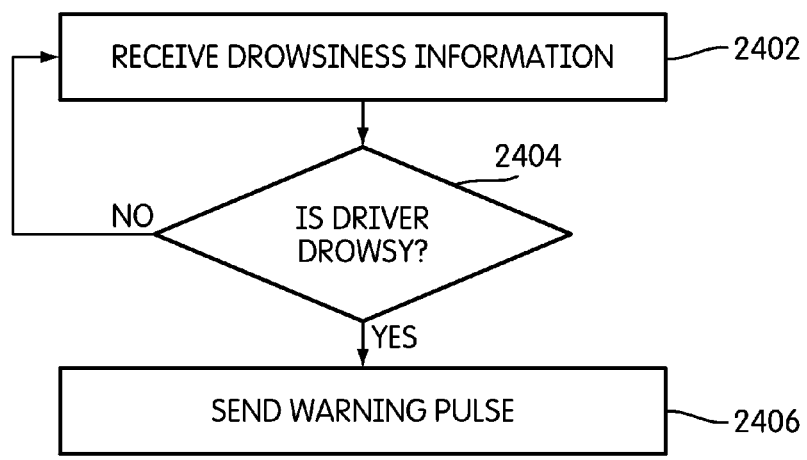
FIG. 35 is an embodiment of a process of controlling an electronic pretensioning system according to driver behavior.

FIG. 35 illustrates an embodiment of a process for controlling EPT system 254. During step 2402, response system 199 receives drowsiness information. During step 2404, response system 199 determines if the driver is drowsy. If the driver is not drowsy, response system 199 returns to step 2402. If the driver is drowsy, response system 199 proceeds to step 2406 where a warning pulse is sent. In particular, the seatbelt may be tightened to help wake or alert the driver.

A motor vehicle can include provisions for adjusting various brake control systems according to the behavior of a driver. For example, a response system can modify the control of antilock brakes, brake assist, brake prefill as well as other braking systems when a driver is drowsy. This arrangement helps to increase the effectiveness of the braking system in hazardous driving situations that may result when a driver is drowsy.

Figure 36:
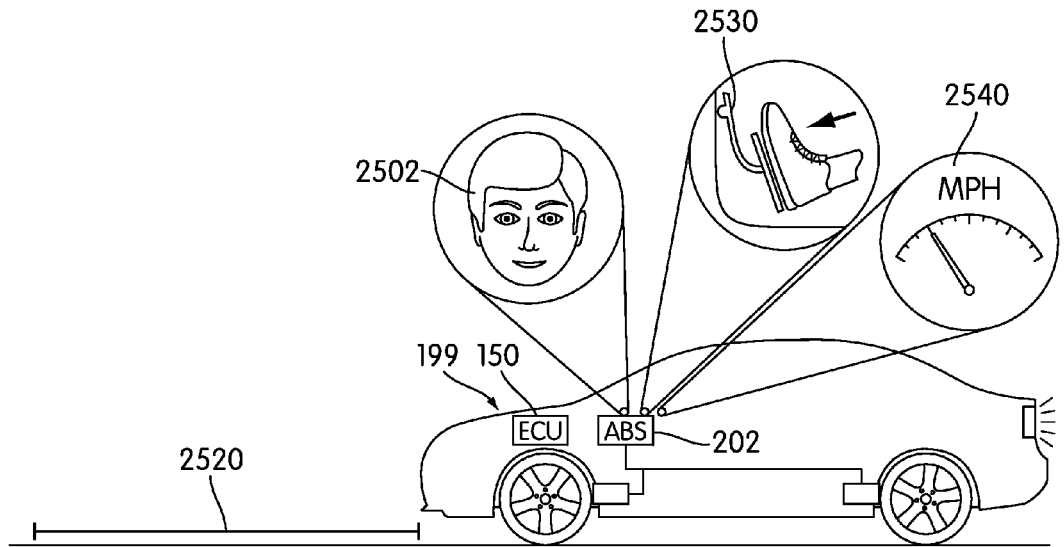
FIG. 36 is a schematic view of an embodiment of a method of operating an antilock braking system when a driver is fully awake.
Figure 37:
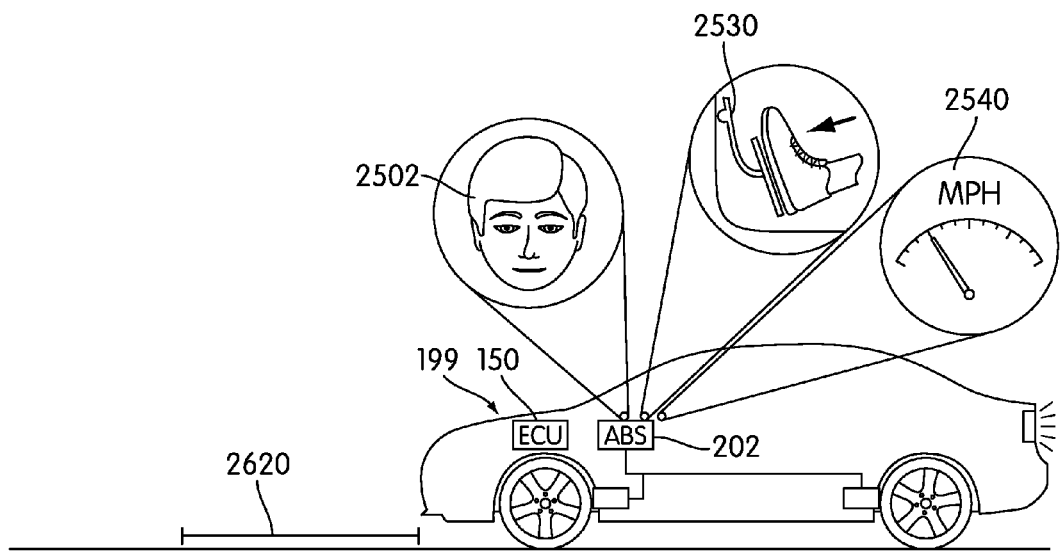
FIG. 37 is a schematic view of an embodiment of a method of modifying the operation of the antilock braking system of FIG. 36 when the driver is drowsy.

FIGS. 36 and 37 illustrate schematic views of the operation of an antilock braking system. Referring to FIG. 36, when driver 2502 is fully awake, ABS system 224 may be associated with first stopping distance 2520. In particular, for a particular initial speed 2540, as driver 2502 depresses brake pedal 2530, motor vehicle 100 may travel to first stopping distance 2520 before coming to a complete stop. This first stopping distance 2520 may be the result of various operating parameters of ABS system 224.

Referring now to FIG. 37, as driver 2502 becomes drowsy, response system 199 may modify the control of ABS system 224. In particular, in some cases, one or more operating parameters of ABS system 224 may be changed to decrease the stopping distance. In this case, as driver 2502 depresses brake pedal 2530, motor vehicle 100 may travel to second stopping distance 2620 before coming to a complete stop. In one embodiment, second stopping distance 2620 may be substantially shorter than first stopping distance 2520. In other words, the stopping distance may be decreased when driver 2502 is drowsy. Since a drowsy driver may engage the brake pedal later due to a reduced awareness, the ability of response system 199 to decrease the stopping distance may help compensate for the reduced reaction time of the driver. In another embodiment, if the vehicle is on a slippery surface the reduction in stopping may not occur and instead tactile feedback may be applied through the brake pedal.

Figure 38:
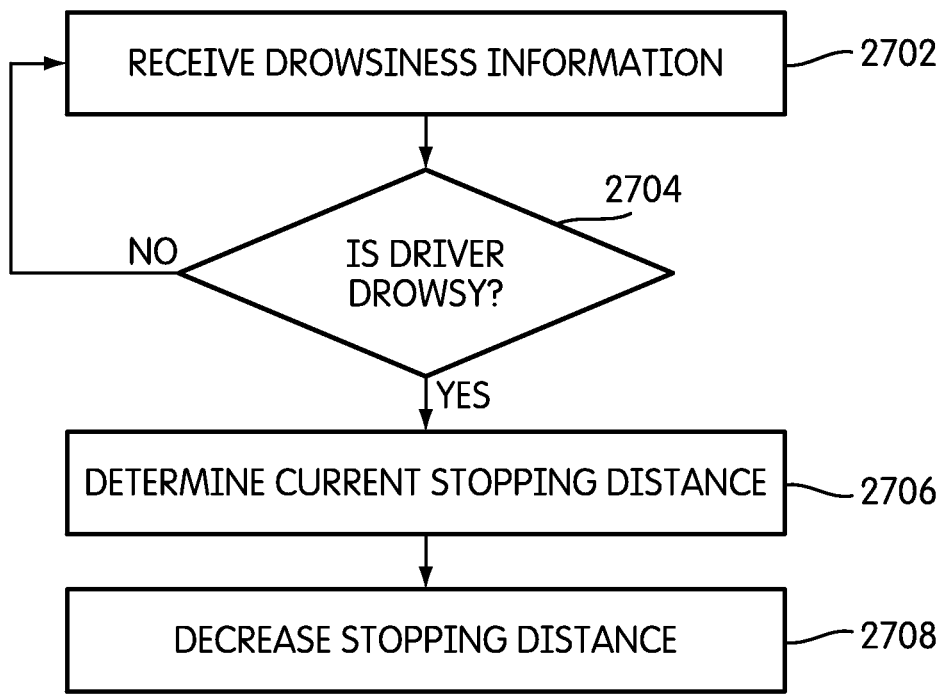
FIG. 38 is an embodiment of a process of modifying the operation of an antilock braking system according to driver behavior.

FIG. 38 illustrates an embodiment of a process for modifying the control of an antilock braking system according to the behavior of a driver. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 2702, response system 199 may receive drowsiness information. In step 2704, response system 199 may determine if the driver is drowsy. If the driver is not drowsy, response system 199 returns to step 2702. If the driver is drowsy, response system 199 may proceed to step 2706. In step 2706, response system 199 may determine the current stopping distance. The current stopping distance may be a function of the current vehicle speed, as well as other operating parameters including various parameters associated with the brake system. In step 2708, response system 199 may automatically decrease the stopping distance. This may be achieved by modifying one or more operating parameters of ABS system 224. For example, the brake line pressure can be modified by controlling various valves, pumps and/or motors within ABS system 224.

Figure 39:
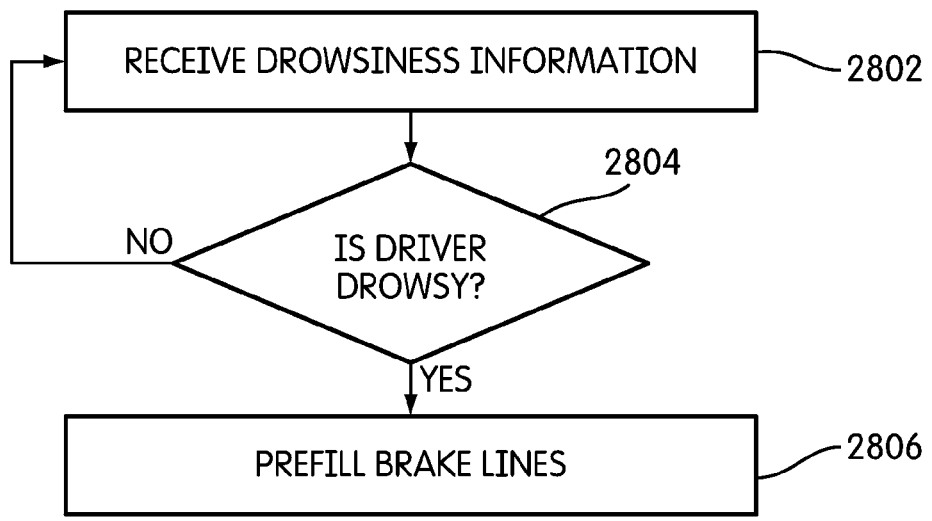
FIG. 39 is an embodiment of a process of modifying the operation of a brake system according to driver behavior.

In some embodiments, a response system can automatically prefill one or more brake lines in a motor vehicle in response to driver behavior. FIG. 39 illustrates an embodiment of a process for controlling brake lines in a motor vehicle in response to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 2802, response system 199 may receive drowsiness information. In step 2804, response system 199 may determine if the driver is drowsy. If the driver is not drowsy, response system 199 may return to step 2802. If the driver is drowsy, response system 199 may automatically prefill the brake lines with brake fluid in step 2806. For example, response system 199 may use automatic brake prefill system 228. In some cases, this may help increase braking response if a hazardous condition arises while the driver is drowsy. It will be understood that any number of brake lines could be prefilled during step 2806. Moreover, any provisions known in the art for prefilling brake lines could be used including any pumps, valves, motors or other devices needed to supply brake fluid automatically to brake lines.

Some vehicles may be equipped with brake assist systems that help reduce the amount of force a driver must apply to engage the brakes. These systems may be activated for older drivers or any other drivers who may need assistance with braking. In some cases, a response system could utilize the brake assist systems when a driver is drowsy, since a drowsy driver may not be able to apply the necessary force to the brake pedal for stopping a vehicle quickly.

Figure 40:
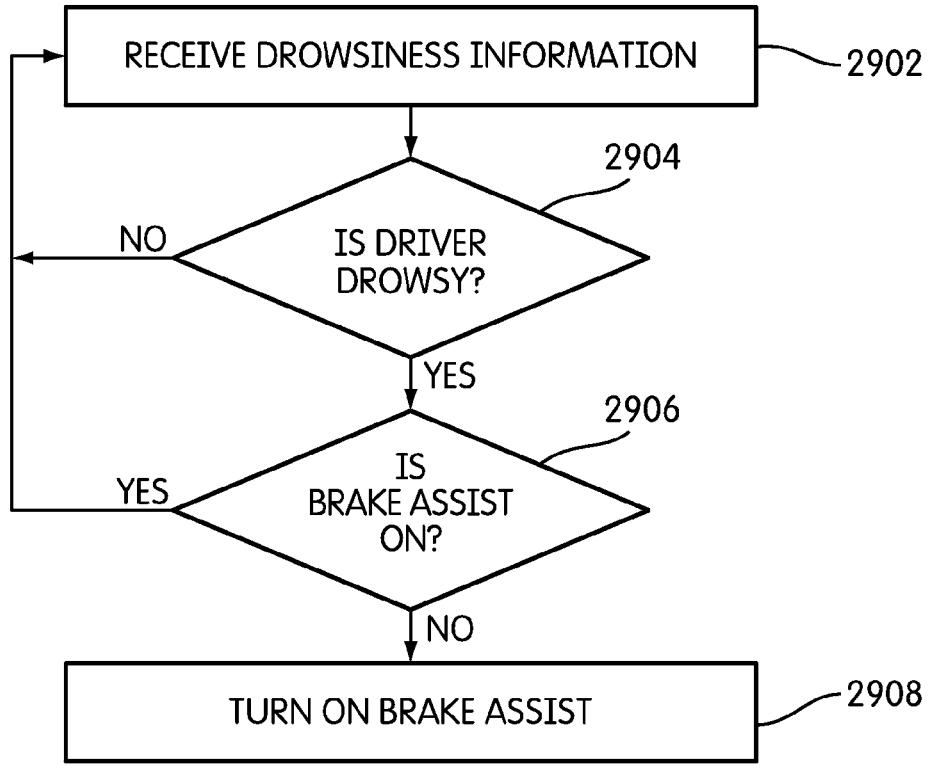
FIG. 40 is an embodiment of a process of modifying the operation of a brake assist system according to driver behavior.

FIG. 40 illustrates an embodiment of a method for controlling automatic brake assist in response to driver behavior. In step 2902, response system 199 may receive drowsiness information. In step 2904, response system 199 may determine if the driver is drowsy. If the driver is not drowsy, response system 199 proceeds back to step 2902. If the driver is drowsy, response system 199 may determine if brake assist system 226 is already on in step 2906. If brake assist system 226 is already on, response system 199 may return to step 2902. If brake assist system 226 is not currently active, response system 199 may turn on brake assist system 226 in step 2908. This arrangement allows for braking assistance to a drowsy driver, since the driver may not have sufficient ability to supply the necessary braking force in the event that motor vehicle 100 must be stopped quickly.

In some embodiments, a response system could modify the degree of assistance in a brake assist system. For example, a brake assist system may operate under normal conditions with a predetermined activation threshold. The activation threshold may be associated with the rate of change of the master cylinder brake pressure. If the rate of change of the master cylinder brake pressure exceeds the activation threshold, brake assist may be activated. However, when a driver is drowsy, the brake assist system may modify the activation threshold so that brake assist is activated sooner. In some cases, the activation threshold could vary according to the degree of drowsiness. For example, if the driver is only slightly drowsy, the activation threshold may be higher than when the driver is extremely drowsy.

Figure 41:
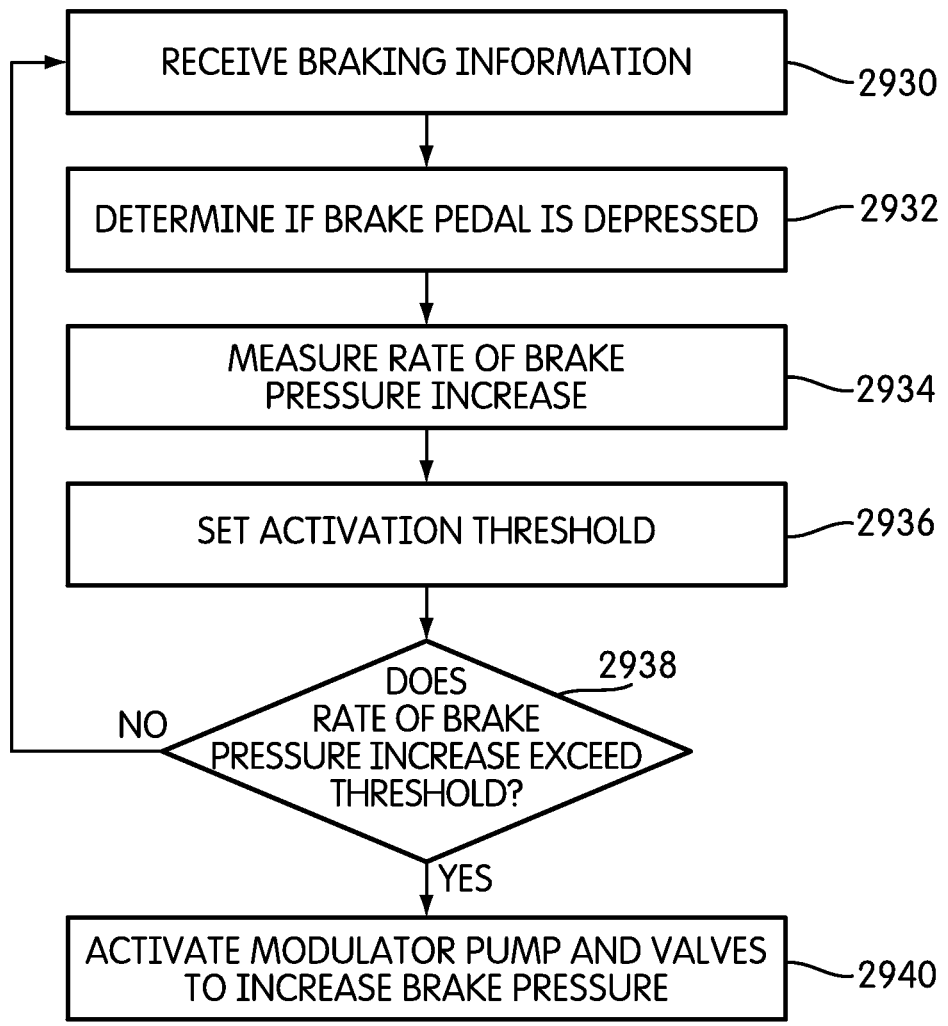
FIG. 41 is an embodiment of a process for controlling brake assist according to driver behavior.

FIG. 41 illustrates an embodiment of a detailed process for controlling automatic brake assist in response to driver behavior. In particular, FIG. 41 illustrates a method in which brake assist is modified according to the body state index of the driver. In step 2930, response system 199 may receive braking information. Braking information can include information from any sensors and/or vehicle systems. In step 2932, response system 199 may determine if a brake pedal is depressed. In some cases, response system 199 may receive information that a brake switch has been applied to determine if the driver is currently braking. In other cases, any other vehicle information can be monitored to determine if the brakes are being applied. In step 2934, response system 199 may measure the rate of brake pressure increase. In other words, response system 199 determines how fast the brake pressure is increasing, or how "hard" the brake pedal is being depressed. In step 2936, response system 199 sets an activation threshold. The activation threshold corresponds to a threshold for the rate of brake pressure increase. Details of this step are discussed in detail below.

In step 2938, response system 199 determines if the rate of brake pressure increase exceeds the activation threshold. If not, response system 199 proceeds back to step 2930. Otherwise, response system 199 proceeds to step 2940. In step 2940, response system 199 activates a modulator pump and/or valves to automatically increase the brake pressure. In other words, in step 2940, response system 199 activates brake assist. This allows for an increase in the amount of braking force applied at the wheels.

Figure 42:
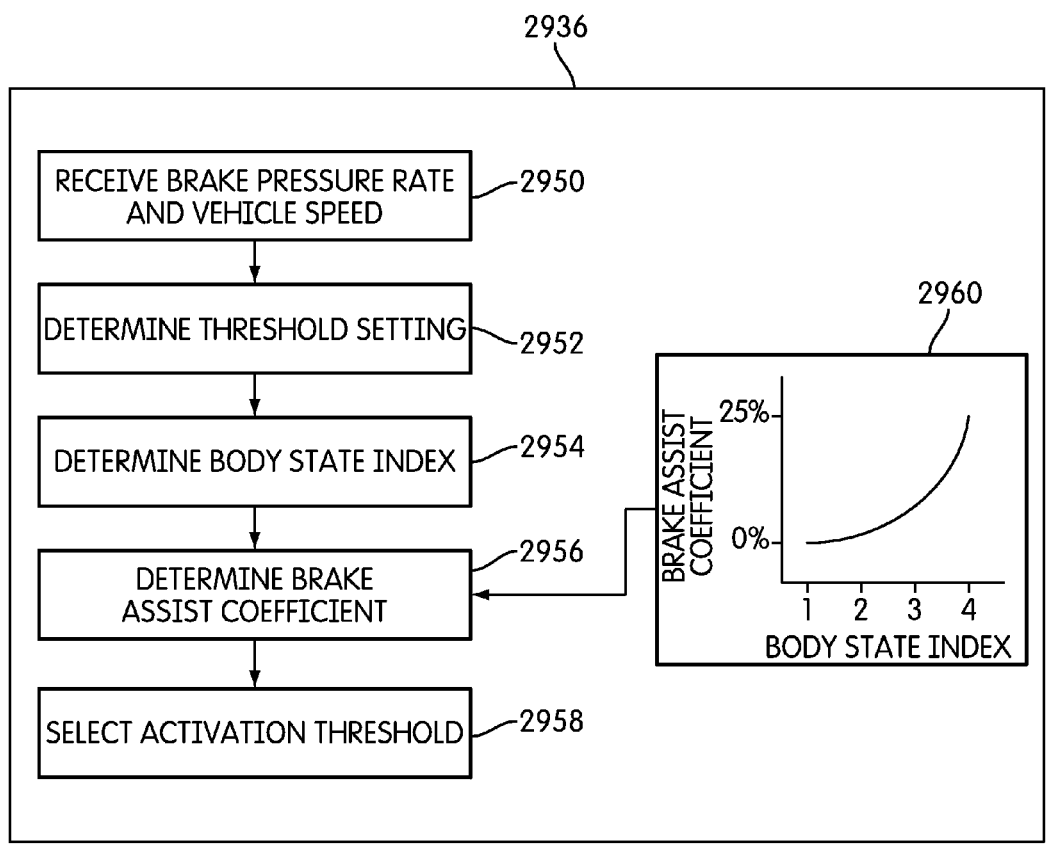
FIG. 42 is an embodiment of a process for determining an activation coefficient for brake assist.

FIG. 42 illustrates an embodiment of a process of selecting the activation threshold discussed above. In some embodiments, the process shown in FIG. 42 corresponds to step 2936 of FIG. 41. In step 2950, response system 199 may receive the brake pressure rate and vehicle speed as well as any other operating information. The brake pressure rate and vehicle speed correspond to current vehicle conditions that may be used for determining an activation threshold under normal operating conditions. In step 2952, an initial threshold setting may be determined according to the vehicle operating conditions.

In order to accommodate changes in brake assist due to drowsiness, the initial threshold setting may be modified according to the state of the driver. In step 2954, response system 199 determines the body state index of the driver using any method discussed above. Next, in step 2956, response system 199 determines a brake assist coefficient. As seen in look-up table 2960, the brake assist coefficient may vary between 0% and 25% according to the body state index. Moreover, the brake assist coefficient generally increases as the body state index increases. In step 2958, the activation threshold is selected according to the initial threshold setting and the brake assist coefficient. If the brake assist coefficient has a value of 0%, the activation threshold is just equal to the initial threshold setting. However, if the brake assist coefficient has a value of 25%, the activation threshold may be modified by up to 25% in order to increase the sensitivity of the brake assist when the driver is drowsy. In some cases, the activation threshold may be increased by up to 25% (or any other amount corresponding to the brake assist coefficient). In other cases, the activation threshold may be decreased by up to 25% (or any other amount corresponding to the brake assist coefficient).

A motor vehicle can include provisions for increasing vehicle stability when a driver is drowsy. In some cases, a response system can modify the operation of an electronic stability control system. For example, in some cases, a response system could ensure that a detected yaw rate and a steering yaw rate (the yaw rate estimated from steering information) are very close to one another. This can help enhance steering precision and reduce the likelihood of hazardous driving conditions while the driver is drowsy.

Figure 43:
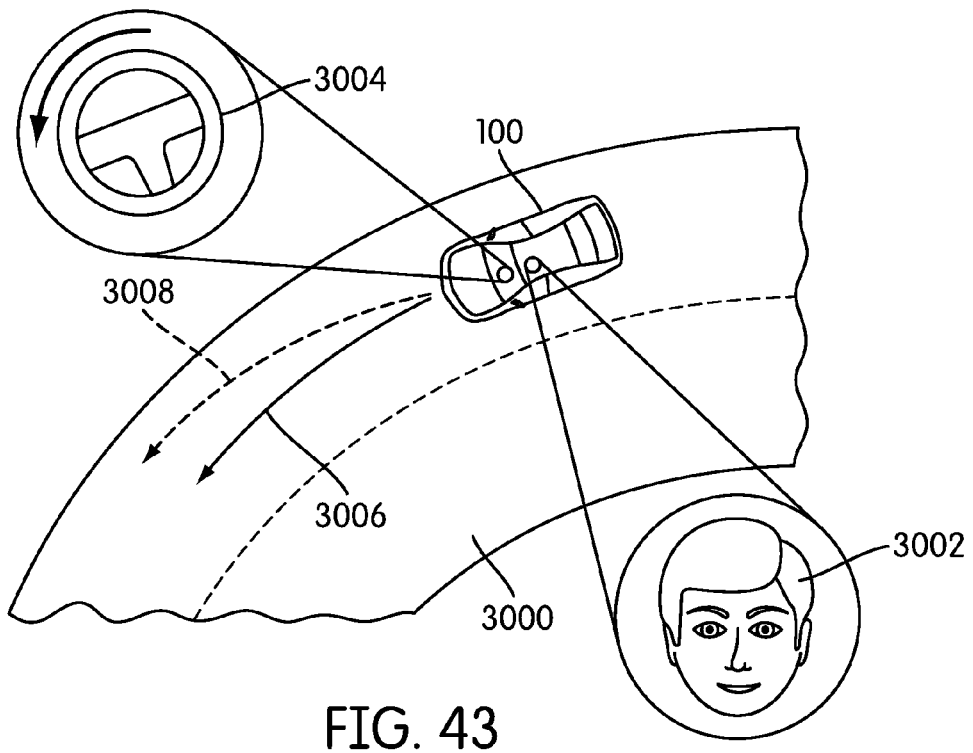
FIG. 43 is a schematic view of an embodiment of a motor vehicle operating with an electronic stability control system.
Figure 44:
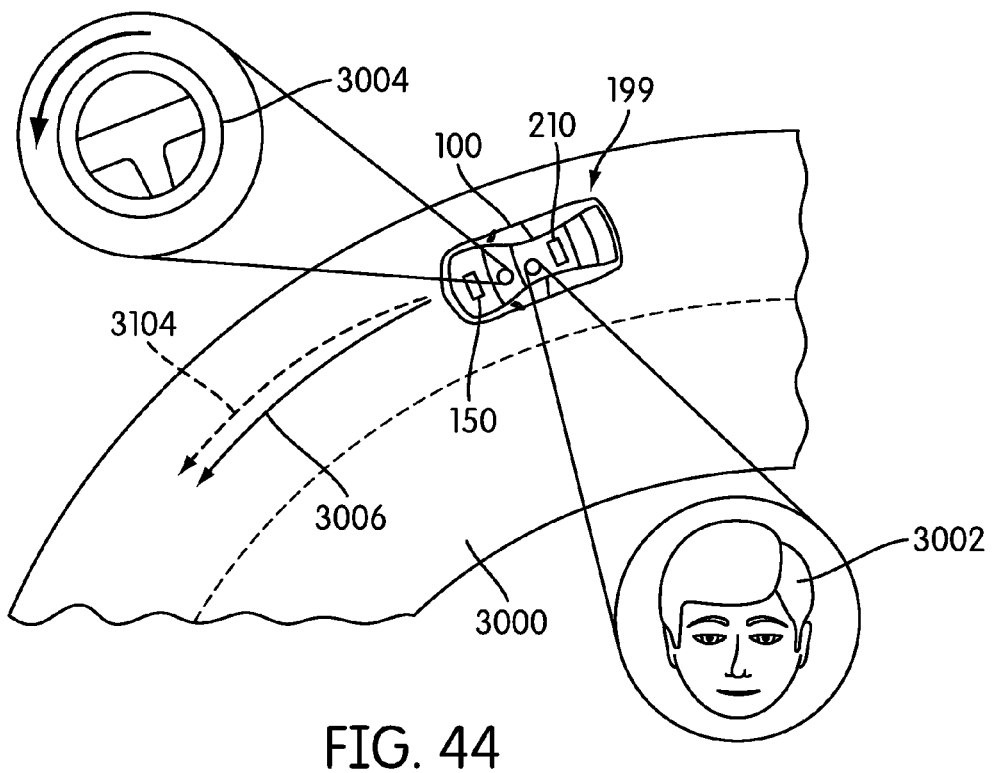
FIG. 44 is a schematic view of an embodiment of a method of modifying the operation of the electronic control assist system of FIG. 43 when the driver is drowsy.

FIGS. 43 and 44 are schematic views of an embodiment of motor vehicle 100 turning around a curve in roadway 3000. Referring to FIG. 43, driver 3002 is wide awake and turning steering wheel 3004. Also shown in FIG. 43 are the driver intended path 3006 and the actual vehicle path 3008. The driver intended path may be determined from steering wheel information, yaw rate information, lateral g information as well as other kinds of operating information. The driver intended path represents the ideal path of the vehicle, given the steering input from the driver. However, due to variations in road traction as well as other conditions, the actual vehicle path may vary slightly from the driver intended path. Referring to FIG. 44, as driver 3002 gets drowsy, response system 199 modifies the operation of electronic stability control system 222. In particular, ESC system 222 is modified so that the actual vehicle path 3104 is closer to the driver intended path 3006. This helps to minimize the difference between the driver intended path and the actual vehicle path when the driver is drowsy, which can help improve driving precision.

Figure 45:
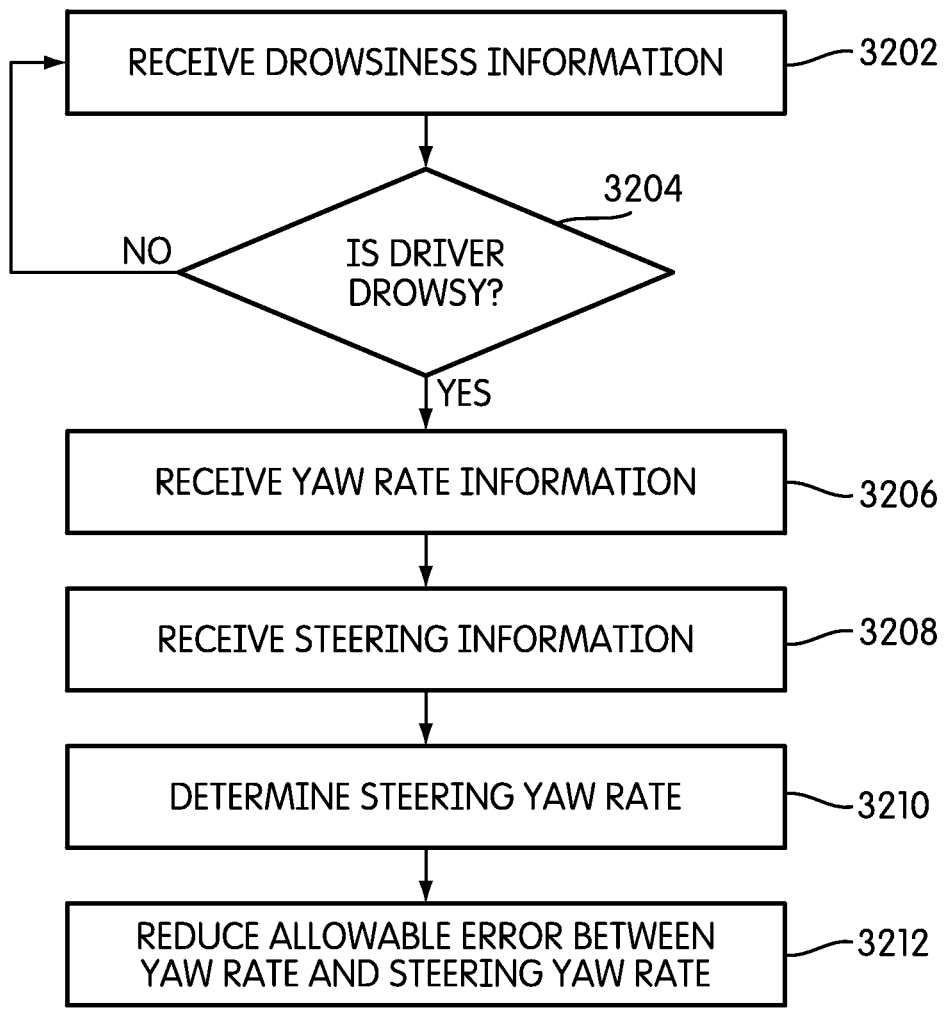
FIG. 45 is an embodiment of a process of modifying the operation of an electronic stability control system according to driver behavior.

FIG. 45 illustrates an embodiment of a process for controlling an electronic vehicle stability system according to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 3202, response system 199 may receive drowsiness information. In step 3204, response system 199 determines if the driver is drowsy. If the driver is not drowsy, response system 199 may return to step 3202. Otherwise, response system 199 receives yaw rate information in step 3206. The yaw rate information could be received from a yaw rate sensor in some cases. In step 3208, response system 199 receives steering information. This could include, for example, the steering wheel angle received from a steering angle sensor. In step 3210, response system 199 determines the steering yaw rate using the steering information. In some cases, additional operating information could be used to determine the steering yaw rate. In step 3212, response system 199 may reduce the allowable error between the measured yaw rate and the steering yaw rate. In other words, response system 199 helps minimize the difference between the driver intended path and the actual vehicle path.

In order to reduce the allowable error between the yaw rate and the steering yaw rate, response system 199 may apply braking to one or more brakes of motor vehicle 100 in order to maintain motor vehicle 100 close to the driver intended path. Examples of maintaining a vehicle close to a driver intended path can be found in Ellis et al., U.S. Publication No. 2011/0231052, the entirety of which is hereby incorporated by reference.

Figure 46:
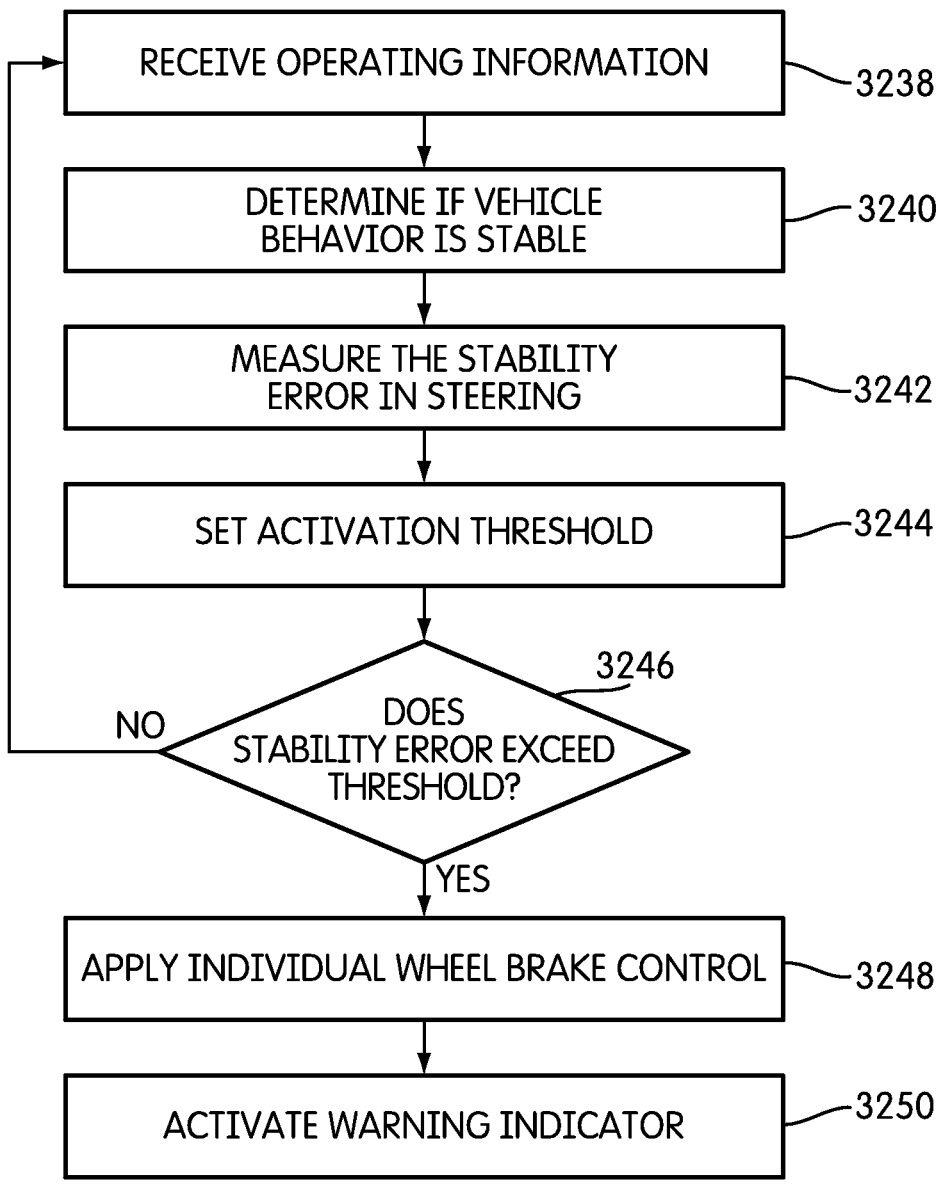
FIG. 46 is an embodiment of a process for controlling an electronic stability control system in response to driver behavior.

FIG. 46 illustrates an embodiment of a process for controlling an electronic stability control system in response to driver behavior. In particular, FIG. 46 illustrates an embodiment in which the operation of the electronic stability control system is modified according to the body state index of the driver. In step 3238, response system 199 receives operating information. This information can include any operating information such as yaw rate, wheel speed, steering angles, as well as other information used by an electronic stability control system. In step 3240, response system 199 may determine if the vehicle behavior is stable. In particular, in step 3242, response system 199 measures the stability error of steering associated with under-steering or over-steering. In some cases, the stability is determined by comparing the actual path of the vehicle with the driver intended path.

In step 3244, response system 199 sets an activation threshold associated with the electronic stability control system. The activation threshold may be associated with a predetermined stability error. In step 3246, response system 199 determines if the stability error exceeds the activation threshold. If not, response system 199 may return to step 3238. Otherwise, response system 199 may proceed to step 3248. In step 3248, response system 199 applies individual wheel brake control in order to increase vehicle stability. In some embodiments, response system 199 could also control the engine to apply engine braking or modify cylinder operation in order to help stabilize the vehicle.

In some cases, in step 3250, response system 199 may activate a warning indicator. The warning indicator could be any dashboard light or message displayed on a navigation screen or other video screen. The warning indicator helps to alert a driver that the electronic stability control system has been activated. In some cases, the warning could be an audible warning and/or a haptic warning.

Figure 47:
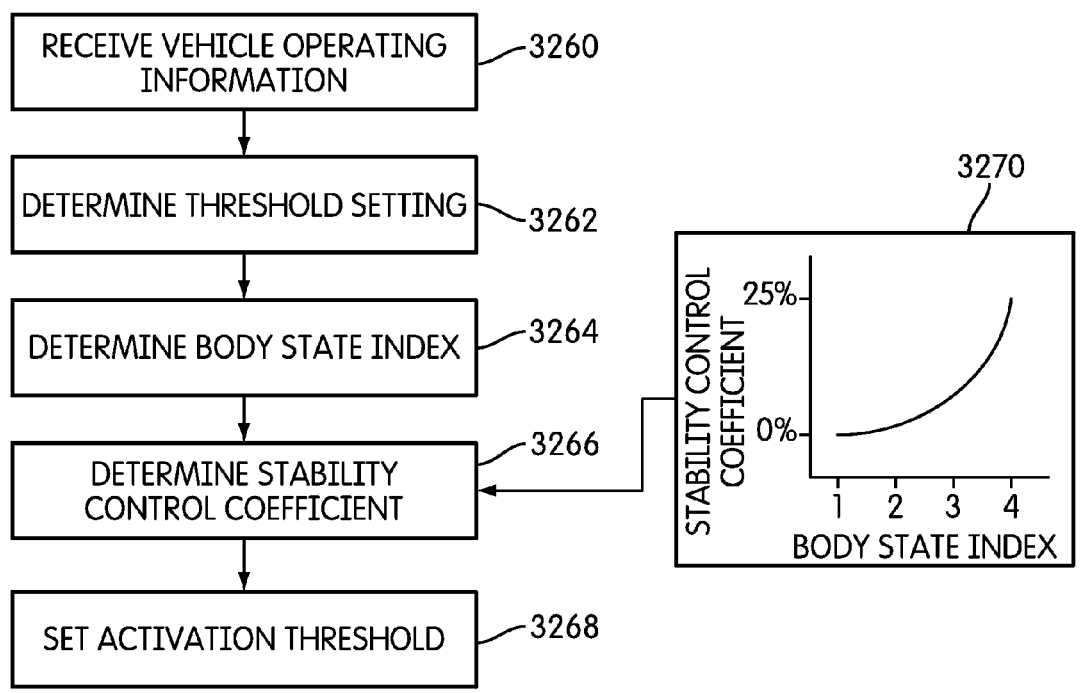
FIG. 47 is an embodiment of a process for setting an activation threshold for an electronic stability control system.

FIG. 47 illustrates an embodiment of a process for setting the activation threshold used in the previous method. In step 3260, response system 199 receives vehicle operating information. For example, the vehicle operating information can include wheel speed information, road surface conditions (such as curvature, friction coefficients, etc.), vehicle speed, steering angle, yaw rate as well as other operating information. In step 3262, response system 199 determines an initial threshold setting according to the operating information received in step 3260. In step 3264, response system 199 determines the body state index of the driver.

In step 3266, response system 199 determines a stability control coefficient. As seen in look-up table 3270, the stability control coefficient may be determined from the body state index. In one example, the stability control coefficient ranges from 0% to 25%. Moreover, the stability control coefficient generally increases with the body state index. For example, if the body state index is 1, the stability control coefficient is 0%. If the body state index is 4, the stability control coefficient is 25%. It will be understood that these ranges for the stability control coefficient are only intended to be exemplary and in other cases the stability control coefficient could vary in any other manner as a function of the body state index.

In step 3268, response system 199 may set the activation threshold using the initial threshold setting and the stability control coefficient. For example, if the stability control coefficient has a value of 25%, the activation threshold may be up to 25% larger than the initial threshold setting. In other cases, the activation threshold may be up to 25% smaller than the initial threshold setting. In other words, the activation threshold may be increased or decreased from the initial threshold setting in proportion to the value of the stability control coefficient. This arrangement helps to increase the sensitivity of the electronic stability control system by modifying the activation threshold in proportion to the state of the driver.

Figure 48:
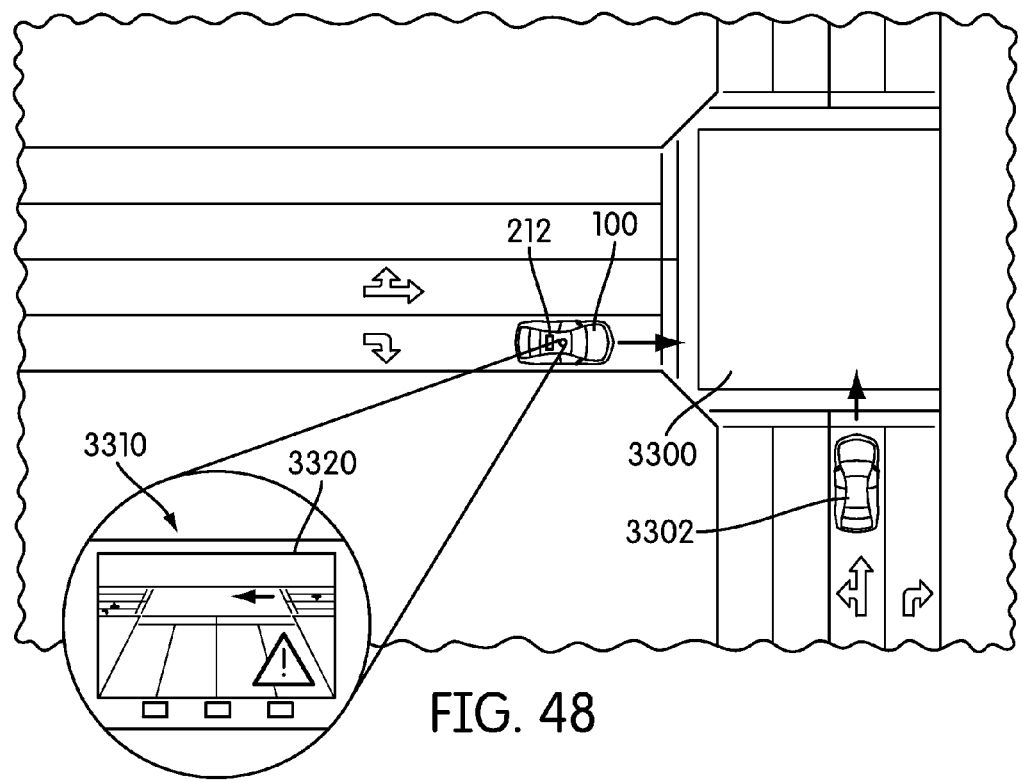
FIG. 48 is a schematic view of an embodiment of a motor vehicle equipped with a collision warning system.

FIG. 48 illustrates a schematic view of motor vehicle 100 equipped with a collision warning system 234. Collision warning system 234 can function to provide warnings about potential collisions to a driver. For purposes of clarity, the term "host vehicle" as used throughout this detailed description and in the claims refers to any vehicle including a response system while the term "target vehicle" refers to any vehicle monitored by, or otherwise in communication with, a host vehicle. In the current embodiment, for example, motor vehicle 100 may be a host vehicle. In this example, as motor vehicle 100 approaches intersection 3300 while target vehicle 3302 passes through intersection 3300, collision warning system 234 may provide warning alert 3310 on display screen 3320. Further examples of collision warning systems are disclosed in Mochizuki, U.S. Publication No. 2012/0068859, and Mochizuki et al., U.S. Publication No. 2012/0025965, the entirety of both being hereby incorporated by reference.

Figure 49:
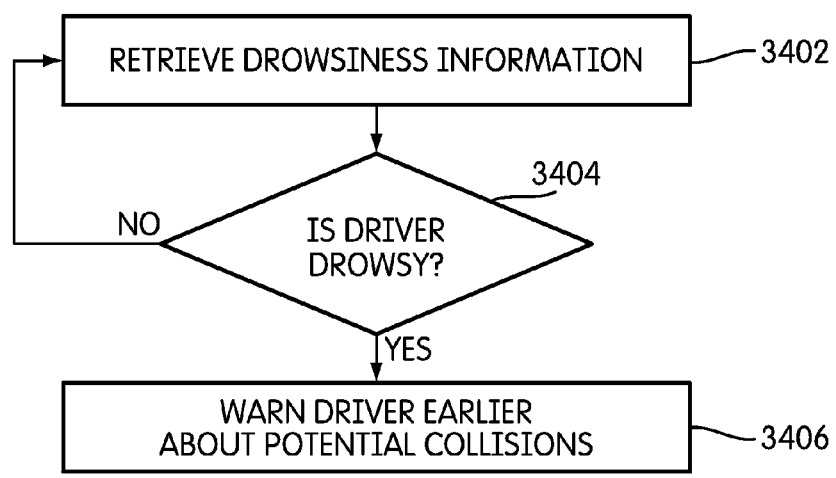
FIG. 49 is an embodiment of a process of modifying the control of a collision warning system according to driver behavior.

FIG. 49 illustrates an embodiment of a process for modifying a collision warning system according to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 3402, response system 199 my receive drowsiness information. In step 3404, response system 199 may determine if the driver is drowsy. If the driver is not drowsy, response system 199 may proceed back to step 3402. Otherwise, response system 199 may proceed to step 3406. In step 3406, response system 199 may modify the operation of a collision warning system so that the driver is warned earlier about potential collisions. For example, if the collision warning system was initially set to warn a driver about a potential collision if the distance to the collision point is less than 25 meters, response system 199 could modify the system to warn the driver if the distance to the collision point is less than 50 meters.

Figure 50:
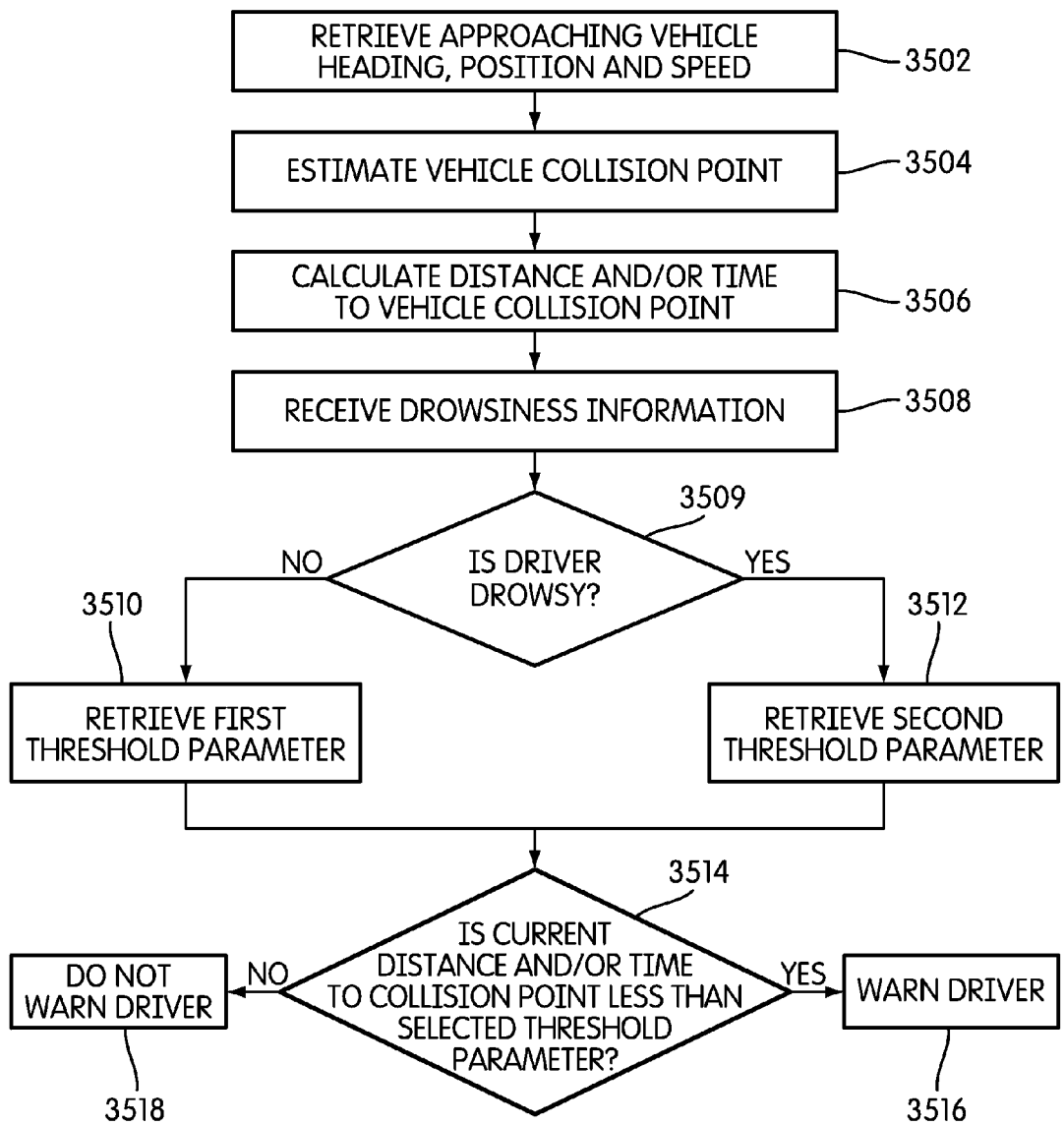
FIG. 50 is an embodiment of a detailed process of modifying the control of a collision warning system according to driver behavior.

FIG. 50 illustrates an embodiment of a process for modifying a collision warning system according to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 3502, collision warning system 234 may retrieve the heading, position and speed of an approaching vehicle. In some cases, this information could be received from the approaching vehicle through a wireless network, such as a DSRC network. In other cases, this information could be remotely sensed using radar, lidar or other remote sensing devices.

In step 3504, collision warning system 234 may estimate a vehicle collision point. The vehicle collision point is the location of a potential collision between motor vehicle 100 and the approaching vehicle, which could be traveling in any direction relative to motor vehicle 100. In some cases, in step 3504, collision warning system 234 may use information about the position, heading and speed of motor vehicle 100 to calculate the vehicle collision point. In some embodiments, this information could be received from a GPS receiver that is in communication with collision warning system 234 or response system 199. In other embodiments, the vehicle speed could be received from a vehicle speed sensor.

In step 3506, collision warning system 234 may calculate the distance and/or time to the vehicle collision point. In particular, to determine the distance, collision warning system 234 may calculate the difference between the vehicle collision point and the current location of motor vehicle 100. Likewise, to determine the time to collision warning system 234 could calculate the amount of time it will take to reach the vehicle collision point.

In step 3508, collision warning system 234 may receive drowsiness information from response system 199, or any other system or components. In step 3509, collision warning system 234 may determine if the driver is drowsy. If the driver is not drowsy, collision warning system 234 may proceed to step 3510, where a first threshold parameter is retrieved. If the driver is drowsy, collision warning system 234 may proceed to step 3512, where a second threshold distance is retrieved. The first threshold parameter and the second threshold parameter could be either time thresholds or distance thresholds, according to whether the time to collision or distance to collision was determined during step 3506. In some cases, where both time and distance to the collision point are used, the first threshold parameter and the second threshold parameter can each comprise both a distance threshold and a time threshold. Moreover, it will be understood that the first threshold parameter and the second threshold parameter may be substantially different thresholds in order to provide a different operating configuration for collision warning system 234 according to whether the driver is drowsy or not drowsy. Following both step 3510 and 3512, collision warning system 234 proceeds to step 3514. In step 3514, collision warning system 234 determines if the current distance and/or time to the collision point is less than the threshold parameter selected during the previous step (either the first threshold parameter or the second threshold parameter).

The first threshold parameter and the second threshold parameter could have any values. In some cases, the first threshold parameter may be less than the second threshold parameter. In particular, if the driver is drowsy, it may be beneficial to use a lower threshold parameter, since this corresponds to warning a driver earlier about a potential collision. If the current distance or time is less than the threshold distance or time (the threshold parameter), collision warning system 234 may warn the driver in step 3516. Otherwise, collision warning system 234 may not warn the driver in step 3518.

A response system can include provisions for modifying the operation of an auto cruise control system according to driver behavior. In some embodiments, a response system can change the headway distance associated with an auto cruise control system. In some cases, the headway distance is the closest distance a motor vehicle can get to a preceding vehicle. If the auto cruise control system detects that the motor vehicle is closer than the headway distance, the system may warn the driver and/or automatically slow the vehicle to increase the headway distance.

Figure 51:
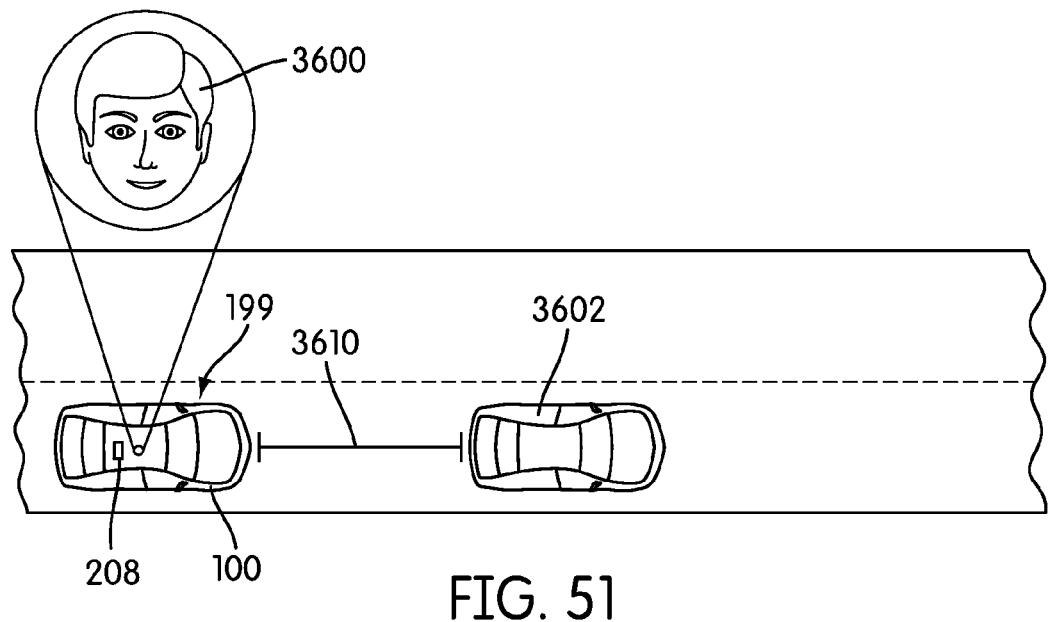
FIG. 51 is a schematic view of an embodiment of a motor vehicle operating with an auto cruise control system.
Figure 52:
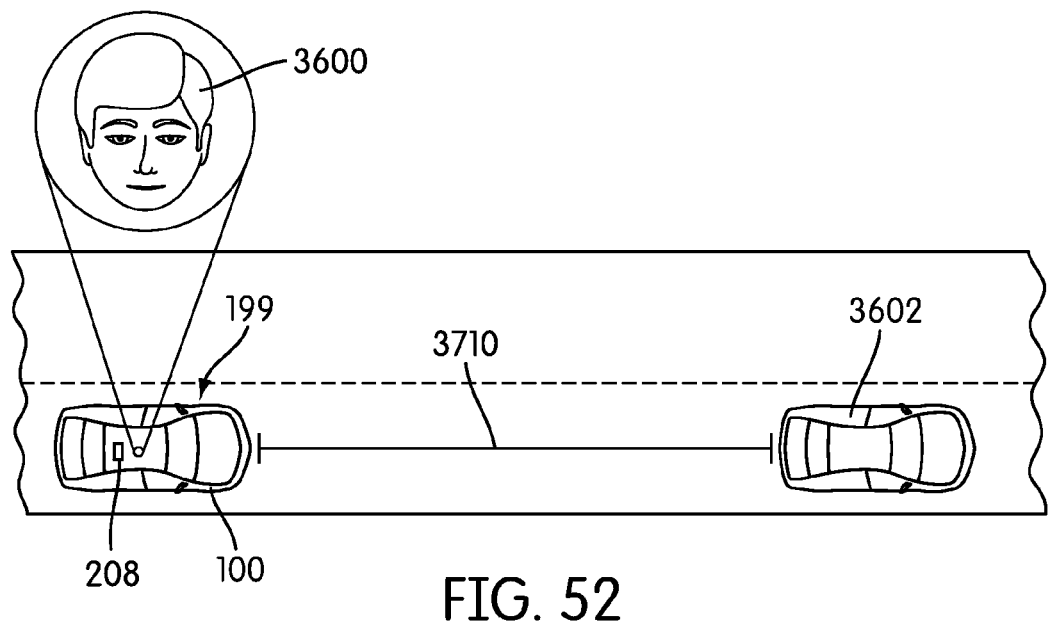
FIG. 52 is a schematic view of an embodiment of a method of modifying the control of the auto cruise control system of FIG. 51 according to driver behavior.

FIGS. 51 and 52 illustrate schematic views of motor vehicle 100 cruising behind preceding vehicle 3602. In this situation, auto cruise control system 238 is operating to automatically maintain a predetermined headway distance behind preceding vehicle 3602. When driver 3600 is awake, auto cruise control system 238 uses a first headway distance 3610, as seen in FIG. 51. In other words, auto cruise control system 238 automatically prevents vehicle 100 from getting closer than first headway distance 3610 to preceding vehicle 3602. As driver 3600 becomes drowsy, as seen in FIG. 52, response system 199 may modify the operation of auto cruise control system 238 so that auto cruise control system 238 increases the headway distance to second headway distance 3710. Second headway distance 3710 may be substantially larger than first headway distance 3610, since the reaction time of driver 3600 may be reduced when driver 3600 is drowsy.

Figure 53:
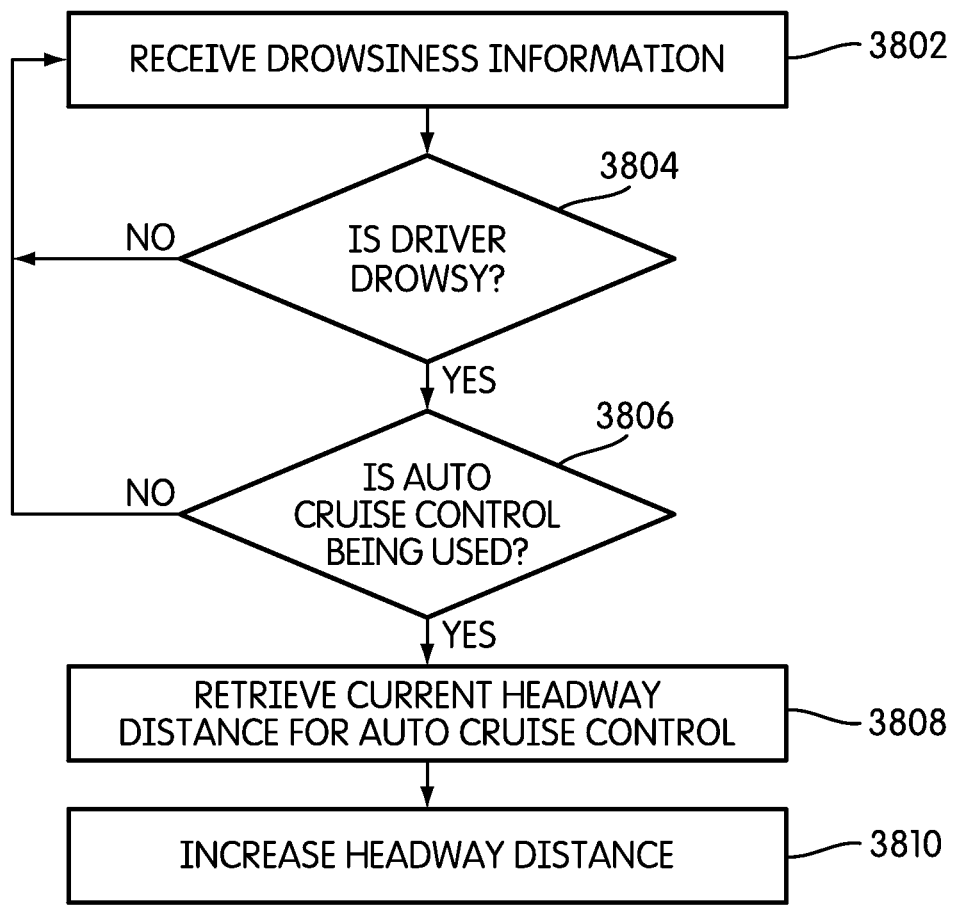
FIG. 53 is an embodiment of a process of modifying the control of an auto cruise control system according to driver behavior.

FIG. 53 illustrates an embodiment of a method of modifying the control of an auto cruise control system according to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 3802, response system 199 may receive drowsiness information. In step 3804, response system 199 may determine if the driver is drowsy. If the driver is not drowsy, response system 199 may return to step 3802. If the driver is drowsy, response system 199 may proceed to step 3806. In step 3806, response system 199 may determine if auto cruise control is being used. If not, response system 199 may return back to step 3802. If auto cruise control is being used, response system 199 may proceed to step 3808. In step 3808, response system 199 may retrieve the current headway distance for auto cruise control. In step 3810, response system 199 may increase the headway distance. With this arrangement, response system 199 may help increase the distance between motor vehicle 100 and other vehicles when a driver is drowsy to reduce the chances of a hazardous driving situation while the driver is drowsy.

Figure 54:
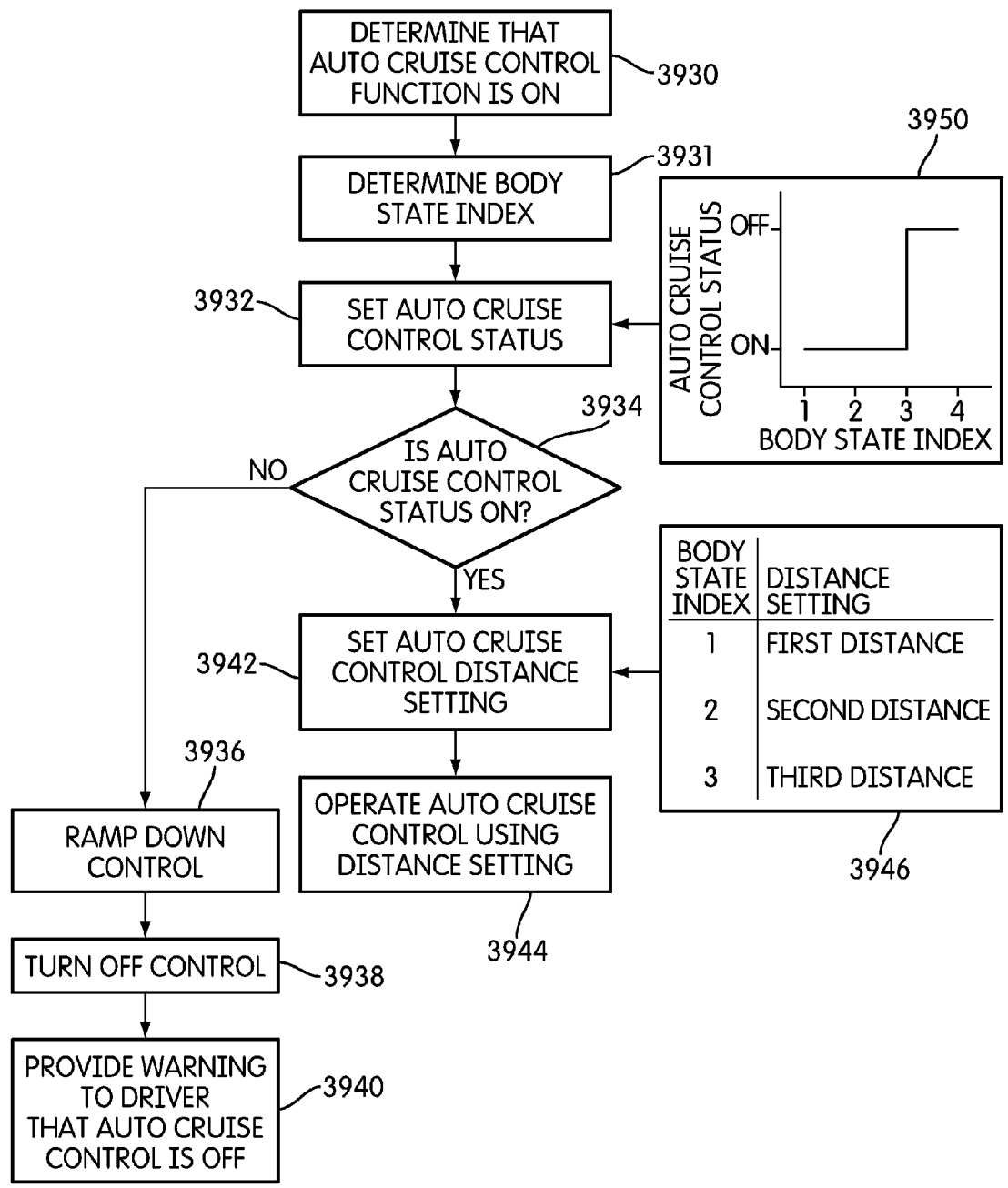
FIG. 54 is an embodiment of a process of modifying operation of an automatic cruise control system in response to driver behavior.

FIG. 54 illustrates an embodiment of a process for controlling automatic cruise control in response to driver behavior. This embodiment could also apply to normal cruise control systems. In particular, FIG. 54 illustrates an embodiment of a process where the operation of an automatic cruise control system is varied in response to the body state index of a driver. In step 3930, response system 199 may determine that the automatic cruise control function is turned on. This may occur when a driver selects to turn on cruise control. In step 3931, response system 199 may determine the body state index of the driver using any method discussed above as well as any method known in the art. In step 3932, response system 199 may set the auto cruise control status based on the body state index of the driver. For example, look-up table 3950 indicates that the auto cruise control status is set to on for body state indexes of 1, 2 and 3. Also, the auto cruise control status is set to off for body state index of 4. In other embodiments, the auto cruise control status can be set according to body state index in any other manner.

In step 3934, response system 199 determines if the auto cruise control status is on. If so, response system 199 proceeds to step 3942. Otherwise, if the auto cruise control status is off, response system 199 proceeds to step 3936. In step 3936, response system 199 ramps down control of automatic cruise control. For example, in some cases response system 199 may slow down the vehicle gradually to a predetermined speed. In step 3938, response system 199 may turn off automatic cruise control. In some cases, in step 3940, response system 199 may inform the driver that automatic cruise control has been deactivated using a dashboard warning light or message displayed on a screen of some kind. In other cases, response system 199 could provide an audible warning that automatic cruise control has been deactivated. In still other cases a haptic warning could be used.

If the auto cruise control status is determined to be on during step 3934, response system 199 may set the auto cruise control distance setting in step 3942. For example, look-up table 3946 provides one possible configuration for a look-up table relating the body state index to a distance setting. In this case, a body state index of 1 corresponds to a first distance, a body state index of 2 corresponds to a second distance and a body state index of 3 corresponds to a third distance. Each distance may have a substantially different value. In some cases, the value of each headway distance may increase as the body state index increases in order to provide more headway room for drivers who are drowsy or otherwise inattentive. In step 3944, response system 199 may operate auto cruise control using the distance setting determined during step 3942.

Figure 55:
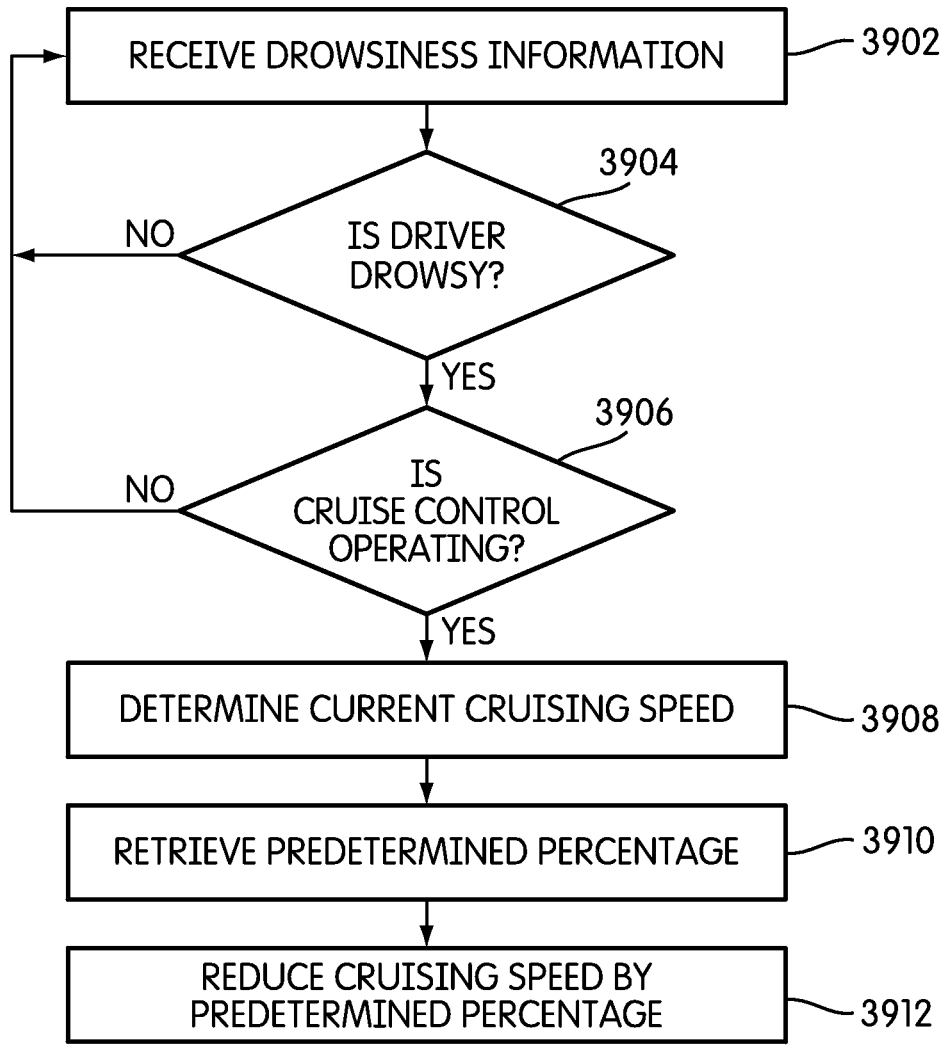
FIG. 55 is an embodiment of a process of modifying a cruising speed of a vehicle according to driver behavior.

A response system can include provisions for automatically reducing a cruising speed in a cruise control system based on driver monitoring information. FIG. 55 illustrates an embodiment of a method for controlling a cruising speed. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 3902, response system 199 may receive drowsiness information. In step 3904, response system 199 may determine if the driver is drowsy. If the driver is not drowsy, response system 199 returns to step 3902, otherwise response system 199 proceeds to step 3906. In step 3906, response system 199 determines if cruise control is operating. If not, response system 199 returns back to step 3902. If cruise control is operating, response system 199 determines the current cruising speed in step 3908. In step 3910, response system 199 retrieves a predetermined percentage. The predetermined percentage could have any value between 0% and 100%. In step 3912, response system 199 may reduce the cruising speed by the predetermined percentage. For example, if motor vehicle 100 is cruising at 60 mph and the predetermined percentage is 50%, the cruising speed may be reduced to 30 mph. In other embodiments, the cruising speed could be reduced by a predetermined amount, such as by 20 mph or 30 mph. In still other embodiments, the predetermined percentage could be selected from a range of percentages according to the driver body index. For example, if the driver is only slightly drowsy, the predetermined percentage could be smaller than the percentage used when the driver is very drowsy. Using this arrangement, response system 199 may automatically reduce the speed of motor vehicle 100, since slowing the vehicle may reduce the potential risks posed by a drowsy driver.

Figure 56:
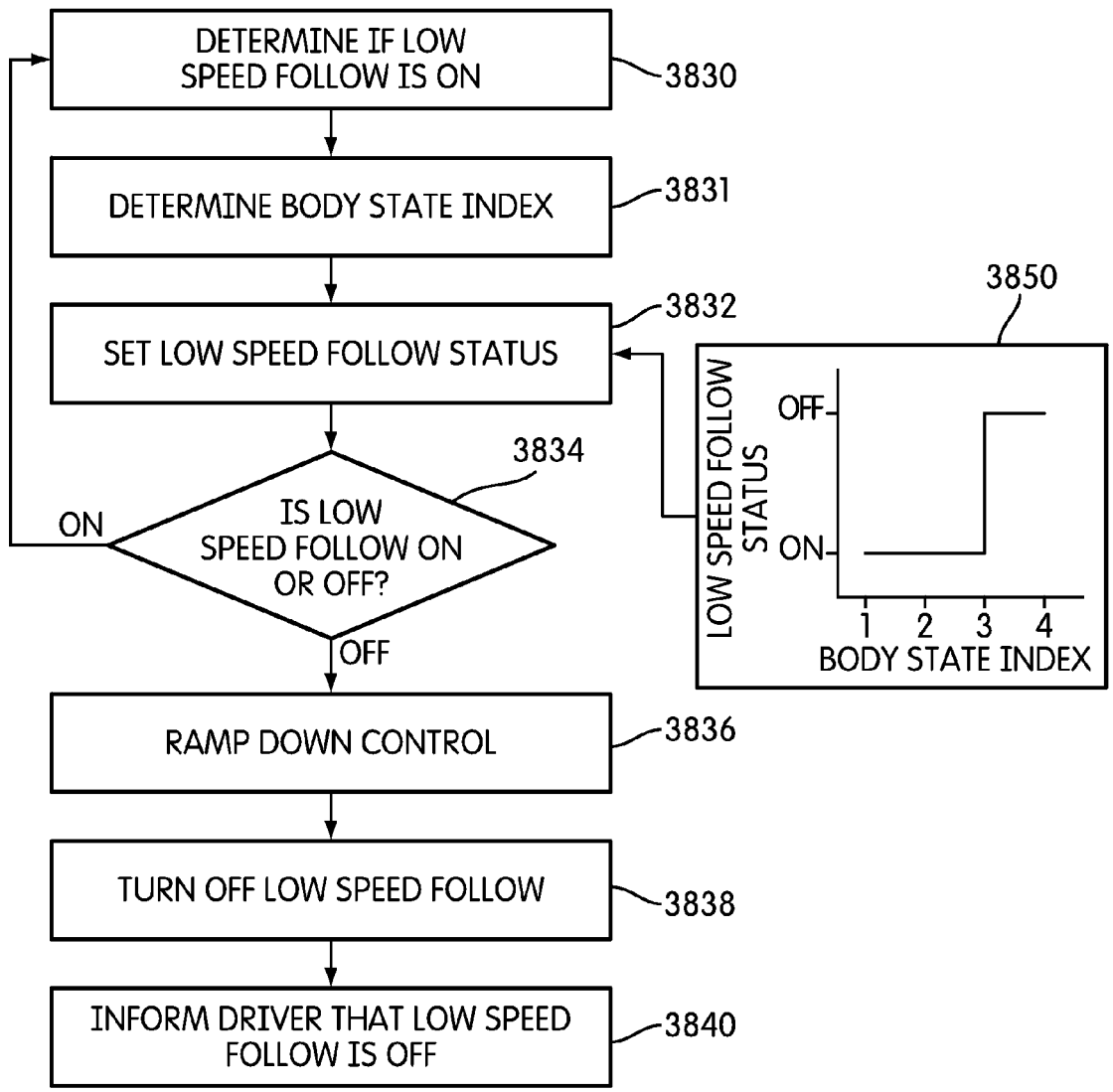
FIG. 56 is an embodiment of a process for controlling a low speed follow function associated with cruise control.

FIG. 56 illustrates an embodiment of a process for controlling a low speed follow system in response to driver behavior. In step 3830, response system 199 may determine if the low speed follow system is on. "Low speed follow" refers to any system that is used for automatically following a preceding vehicle at low speeds.

In step 3831, response system 199 may determine the body state index of the driver. Next, in step 3832, response system 199 may set the low speed follow status based on the body state index of the driver. For example, look-up table 3850 shows an exemplary relationship between body state index and the low speed follow status. In particular, the low speed follow status varies between an "on" state and an "off" state. For low body state index (body state indexes of 1 or 2) the low speed follow status may be set to "on". For high body state index (body state indexes of 3 or 4) the low speed follow status may be set to "off". It will be understood that the relationship between body state index and low speed follow status shown here is only exemplary and in other embodiments the relationship could vary in any other manner.

In step 3834, response system 199 determines if the low speed follow status is on or off. If the low speed follow status is on, response system 199 returns to step 3830. Otherwise, response system 199 proceeds to step 3836 when the low speed follow status is off. In step 3836, response system 199 may ramp down control of the low speed follow function. For example, the low speed follow system may gradually increase the headway distance with the preceding vehicle until the system is shut down in step 3838. By automatically turning of low speed follow when a driver is drowsy, response system 199 may help increase driver attention and awareness since the driver must put more effort into driving the vehicle.

In some cases, in step 3840, response system 199 may inform the driver that low speed follow has been deactivated using a dashboard warning light or message displayed on a screen of some kind. In other cases, response system 199 could provide an audible warning that low speed follow has been deactivated.

A response system can include provisions for modifying the operation of a lane departure warning system, which helps alert a driver if the motor vehicle is unintentionally leaving the current lane. In some cases, a response system could modify when the lane departure warning system alerts a driver. For example, the lane keep departure warning system could warn the driver before the vehicle crosses a lane boundary line, rather than waiting until the vehicle has already crossed the lane boundary line.

Figure 57:
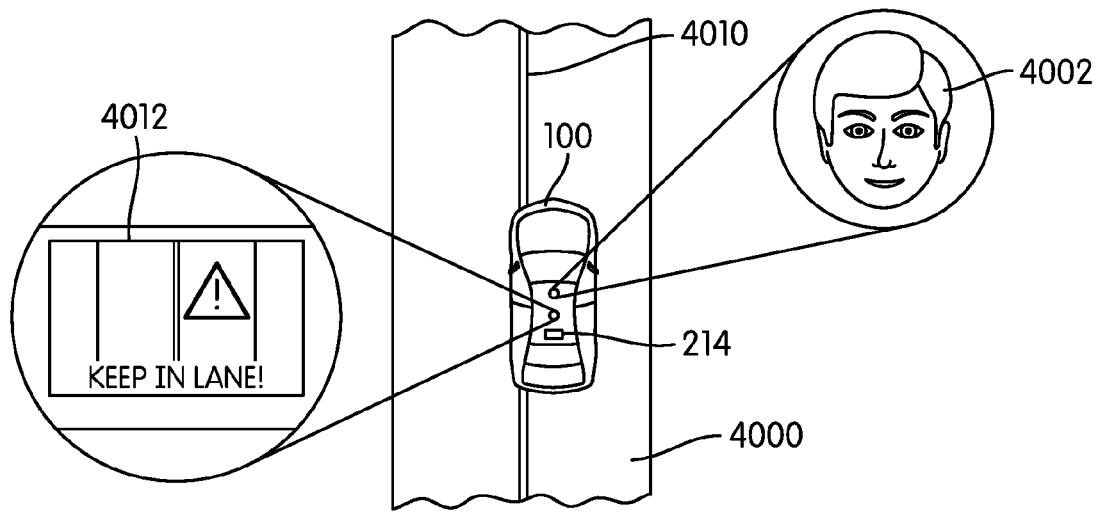
FIG. 57 is a schematic view of an embodiment of a motor vehicle operating with a lane departure warning system.
Figure 58:
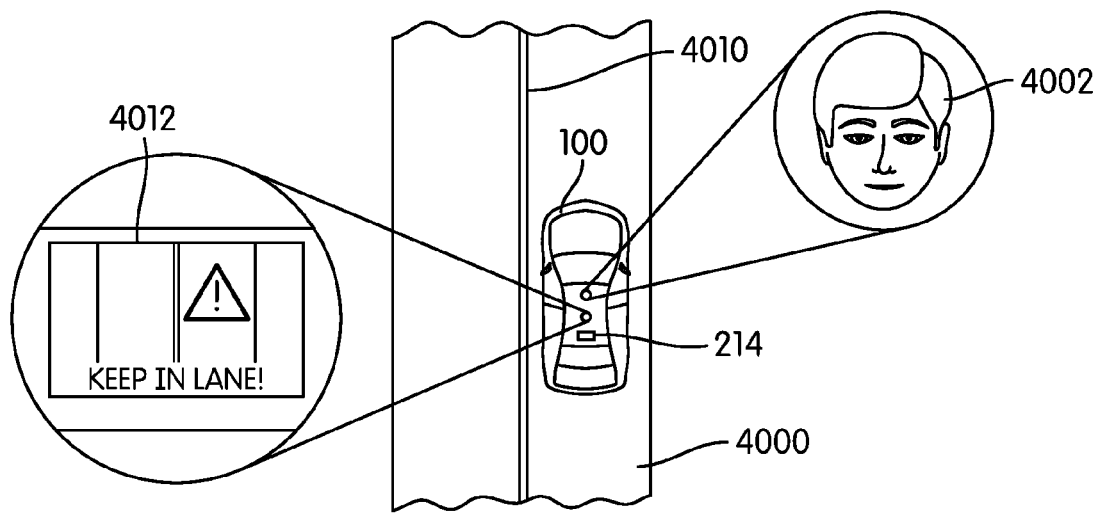
FIG. 58 is a schematic view of an embodiment of a method of modifying the control of the lane departure warning system of FIG. 57 when the driver is drowsy.

FIGS. 57 and 58 illustrate schematic views of an embodiment of a method of modifying the operation of a lane departure warning system. Referring to FIGS. 57 and 58, motor vehicle 100 travels on roadway 4000. Under circumstances where driver 4002 is fully alert (see FIG. 57), lane departure warning system 240 may wait until motor vehicle 100 crosses lane boundary line 4010 before providing warning 4012. However, in circumstances where driver 4002 is drowsy (see FIG. 58), lane departure warning system 240 may provide warning 4012 just prior to the moment when motor vehicle 100 crosses lane boundary line 4010. In other words, lane departure warning system 244 warns driver 4002 earlier when driver 4002 is drowsy. This may help improve the likelihood that driver 4002 stays inside the current lane.

Figure 59:
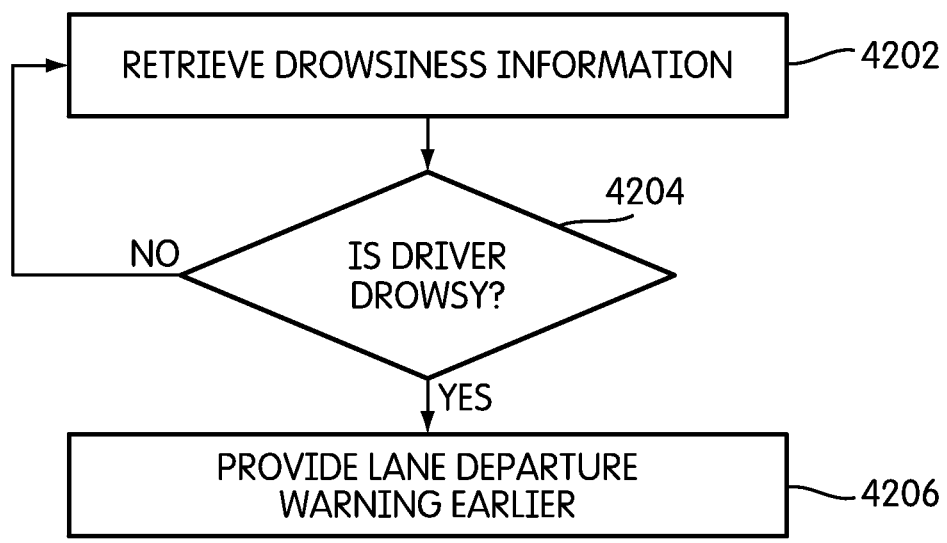
FIG. 59 is an embodiment of a process of modifying the control of a lane departure warning system according to driver behavior.

FIG. 59 illustrates an embodiment of a process of operating a lane departure warning system in response to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 4202, response system 199 may retrieve drowsiness information. In step 4204, response system 199 may determine if the driver is drowsy. If the driver is not drowsy, response system 199 proceeds back to step 4202. Otherwise, response system 199 proceeds to step 4206. In step 4206, response system 199 may modify the operation of lane departure warning system 240 so that the driver is warned earlier about potential lane departures.

Figure 60:
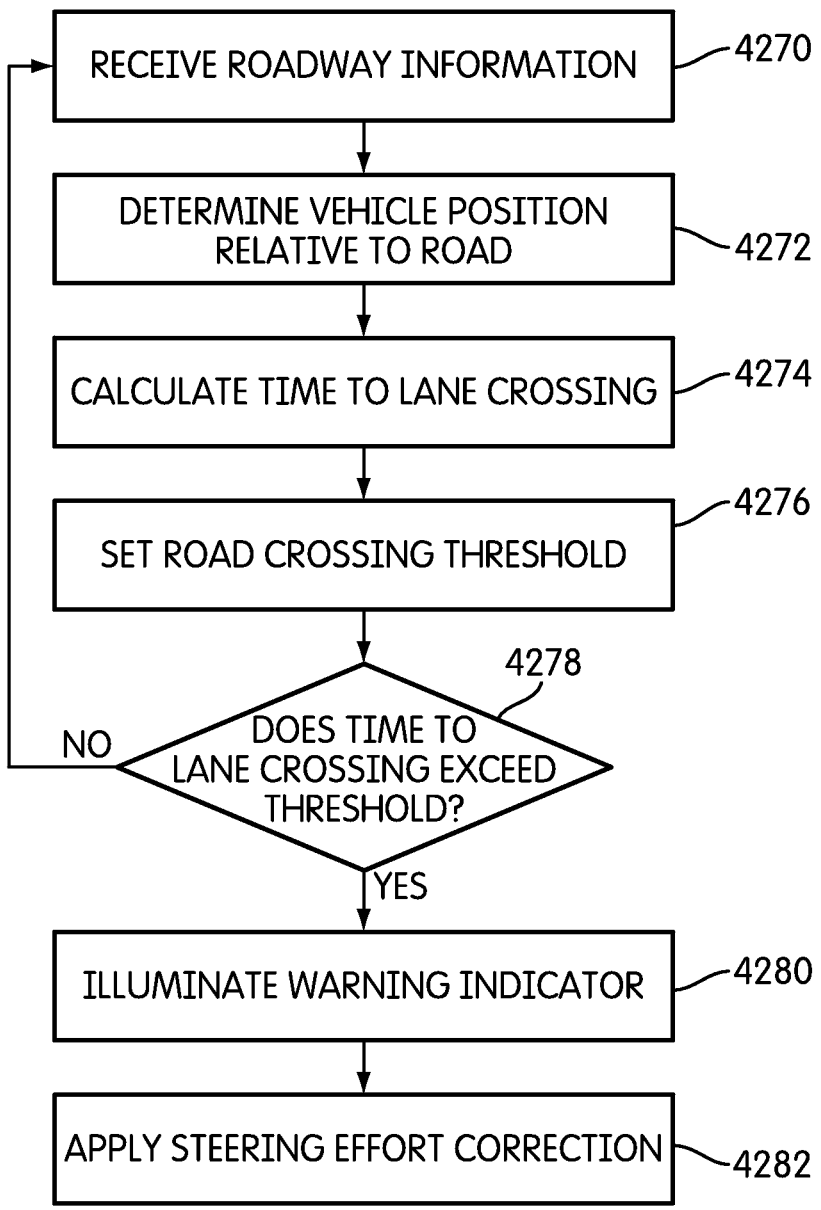
FIG. 60 is an embodiment of a process of modifying the operation of a lane departure warning system in response to driver behavior.

FIG. 60 illustrates an embodiment of a process for operating a lane departure warning system in response to driver behavior. In particular, FIG. 60 illustrates an embodiment of a process where the operation of a lane departure warning system is modified in response to the body state index of a driver. In step 4270, response system 199 receives roadway information. The roadway information can include road size, shape as well as the locations of any road markings or lines. In step 4272, response system 199 may determine the vehicle position relative to the road. In step 4274, response system 199 may calculate the time to lane crossing. This can be determined from vehicle position, vehicle turning information and lane location information.

In step 4276, response system 199 may set the road crossing threshold. The road crossing threshold may be a time associated with the time to lane crossing. In step 4278, response system 199 determines if the time to lane crossing exceeds the road crossing threshold. If not, response system 199 proceeds back to step 4270. Otherwise, response system 199 proceeds to step 4280 where a warning indicator is illuminated indicating that the vehicle is crossing a lane. In other cases, audible or haptic warnings could also be provided. If the vehicle continues exiting the lane a steering effort correction may be applied in step 4282.

Figure 61:
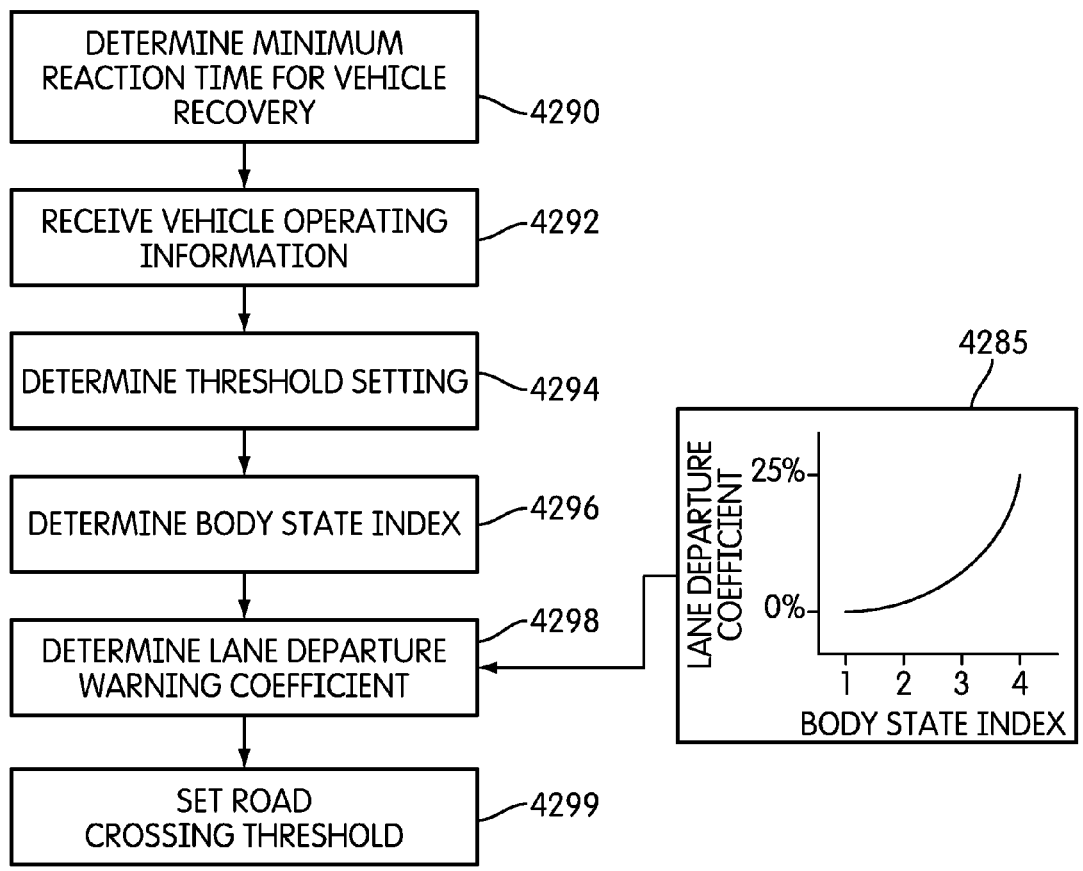
FIG. 61 is an embodiment of a process for setting a road crossing threshold.

FIG. 61 illustrates an embodiment of a process for setting the road crossing threshold. In step 4290, response system 199 determines a minimum reaction time for vehicle recovery. In some cases, the minimum reaction time is associated with the minimum amount of time for a vehicle to avoid a lane crossing once a driver becomes aware of the potential lane crossing. In step 4292, response system 199 may receive vehicle operating information. Vehicle operating information could include roadway information as well as information related to the location of the vehicle within the roadway.

In step 4294, response system 199 determines an initial threshold setting from the minimum reaction time and the vehicle operating information. In step 4296, response system 199 determines the body index state of the driver. In step 4298, response system 199 determines a lane departure warning coefficient according to the body state index. An exemplary look-up table 4285 includes a range of coefficient values between 0% and 25% as a function of the body state index. Finally, in step 4299, response system 199 may set the road crossing threshold according to the lane departure warning coefficient and the initial threshold setting.

In addition to providing earlier warnings to a driver through a lane departure warning system, response system 199 can also modify the operation of a lane keep assist system, which may also provide warnings as well as driving assistance in order to maintain a vehicle in a predetermined lane.

Figure 62:
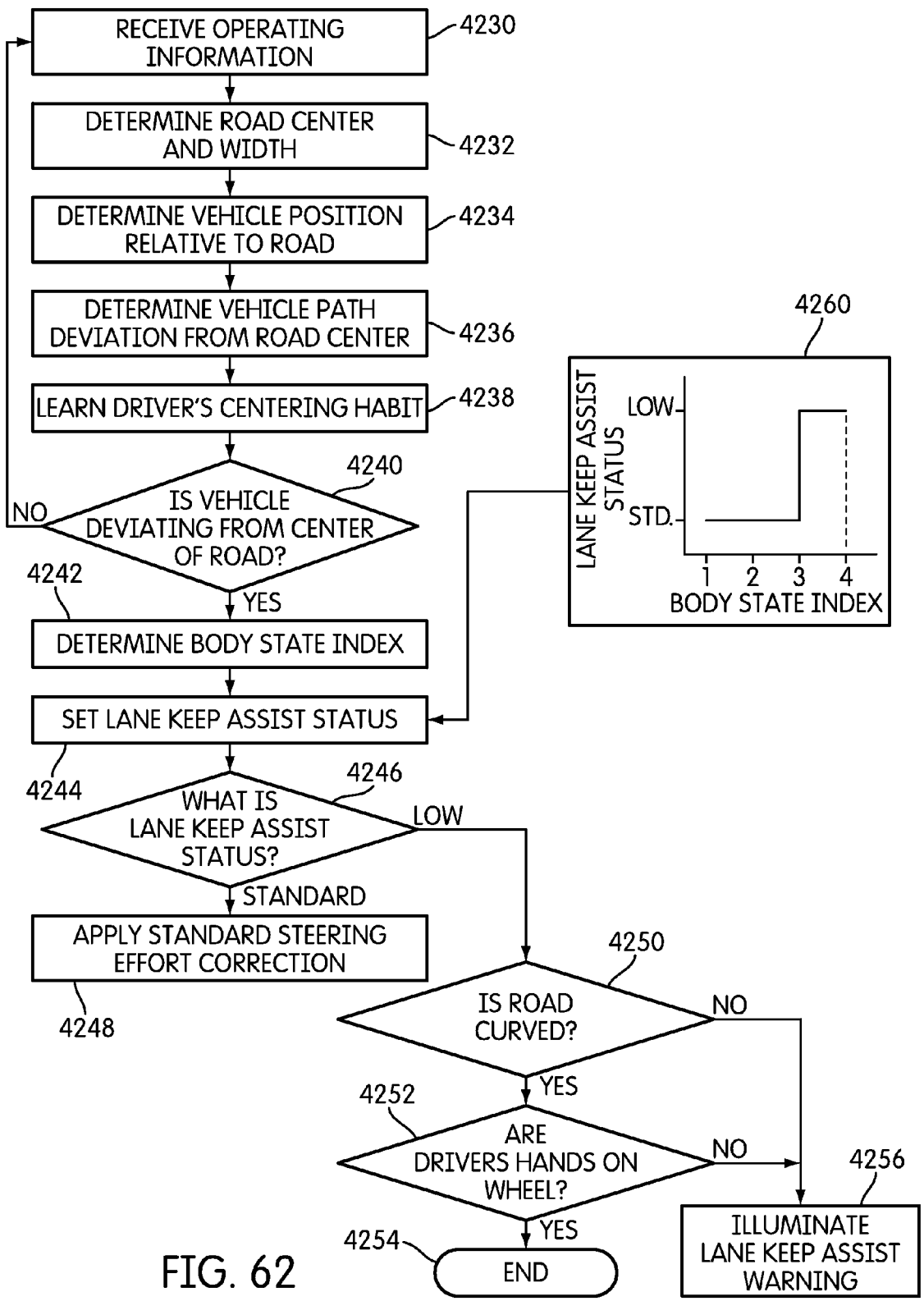
FIG. 62 is an embodiment of a process of modifying the operation of a lane keep assist system in response to driver behavior.

FIG. 62 illustrates an embodiment of a process of operating a lane keep assist system in response to driver behavior. In particular, FIG. 62 illustrates a method where the operation of a lane keep assist system is modified in response to the body state index of a driver. In step 4230, response system 199 may receive operating information. For example, in some cases response system 199 may receive roadway information related to the size and/or shape of a roadway, as well as the location of various lines on the roadway. In step 4232, response system 199 determines the location of the road center and the width of the road. This can be determined using sensed information, such as optical information of the roadway, stored information including map based information, or a combination of sensed and stored information. In step 4234, response system 199 may determine the vehicle position relative to the road.

In step 4236, response system 199 may determine the deviation of the vehicle path from the road center. In step 4238, response system 199 may learn the driver's centering habits. For example, alert drivers generally adjust the steering wheel constantly in attempt to maintain the car in the center of a lane. In some cases, the centering habits of a driver can be detected by response system 199 and learned. Any machine learning method or pattern recognition algorithm could be used to determine the driver's centering habits.

In step 4240, response system 199 may determine if the vehicle is deviating from the center of the road. If not, response system 199 proceeds back to step 4230. If the vehicle is deviating, response system 199 proceeds to step 4242. In step 4242, response system 199 may determine the body state index of the driver. Next, in step 4244, response system 199 may set the lane keep assist status using the body state index. For example, look-up table 4260 is an example of a relationship between body state index and lane keep assist status. In particular, the lane keep assist status is set to a standard state for low body state index (indexes 1 or 2) and is set to a low state for a higher body state index (indexes 3 or 4). In other embodiments, any other relationship between body state index and lane keep assist status can be used.

In step 4246, response system 199 may check the lane keep assist status. If the lane keep assist status is standard, response system 199 proceeds to step 4248 where standard steering effort corrections are applied to help maintain the vehicle in the lane. If, however, response system 199 determines that the lane keep assist status is low in step 4246, response system 199 may proceed to step 4250. In step 4250, response system 199 determines if the road is curved. If not, response system 199 proceeds to step 4256 to illuminate a lane keep assist warning so the driver knows the vehicle is deviating from the lane. If, in step 4250, response system 199 determines the road is curved, response system 199 proceeds to step 4252. In step 4252, response system 199 determines if the driver's hands are on the steering wheel. If so, response system 199 proceeds to step 4254 where the process ends. Otherwise, response system 199 proceeds to step 4256.

This arrangement allows response system 199 to modify the operation of the lane keep assist system in response to driver behavior. In particular, the lane keep assist system may only help steer the vehicle automatically when the driver state is alert (low body state index). Otherwise, if the driver is drowsy or very drowsy (higher body state index), response system 199 may control the lane keep assist system to only provide warnings of lane deviation without providing steering assistance. This may help increase the alertness of the driver when he or she is drowsy.

A response system can include provisions for modifying the control of a blind spot indicator system when a driver is drowsy. For example, in some cases, a response system could increase the detection area. In other cases, the response system could control the monitoring system to deliver warnings earlier (i.e., when an approaching vehicle is further away).

Figure 63:
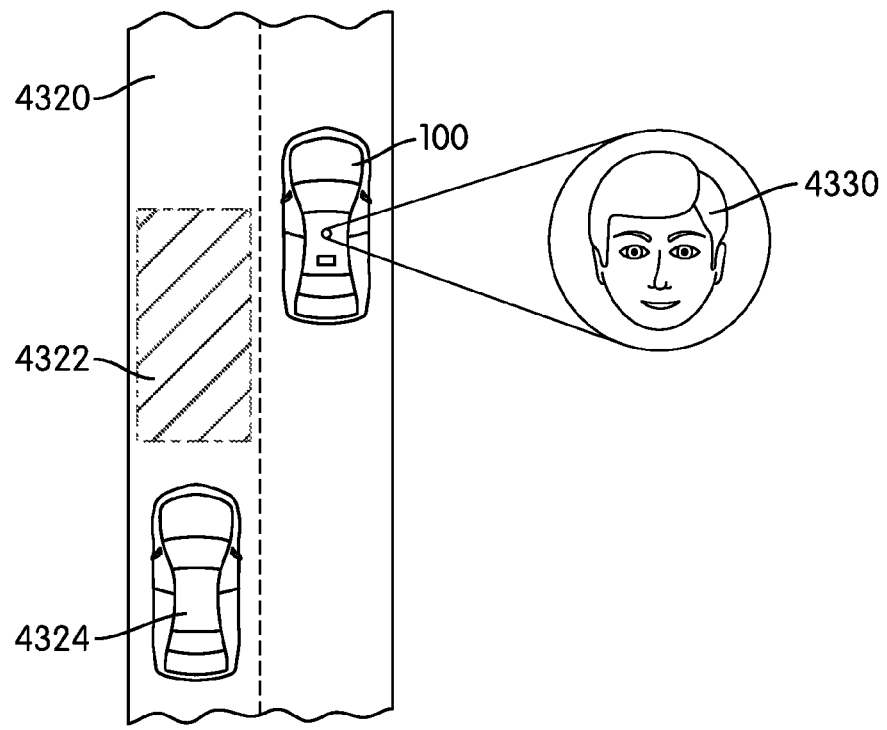
FIG. 63 is a schematic view of an embodiment in which a blind spot indicator system is active.
Figure 64:
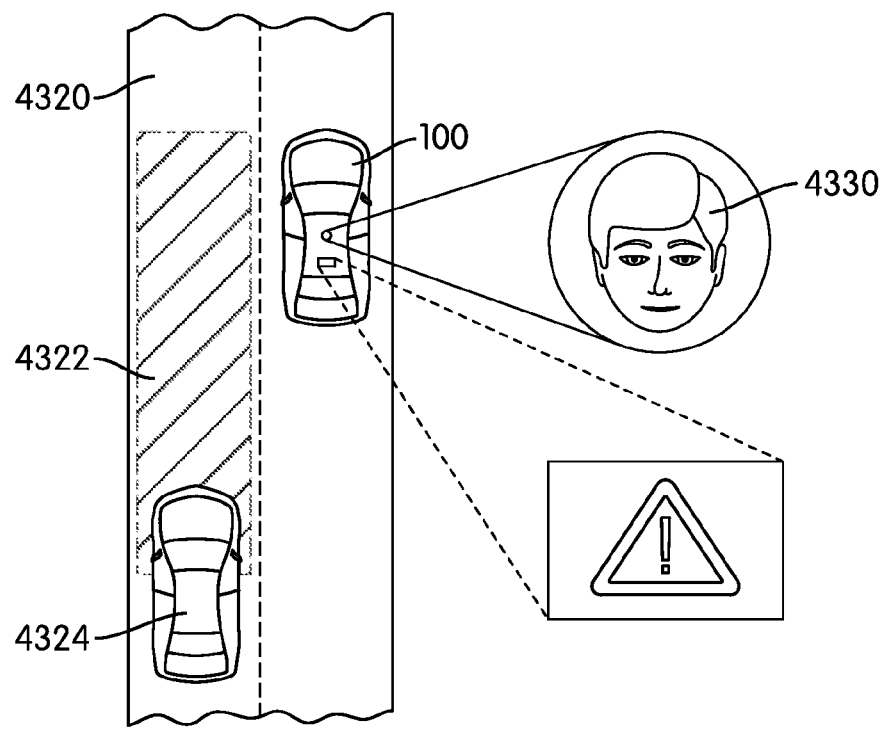
FIG. 64 is a schematic view of an embodiment in which a blind spot indicator system is active and a blind spot monitoring zone is increased in response to driver behavior.

FIGS. 63 and 64 illustrate schematic views of an embodiment of the operation of a blind spot indicator system. In this embodiment, motor vehicle 100 is traveling on roadway 4320. Blind spot indicator system 242 (see FIG. 2) may be used to monitor any objects traveling within blind spot monitoring zone 4322. For example, in the current embodiment, blind spot indicator system 242 may determine that no object is inside of blind spot monitoring zone 4322. In particular, target vehicle 4324 is just outside of blind spot monitoring zone 4322. In this case, no alert is sent to the driver.

In FIG. 63, driver 4330 is shown as fully alert. In this alert state, the blind spot monitoring zone is set according to predetermined settings and/or vehicle operating information. However, as seen in FIG. 64, as driver 4330 becomes drowsy, response system 199 may modify the operation of blind spot indicator system 242. For example, in one embodiment, response system 199 may increase the size of blind spot monitoring zone 4322. As seen in FIG. 64, under these modified conditions target vehicle 4324 is now traveling inside of blind spot monitoring zone 4322. Therefore, in this situation driver 4330 is alerted to the presence of target vehicle 4324.

Figure 65:
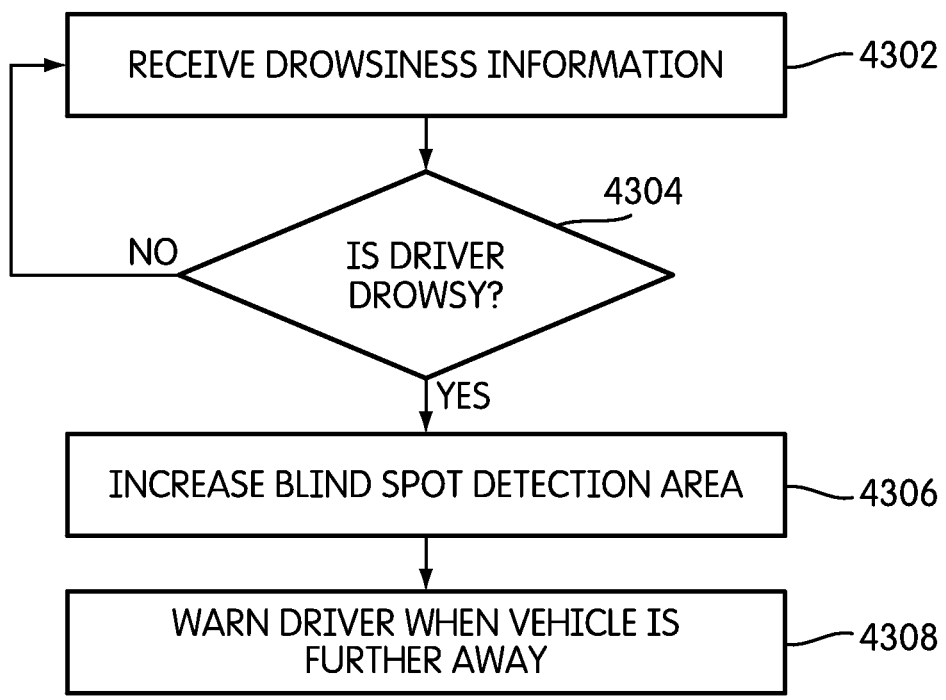
FIG. 65 is an embodiment of a process of modifying the control of a blind spot indicator system.

FIG. 65 illustrates an embodiment of a process of operating a blind spot indicator system in response to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 4302, response system 199 may receive drowsiness information. In step 4304, response system 199 determines if the driver is drowsy. If the driver is not drowsy, response system 199 returns back to step 4302. If the driver is drowsy, response system 199 proceeds to step 4306. In step 4306, response system 4306 may increase the blind spot detection area. For example, if the initial blind spot detection area is associated with the region of the vehicle between the passenger side mirror about 3-5 meters behind the rear bumper, the modified blind spot detection area may be associated with the region of the vehicle between the passenger side mirror and about 4-7 meters behind the rear bumper. Following this, in step 4308, response system 199 may modify the operation of blind spot indicator system 242 so that the system warns a driver when a vehicle is further away. In other words, if the system initially warns a driver if the approaching vehicle is within 5 meters of motor vehicle 100, or the blind spot, the system may be modified to warn the driver when the approaching vehicle is within 10 meters of motor vehicle 100, or the blind spot of motor vehicle 100. Of course, it will be understood that in some cases, step 4306 or step 4308 may be optional steps. In addition, other sizes and locations of the blind spot zone are possible.

Figure 66:
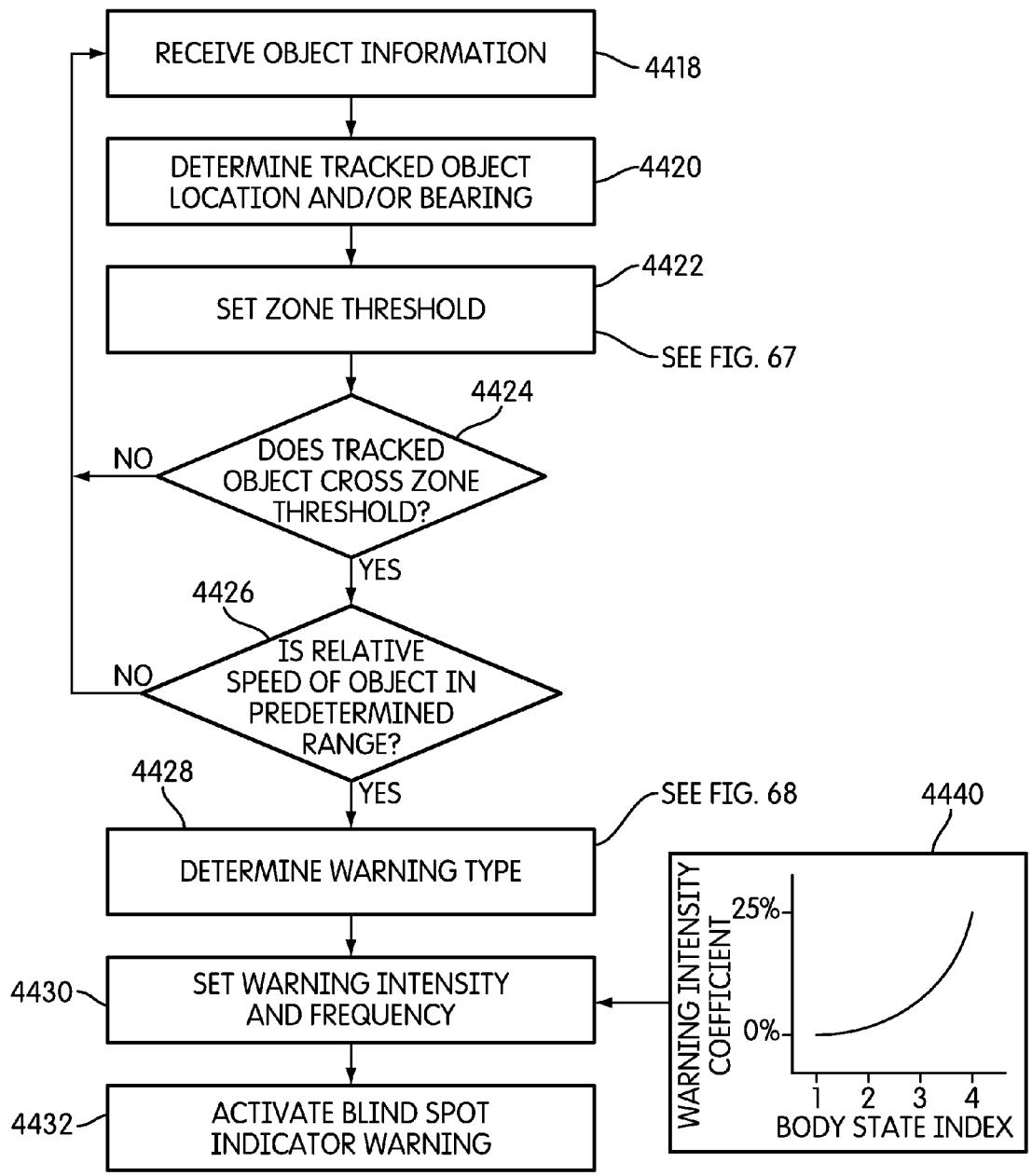
FIG. 66 is an embodiment of a process for controlling a blind spot indicator system is response to driver behavior.

FIG. 66 illustrates an embodiment of a process of operating a blind spot indicator system in response to driver behavior as a function of the body state index of the driver. In step 4418, response system 199 receives object information. This information can include information from one or more sensors capable of detecting the location of various objects (including other vehicles) within the vicinity of the vehicle. In some cases, for example, response system 199 receives information from a remote sensing device (such as a camera, lidar or radar) for detecting the presence of one or more objects.

In step 4420, response system 199 may determine the location and/or bearing of a tracked object. In step 4422, response system 199 sets a zone threshold. The zone threshold may be a location threshold for determining when an object has entered into a blind spot monitoring zone. In some cases, the zone threshold may be determined using the body state index of the driver as well as information about the tracked object.

In step 4424, response system 199 determines if the tracked object crosses the zone threshold. If not, response system 199 proceeds to step 4418. Otherwise, response system 199 proceeds to step 4426. In step 4426, response system 199 determines if the relative speed of the object is in a predetermined range. If the relative speed of the object is in the predetermined range, it is likely to stay in the blind spot monitoring zone for a long time and may pose a very high threat. Response system 199 may ignore objects with a relative speed outside the predetermined range, since the object is not likely to stay in the blind spot monitoring zone for very long. If the relative speed is not in the predetermined range, response system 199 proceeds back to step 4418. Otherwise, response system 199 proceeds to step 4428.

In step 4428, response system 199 determines a warning type using the body state index. In step 4430, response system 199 sets the warning intensity and frequency using the body state index. Lookup table 4440 is an example of a relationship between body state index and a coefficient for warning intensity. Finally, in step 4432, response system 199 activates the blind spot indicator warning to alert the driver of the presence of the object in the blind spot.

Figures 67, 68:
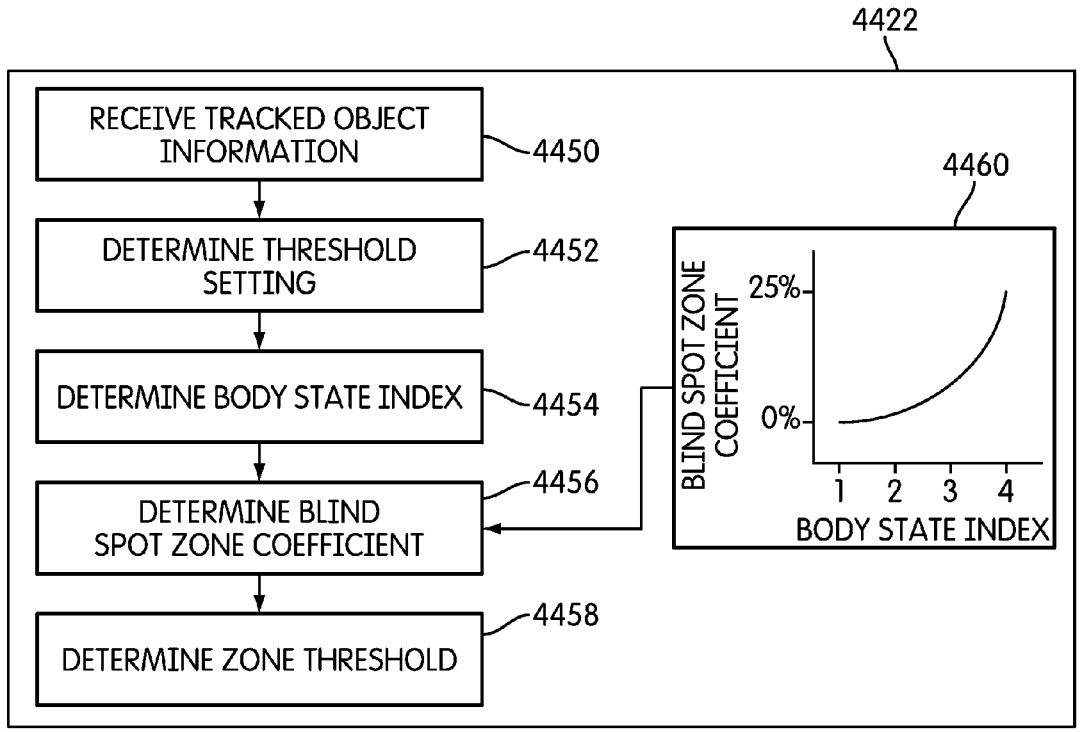
FIG. 67 is an embodiment of a process for determining a zone threshold for a blind spot indicator system.
FIG. 68 is an embodiment of a chart for selecting warning type according to body state index.

FIG. 67 illustrates an embodiment of a process for determining a zone threshold. In step 4450, response system 199 retrieves tracked object information. In step 4452, response system 199 may determine an initial threshold setting. In step 4454, response system 199 may determine the body state index of the driver. In step 4456, response system 199 may determine a blind spot zone coefficient. For example, look-up table 4460 includes a predetermined relationship between body state index and the blind spot zone coefficient. The blind spot zone coefficient may range between 0% and 25% in some cases and may generally increase with the body state index. Finally, in step 4458, response system 199 may determine the zone threshold.

Generally, the zone threshold can be determined using the initial threshold setting (determined in step 4452) and the blind spot zone coefficient. For example, if the blind spot zone coefficient has a value of 25%, the zone threshold may be up to 25% larger than the initial threshold setting. In other cases, the zone threshold may be up to 25% smaller than the initial threshold setting. In other words, the zone threshold may be increased or decreased from the initial threshold setting in proportion to the value of the blind spot zone coefficient. Moreover, as the value of the zone threshold changes, the size of the blind spot zone or blind spot detection area may change. For example, in some cases, as the value of the zone threshold increases, the length of the blind spot detection area is increased, resulting in a larger detection area and higher system sensitivity. Likewise, in some cases, as the value of the zone threshold decreases, the length of the blind spot detection area is decreased, resulting in a smaller detection area and lower system sensitivity.

FIG. 68 illustrates an example of an embodiment of various warning settings according to the body state index in the form of lookup table 4470. For example, when the driver's body state index is 1, the warning type may be set to indicator only. In other words, when the driver is not drowsy, the warning type may be set to light-up one or more warning indicators only. When the body state index is 2, both indicators and sounds may be used. When the driver's body state index is 3, indicators and haptic feedback may be used. For example, a dashboard light may flash and the driver's seat or the steering wheel may vibrate. When the driver's body state index is 4, indicators, sounds and haptic feedback may all be used. In other words, as the driver becomes more drowsy (increased body state index), a greater variety of warning types may be used simultaneously. It will be understood that the present embodiment only illustrates exemplary warning types for different body state indexes and in other embodiments any other configuration of warning types for body state indexes can be used.

FIGS. 69 through 72 illustrate exemplary embodiments of the operation of a collision mitigation braking system (CMBS) in response to driver behavior. In some cases, a collision mitigation braking system could be used in combination with a forward collision warning system. In particular, in some cases, a collision mitigation braking system could generate forward collision warnings in combination with, or instead of, a forward collision warning system. Moreover, the collision mitigation braking system could be configured to further actuate various systems, including braking systems and electronic seatbelt pretensioning systems, in order to help avoid a collision. In other cases, however, a collision mitigation braking system and a forward collision warning system could be operated as independent systems. In the exemplary situations discussed below, a collision mitigation braking system is capable of warning a driver of a potential forward collision. However, in other cases, a forward collision warning could be provided by a separate forward collision warning system.

Figure 69:
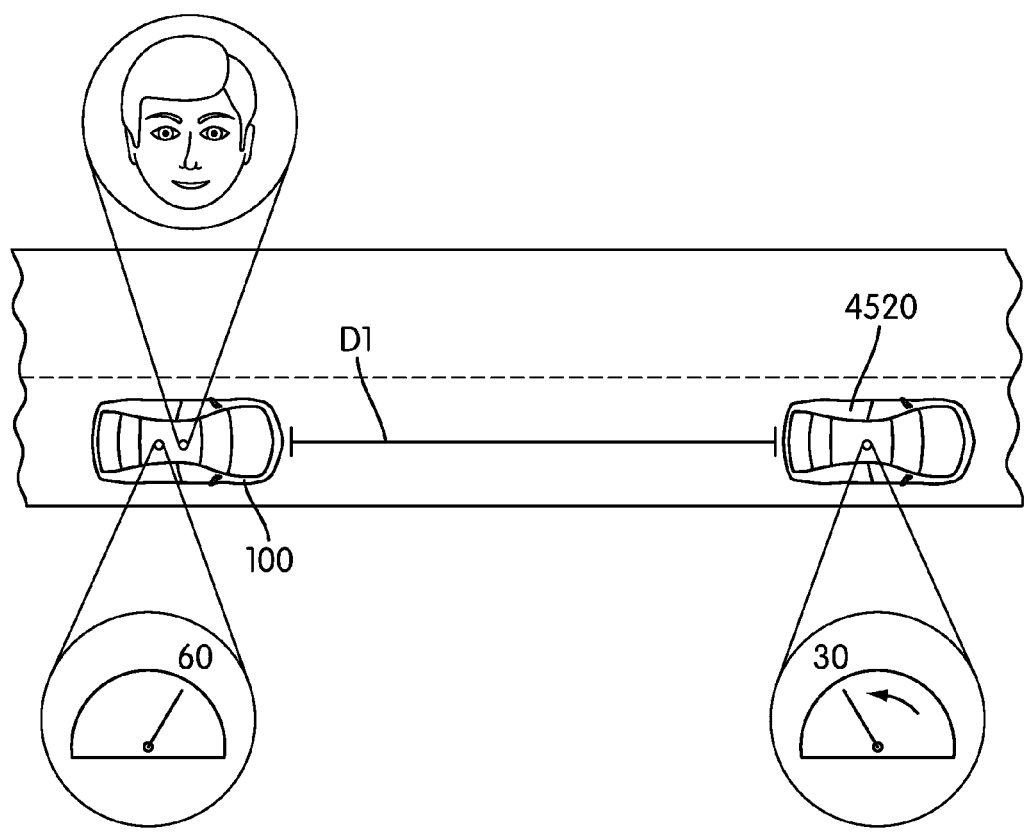
FIG. 69 is a schematic view of an embodiment of a collision mitigation braking system in which no warning is provided when the driver is alert.
Figure 70:
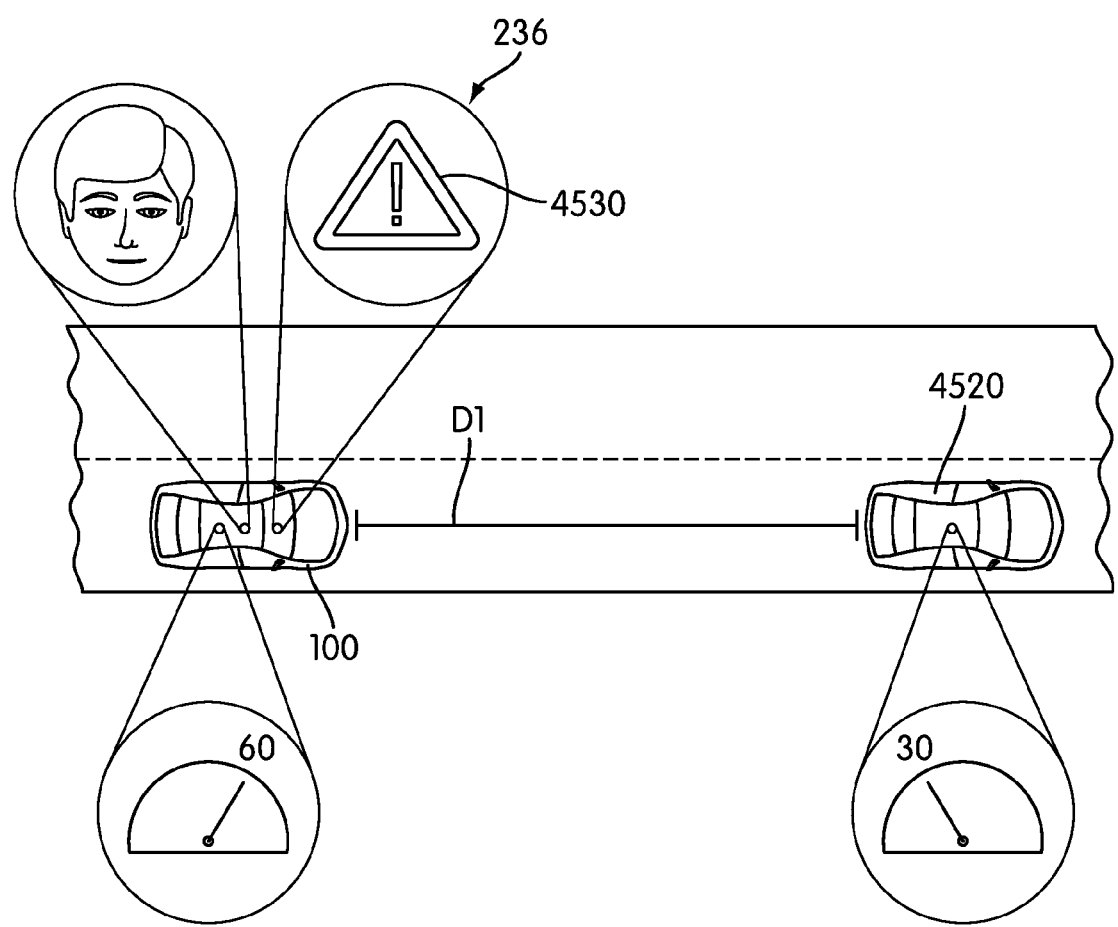
FIG. 70 is a schematic view of an embodiment of a collision mitigation braking system in which a warning is provided when the driver is drowsy.

As seen in FIG. 69, motor vehicle 100 is driving behind target vehicle 4520. In this situation, motor vehicle 100 is traveling at approximately 60 mph, while target vehicle 4520 is slowing to approximately 30 mph. At this point, motor vehicle 100 and target vehicle 4520 are separated by distance D1. Because the driver is alert, however, CMBS 236 determines that distance D1 is not small enough to require a forward collision warning. In contrast, when the driver is drowsy, as seen in FIG. 70, response system 199 may modify the operation of the CMBS 236 so that a warning 4530 is generated during a first warning stage of CMBS 236. In other words, CMBS 236 becomes more sensitive when the driver is drowsy. Moreover, as discussed below, the level of sensitivity may vary in proportion to the degree of drowsiness (indicated by the body state index).

Figure 71:
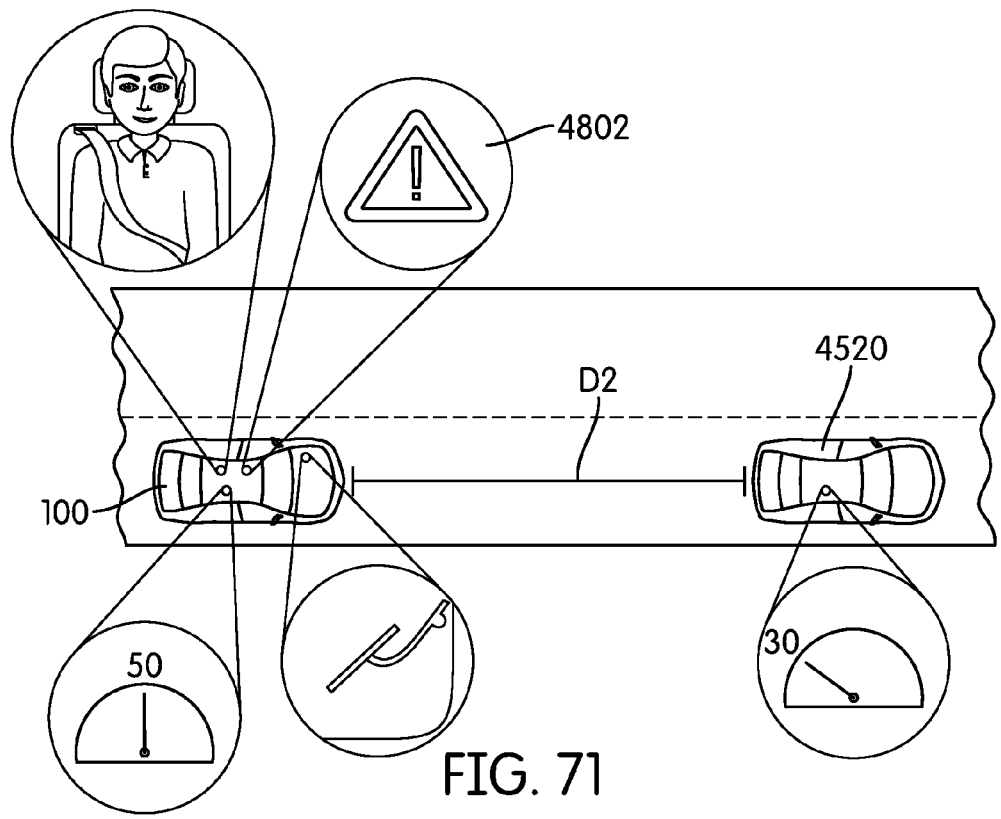
FIG. 71 is a schematic view of an embodiment of a collision mitigation braking system in which no automatic seatbelt pretensioning is provided when the driver is alert.
Figure 72:
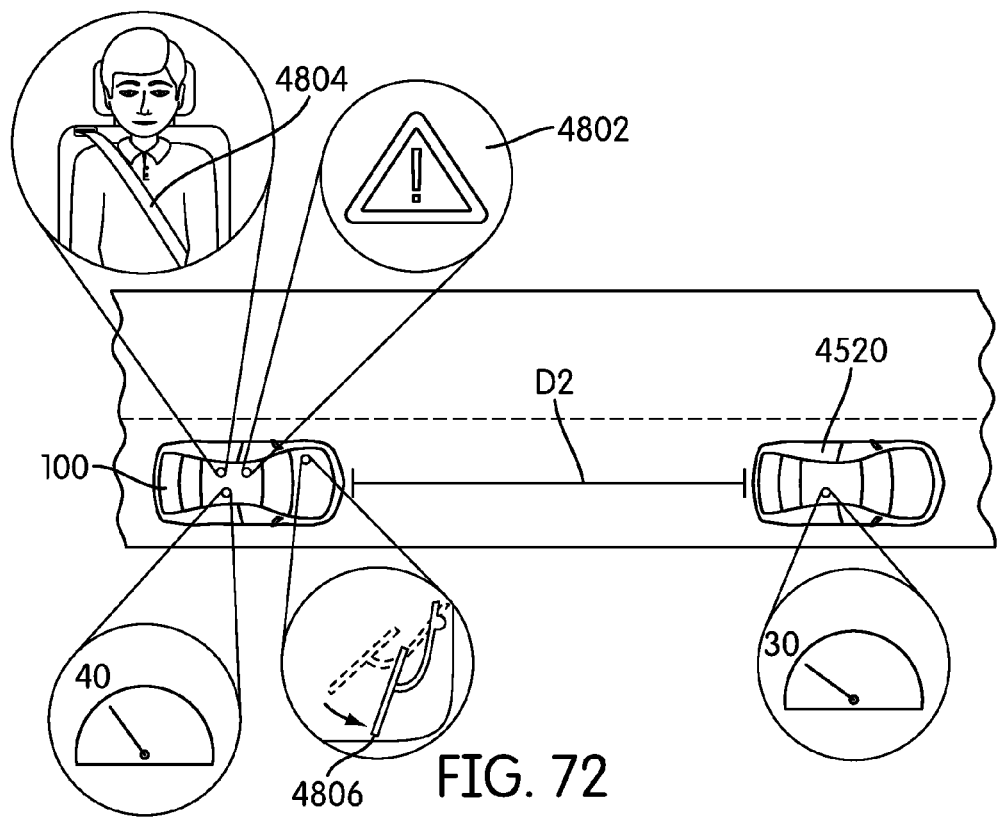
FIG. 72 is a schematic view of an embodiment of a collision mitigation braking system in which automatic seatbelt pretensioning is provided when the driver is drowsy.

Referring now to FIG. 71, motor vehicle 100 continues to approach target vehicle 4520. At this point, motor vehicle 100 and target vehicle 4520 are separated by distance D2. This distance is below the threshold for activating a forward collision warning 4802. In some cases, the warning could be provided as a visual alert and/or an audible alert. However, because the driver is alert, distance D2 is not determined to be small enough to activate additional collision mitigation provisions, such as automatic braking and/or automatic seatbelt pretensioning. In contrast, when the driver is drowsy, as seen in FIG. 72, response system 199 may modify the operation of CMBS 236 so that in addition to providing forward collision warning 4802, CMBS 236 may also automatically pretension seatbelt 4804. Also, in some cases, CMBS 236 may apply light braking 4806 to slow motor vehicle 100. In other cases, however, no braking may be applied at this point.

For purposes of illustration, the distance between vehicles is used as the threshold for determining if response system 199 should issue a warning and/or apply other types of intervention. However, it will be understood that in some cases, the time to collision between vehicles may be used as the threshold for determining what actions response system 199 may perform. In some cases, for example, using information about the velocities of the host and target vehicles as well as the relative distance between the vehicles can be used to estimate a time to collision. Response system 199 may determine if warnings and/or other operations should be performed according to the estimated time to collision.

Figure 73:
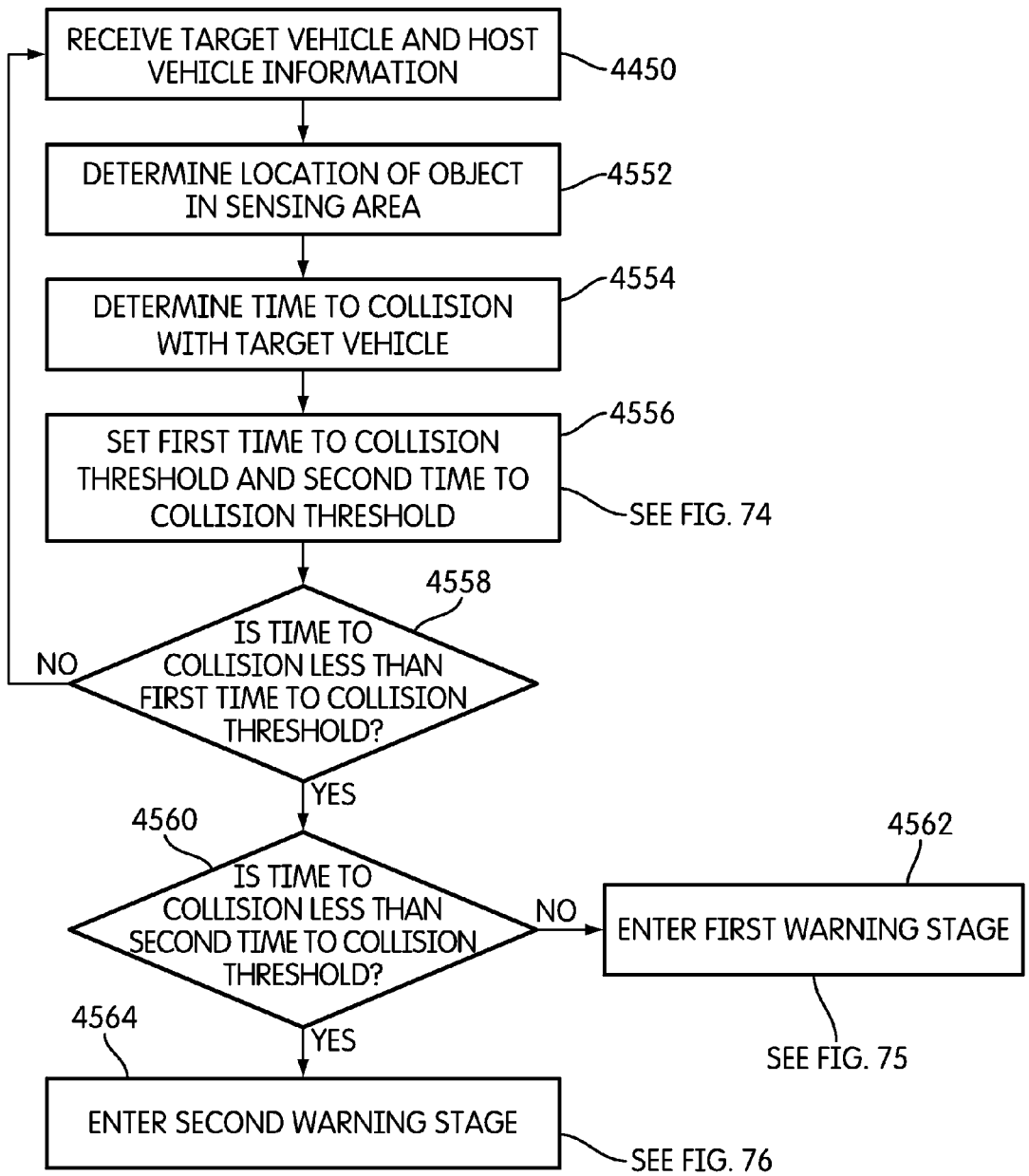
FIG. 73 is an embodiment of a process for controlling a collision mitigation braking system in response to driver behavior.

FIG. 73 illustrates an embodiment of a process for operating a collision mitigation braking system in response to driver behavior. In step 4550, response system 199 may receive target vehicle information and host vehicle information. For example, in some cases response system 199 may receive the speed, location and/or bearing of the target vehicle as well as the host vehicle. In step 4552, response system 199 may determine the location of an object in the sensing area, such as a target vehicle. In step 4554, response system 199 may determine the time to collision with the target vehicle.

In step 4556, response system 199 may set a first time to collision threshold and a second time to collision threshold. In some cases, the first time to collision threshold may be greater than the second time to collision threshold. However, in other cases, the first time to collision threshold may be less than or equal to the second time to collision threshold. Details for determining the first time to collision threshold and the second time to collision threshold are discussed below and shown in FIG. 74.

In step 4558, response system 199 may determine if the time to collision is less than the first time to collision threshold. If not, response system 199 returns to step 4550. In some cases, the first time to collision threshold may a value above which there is no immediate threat of a collision. If the time to collision is less than the first time to collision threshold, response system 199 proceeds to step 4560.

At step 4560, response system 199 may determine if the time to collision is less than the second time to collision threshold. If not, response system 199 enters a first warning stage at step 4562. The response system 199 may then proceed through further steps discussed below and shown in FIG. 75. If the time to collision is greater than the second time to collision threshold, response system 199 may enter a second warning stage at step 4564. Response system 199 may then proceed through further steps discussed below and shown in FIG. 76.

Figure 74:
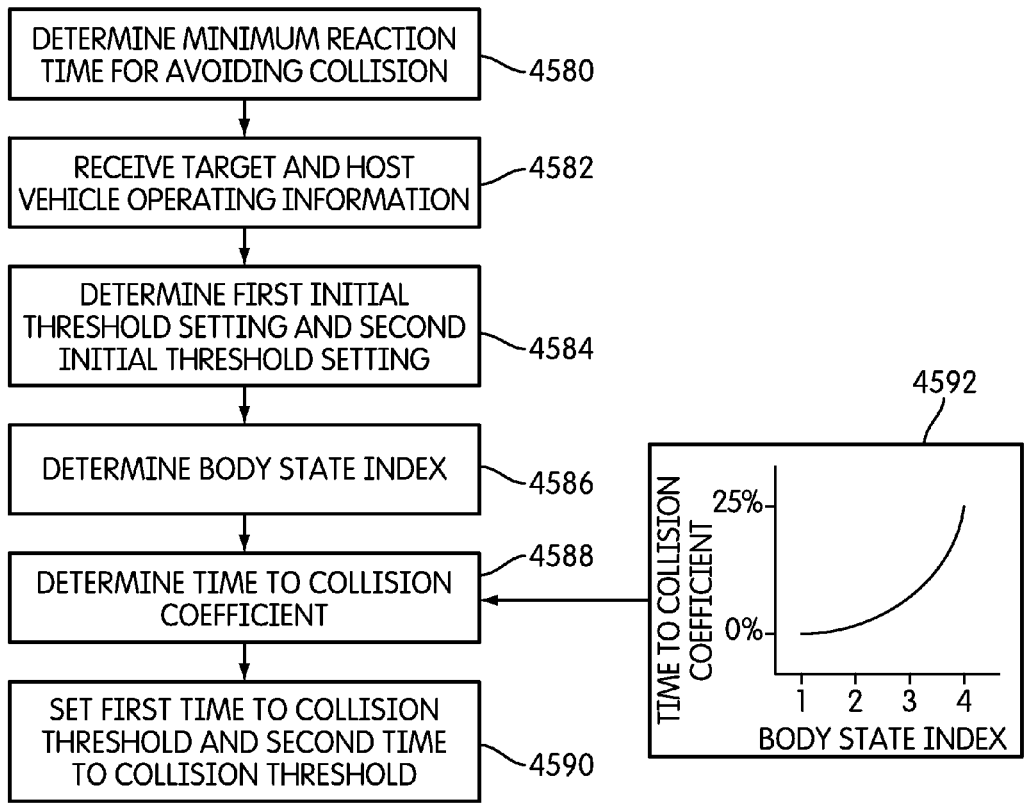
FIG. 74 is an embodiment of a process for setting time to collision thresholds.

FIG. 74 illustrates an embodiment of a process for setting a first time to collision threshold and a second time to collision threshold. In step 4580, response system 199 may determine a minimum reaction time for avoiding a collision. In step 4582, response system 199 may receive target and host vehicle information such as location, relative speeds, absolute speeds as well as any other information. In step 4584, response system 199 may determine a first initial threshold setting and a second initial threshold setting. In some cases, the first initial threshold setting corresponds to the threshold setting for warning a driver. In some cases, the second initial threshold setting corresponds to the threshold setting for warning a driver and also operating braking and/or seatbelt pretensioning. In some cases, these initial threshold settings may function as default setting that may be used with a driver is fully alert. Next, in step 4586, response system 199 may determine the body state index of the driver.

In step 4588, response system 199 may determine a time to collision coefficient. In some cases, the time to collision coefficient can be determined using look-up table 4592, which relates the time to collision coefficient to the body state index of the driver. In some cases, the time to collision coefficient increases from 0% to 25% as the body state index increases. In step 4590, response system 199 may set the first time to collision threshold and the second time to collision threshold. Although a single time to collision coefficient is used in this embodiment, the first time to collision threshold and the second time to collision threshold may differ according to the first initial threshold setting and the second initial threshold setting, respectively. Using this configuration, in some cases, the first time to collision threshold and the second time to collision threshold may be decreased as the body state index of a driver increases. This allows response system 199 to provide earlier warnings of potential hazards when a driver is drowsy. Moreover, the timing of the warnings varies in proportion to the body state index.

Figure 75:
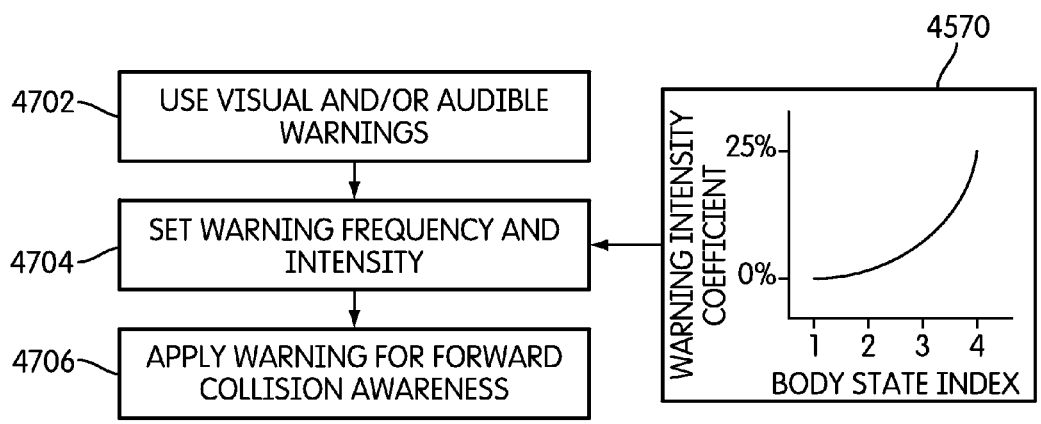
FIG. 75 is an embodiment of a process for operating a collision mitigation braking system during a first warning stage.

FIG. 75 illustrates an embodiment of a process for operating a motor vehicle in a first warning stage of CMBS 236. In step 4702, response system 199 may select visual and/or audible warnings for alerting a driver of a potential forward collision. In some cases, a warning light may be used. In other cases, an audible noise, such as a beep, could be used. In still other cases, both a warning light and a beep could be used.

In step 4704, response system 199 may set the warning frequency and intensity. This may be determined using the body state index in some cases. In particular, as the driver state increases due to the increased drowsiness of the driver, the warning state frequency and intensity can be increased. For example, in some cases look-up table 4570 can be used to determine the warning frequency and intensity. In particular, in some cases as the warning intensity coefficient increases (as a function of body state index), the intensity of any warning can be increased by up to 25%. In step 4706, response system 199 may apply a warning for forward collision awareness. In some cases, the intensity of the warning can be increased for situations where the warning intensity coefficient is large. For example, for a low warning intensity coefficient (0%) the warning intensity may be set to a predetermined level. For higher warning intensity coefficients (greater than 0%) the warning intensity may be increased beyond the predetermined level. In some cases, the luminosity of visual indicators can be increased. In other cases, the volume of audible warnings can be increased. In still other cases, the pattern of illuminating a visual indicator or making an audible warning could be varied.

Figure 76:
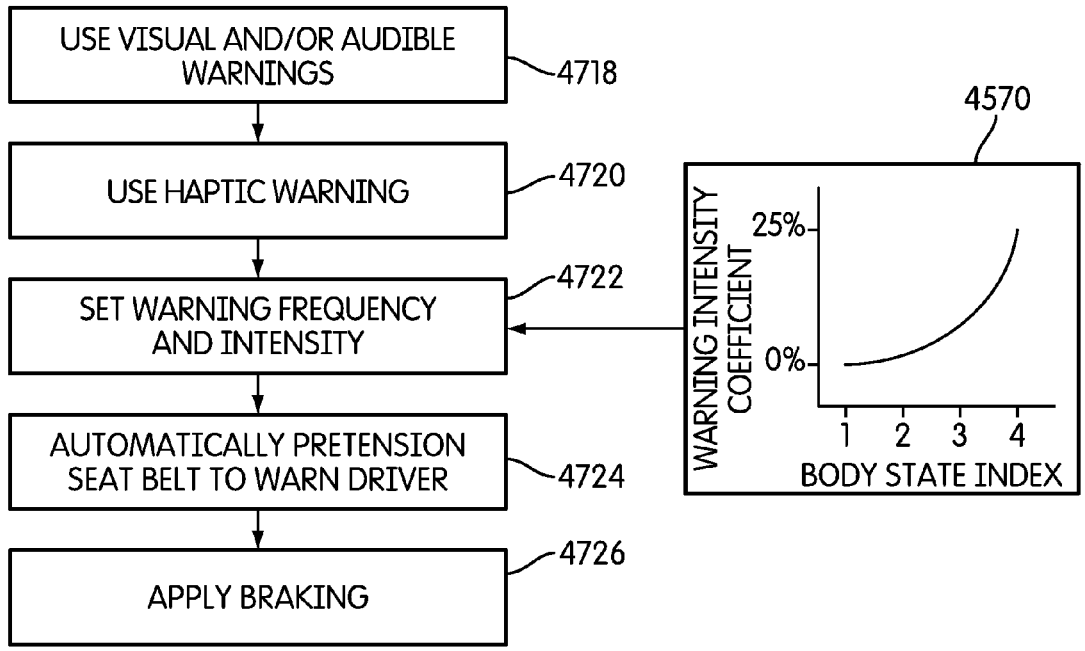
FIG. 76 is an embodiment of a process for operating a collision mitigation braking system during a second warning stage.

FIG. 76 illustrates an embodiment of process of operating a motor vehicle in a second stage of CMBS 236. In some cases, during step 4718, CMBS 236 may use visual and/or audible warnings to alert a driver of a potential collision. In some cases, the level and/or intensity of the warnings could be set according to the driver state index, as discussed above and shown in step 4704 of FIG. 75. Next, in step 4720, response system 199 may use a haptic warning. In situations where visual and/or audible warnings are also used, the haptic warning can be provided simultaneously with the visual and/or audible warnings. In step 4722, response system 199 may set the warning frequency and intensity of the haptic warning. This may be achieved using look-up table 4570, for example. Next, in step 4724, response system 199 may automatically pretension a seatbelt in order to warn the driver. The frequency and intensity of the tensioning may vary as determined in step 4722. In step 4726, response system 199 may apply light braking automatically in order to slow the vehicle. In some cases, step 4726 may be optional step.

Figure 77:
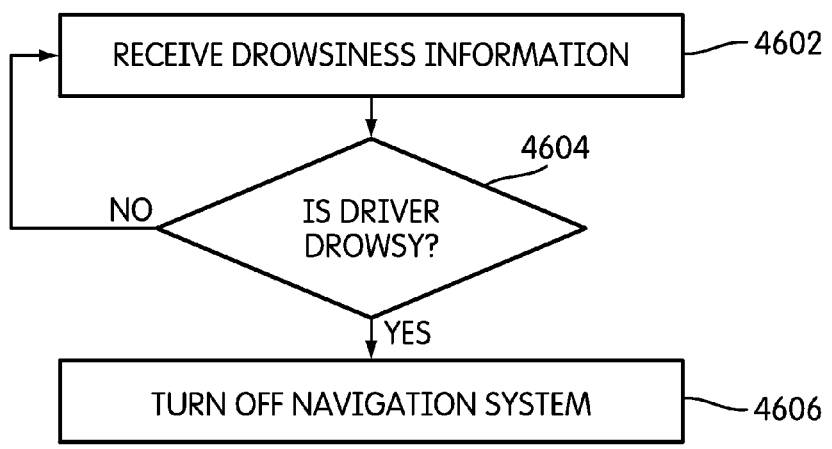
FIG. 77 is an embodiment of a process for operating a navigation system according to driver monitoring.

FIG. 77 illustrates an embodiment of a process of operating a navigation system in response to driver behavior. In some embodiments, some of the following steps could be accomplished by a response system 199 of a motor vehicle. In some cases, some of the following steps may be accomplished by an ECU 150 of a motor vehicle. In other embodiments, some of the following steps could be accomplished by other components of a motor vehicle, such as vehicle systems 172. In still other embodiments, some of the following steps could be accomplished by any combination of systems or components of the vehicle. It will be understood that in some embodiments one or more of the following steps may be optional. For purposes of reference, the following method discusses components shown in FIGS. 1 through 3, including response system 199.

In step 4602, response system 199 may receive drowsiness information. In step 4604, response system 199 may determine if the driver is drowsy. If the driver is not drowsy, response system 199 proceeds back to step 4602. Otherwise, response system 199 proceeds to step 4606. In step 4606, response system 199 may turn off navigation system 4606. This may help reduce driver distraction.

It will be understood that in some embodiments, multiple vehicle systems could be modified according to driver behavior substantially simultaneously. For example, in some cases when a driver is drowsy, a response system could modify the operation of a collision warning system and a lane keep assist system to alert a driver earlier of any potential collision threats or unintentional lane departures. Likewise, in some cases when a driver is drowsy, a response system could automatically modify the operation of an antilock brake system and a brake assist system to increase braking response. The number of vehicle systems that can be simultaneously activated in response to driver behavior is not limited.

It will be understood that the current embodiment illustrates and discusses provisions for sensing driver behavior and modifying the operation of one or more vehicle systems accordingly. However, these methods are not limited to use with a driver. In other embodiments, these same methods could be applied to any occupant of a vehicle. In other words, a response system may be configured to detect if various other occupants of a motor vehicle are drowsy. Moreover, in some cases, one or more vehicle systems could be modified accordingly.

While various embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. A method of controlling one or more vehicle systems in a motor vehicle, comprising:

receiving monitoring information, the monitoring information including information from the one or more vehicle systems and information about a state of the autonomic nervous system of a driver;

determining a body state index of the driver based on the monitoring information;

changing an operating parameter of the one or more vehicle systems based on the body state index, wherein the operating parameter is used to determine activation of a particular function of the one or more vehicle systems;

determining if the driver is drowsy based on the body state index; and modifying the control of the one or more vehicle systems based the operating parameter when the driver is drowsy.

2. The method according to claim 1, wherein modifying the control of one or more vehicle systems when the driver is drowsy includes modifying an antilock brake system, an automatic brake prefill system, a brake assist system, a collision mitigation braking system and a collision warning system.

3. The method according to claim 2, wherein modifying the control of the one or more vehicle systems includes changing at least one operating parameter of the antilock brake system to decrease a stopping distance of the motor vehicle when the driver is drowsy.

4. The method according to claim 2, wherein modifying the control of the one or more vehicle systems includes automatically prefilling at least one brake line of the motor vehicle when the driver is drowsy.

5. The method according to claim 2, wherein modifying the control of the one or more vehicle systems includes providing braking assistance to the driver by lowering the braking force required to depress a brake pedal.

6. The method according to claim 2, wherein modifying the control of the one or more vehicle systems includes warning the driver earlier of potential collisions when the driver is drowsy.

7. The method according to claim 1, wherein the one or more vehicle systems is an auto cruise control system.

8. The method according to claim 7, wherein modifying the control of the one or more vehicle systems includes decreasing a headway distance when the driver is drowsy.

9. The method according to claim 7, wherein modifying the control of one or more vehicle systems includes automatically decreasing a current cruising speed when the driver is drowsy.

10. The method according to claim 1, wherein the one or more vehicle systems is an electronic stability control system.

11. The method according to claim 10, wherein modifying the control of the one or more vehicle systems includes reducing an allowable error between a measured yaw rate and a steering yaw rate when the driver is drowsy.

12. The method according to claim 1, wherein the one or more vehicle systems is a lane keep assist system.

13. The method according to claim 12, wherein modifying the control of the one or more vehicle systems includes alerting the driver when the motor vehicle crosses a lane marker boundary while the driver is fully alert and alerting the driver before the motor vehicle crosses the lane marker boundary while the driver is drowsy.

14. The method according to claim 1, wherein the one or more vehicle systems is a blind spot indicator system, and wherein modifying the control of the one or more vehicle systems includes modifying a blind spot detection area based on the body state index.

15. The method according to claim 1, wherein the one or more vehicle systems is an electronic pretensioning system for a seatbelt.

16. The method according to claim 15, wherein modifying the control of the one or more vehicle systems includes generating a warning pulse with the electronic pretensioning system when the driver is drowsy.

17. The method according to claim 15, wherein modifying the control of the one or more vehicle systems includes pretensioning the seatbelt when the driver is drowsy.

18. The method according to claim 1, wherein the one or more vehicle systems is an electronic power steering system.

19. The method according to claim 18, wherein modifying the control of the one or more vehicle systems includes decreasing power steering assistance when the driver is drowsy.

20. The method according to claim 1, wherein the one or more vehicle systems is a climate control system.

21. The method according to claim 20, wherein modifying the control of the one or more vehicle systems includes automatically adjusting a temperature in a cabin of the motor vehicle when the driver is drowsy.

22. The method according to claim 20, wherein modifying the control of the one or more vehicle systems includes automatically lowering a temperature in a cabin of the motor vehicle when the driver is drowsy.

23. The method according to claim 20, wherein modifying the control of the one or more vehicle systems includes automatically adjusting an airflow into a cabin of the motor vehicle when the driver is drowsy.

24. The method according to claim 1, wherein the one or more vehicle systems is a visual device for providing visual stimuli to the driver when the driver is drowsy.

25. The method according to claim 1, wherein the one or more vehicle systems is an audio device for generating sound when the driver is drowsy.

26. The method according to claim 1, wherein the one or more vehicle systems is a tactile device for providing tactile stimuli to the driver when the driver is drowsy.

27. The method according to claim 1, wherein the monitoring information is steering information.

28. The method according to claim 1, wherein the monitoring information is eye movement information.

29. The method according to claim 1, wherein the monitoring information is head movement information.

30. The method according to claim 1, wherein the monitoring information is lane departure information.

31. The method according to claim 1, wherein the monitoring information is received from a proximity sensor.

32. The method according to claim 31, wherein the proximity sensor is disposed in a headrest of the motor vehicle.

33. The method according to claim 32, wherein the proximity sensor is configured to detect a distance between a head of the driver and the headrest.

34. The method according to claim 1, wherein the monitoring information is received from a monitoring system.

35. The method according to claim 1, wherein the monitoring information is received from the one or more vehicle systems.

36. The method according to claim 1, wherein the monitoring information is received from the one or more vehicle systems and a monitoring system.

37. The method according to claim 1, wherein the one or more vehicle systems is a navigation system.

38. The method according to claim 37, wherein modifying the control of the one or more vehicle systems includes turning off the navigation system when the driver is drowsy.

39. The method according to claim 1, wherein modifying the control of the one or more vehicle systems includes comparing the monitoring information to the operating parameter and modifying the control of the one or more vehicle systems based on the comparing.

40. A method of controlling a vehicle system in a motor vehicle, comprising:
   receiving information from one or more sensors, the sensors being capable of detecting information about the autonomic nervous system of a driver and information about one or more vehicle systems;
   determining a body state index of the driver based on the information about the autonomic nervous system of a driver and information about the one or more vehicle systems;
   determining if the driver is drowsy based on the body state index; and
   modifying the control of the one or more vehicle systems when the driver is drowsy.

41. The method according to claim 40, wherein the information is heart information.

42. The method according to claim 40, wherein the information is respiratory rate information.

43. The method according to claim 40, wherein the information is perspiration information.

44. The method according to claim 40, wherein the information is pupil size information.

45. The method according to claim 40, wherein the sensor is associated with a seat of a motor vehicle.

46. The method according to claim 40, wherein the sensor is an optical sensing device.

47. The method according to claim 40, wherein the sensor is associated with an armrest of a motor vehicle.

48. The method according to claim 40, wherein the sensor is a portable sensor.

49. A method of controlling a vehicle system in a motor vehicle, comprising:
receiving monitoring information;
determining a body state index for a driver, the body state index characterizing drowsiness and based on the monitoring information;
determining a control coefficient based on the body state index, wherein the control coefficient is a value that varies as a function of the body state index;
determining a control parameter using the control coefficient, wherein the control parameter is used to determine activation of a particular function of the vehicle system; and
operating the vehicle system using the control parameter.

50. The method according to claim 49, wherein the body state index includes at least 2 values.

51. The method according to claim 50, wherein the body state index includes at least 3 values.

52. The method according to claim 50, wherein the body state index includes at least 4 values.

53. The method according to claim 49, wherein the body state index comprises discrete values.

54. The method according to claim 49, wherein the body state index comprises continuous values.

55. The method according to claim 49, wherein the control parameter comprises discrete values.

56. The method according to claim 49, wherein the control parameter comprises continuous values.

57. The method according to claim 49, wherein the value of the control parameter varies with the body state index.

58. The method according to claim 57, wherein the value of the control parameter increases as the body state index increases.

59. The method according to claim 57, wherein the value of the control parameter decreases as the body state index increases.

60. The method according to claim 49, wherein the step of determining the control coefficient includes a step of retrieving a relationship between the body state index and the control coefficient.

61. The method according to claim 49, wherein the control parameter is an activation threshold for an electronic stability assist system.

62. The method according to claim 49, wherein the control parameter is an activation threshold for a brake assist system.

63. The method according to claim 49, wherein the control coefficient is a blind spot zone coefficient that increases with the body state index and the control parameter is a zone threshold based on the control coefficient and an initial zone threshold, the zone threshold indicating a location threshold for determining when an object has entered into a blind spot monitoring zone for a blind spot indicator monitoring system.

64. The method according to claim 49, wherein the control parameter is a time to collision threshold for a forward collision warning system.

65. The method according to claim 49, wherein the control parameter is a time to lane crossing threshold for a lane departure warning system.

66. The method according to claim 49, wherein the control parameter is a status for a lane keep assist system.

67. The method according to claim 49, wherein the control parameter is a status indicating an operating state for a low speed follow system.

68. The method according to claim 49, wherein the control parameter is an electronic power steering status indicating an operating state of the electronic power steering system.

69. The method according to claim 49, wherein the control parameter is a cruise control status indicating an ON or OFF state.

* * * * *